US012678760B2

(12) United States Patent
Schroer et al.

(10) Patent No.: US 12,678,760 B2
(45) Date of Patent: *Jul. 14, 2026

(54) USE OF RENEWABLE ENERGY IN METHANOL SYNTHESIS

(71) Applicant: SABIC Global Technologies B.V., Bergen op Zoom (NL)

(72) Inventors: Joseph William Schroer, Sugar Land, TX (US); Scott Stevenson, Sugar Land, TX (US); Andrew Mark Ward, Redcar (GB); Tim Abbott, Redcar (GB); Kenneth Francis Lawson, Redcar (GB); Michael Edward Huckman, Sugar Land, TX (US); Zhun Zhao, Sugar Land, TX (US); Arno Oprins, Geleen (NL)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/763,904

(22) Filed: Jul. 3, 2024

(65) Prior Publication Data

US 2024/0359154 A1      Oct. 31, 2024

Related U.S. Application Data

(63) Continuation of application No. 17/310,074, filed as application No. PCT/US2020/013524 on Jan. 14, 2020, now Pat. No. 12,065,398.

(Continued)

(51) Int. Cl.
B01J 19/00 (2006.01)
B01D 53/047 (2006.01)
(Continued)

(52) U.S. Cl.
CPC ........ B01J 19/0053 (2013.01); B01D 53/047 (2013.01); B01D 53/265 (2013.01);
(Continued)

(58) Field of Classification Search
CPC ........ B01J 4/008; B01J 6/008; B01J 19/0053; B01J 19/2465; B01J 2219/0051;
(Continued)

(56) References Cited

U.S. PATENT DOCUMENTS 1,247,520 A    11/1917  Fessenden
2,002,525 A     5/1935  Cambron et al.
(Continued)

FOREIGN PATENT DOCUMENTS

CN         85101024        1/1987
CN         102008972       4/2011
(Continued)

OTHER PUBLICATIONS

Anonymous: "Renewable Electrolysis Hydrogen and Fuel Cells" Oct. 2014 https://nrel.gov/hydrogen/renewable-electrolysis.html.
(Continued)

*Primary Examiner* — Jafar F Parsa
(74) *Attorney, Agent, or Firm* — Norton Rose Fulbright US LLP

(57) ABSTRACT

A methanol synthesis plant comprising: a feed pretreating section operable to pretreat a feed stream; a synthesis gas (syngas) generation section comprising one or more reactors operable to produce a syngas synthesis product stream comprising synthesis gas from the feed stream; a methanol synthesis section comprising one or more methanol synthesis reactors operable to produce a synthesis product comprising methanol; and/or a methanol purification section operable to remove at least one component from the synthesis product to provide a purified methanol product;
(Continued)

wherein the methanol synthesis plant is configured such that, relative to a conventional methanol synthesis plant, more of the net energy required by the methanol synthesis plant, the feed pretreating section, the syngas generation section, the methanol synthesis section, the methanol purification section, or a combination thereof, is provided by a non-carbon based energy source, a renewable energy source, and/or electricity.

20 Claims, 11 Drawing Sheets

Related U.S. Application Data

(60) Provisional application No. 62/792,617, filed on Jan. 15, 2019, provisional application No. 62/792,631, filed on Jan. 15, 2019, provisional application No. 62/792,633, filed on Jan. 15, 2019, provisional application No. 62/792,632, filed on Jan. 15, 2019, provisional application No. 62/792,622, filed on Jan. 15, 2019, provisional application No. 62/792,619, filed on Jan. 15, 2019, provisional application No. 62/792,634, filed on Jan. 15, 2019, provisional application No. 62/792,627, filed on Jan. 15, 2019, provisional application No. 62/792,612, filed on Jan. 15, 2019, provisional application No. 62/792,636, filed on Jan. 15, 2019, provisional application No. 62/792,637, filed on Jan. 15, 2019, provisional application No. 62/792,615, filed on Jan. 15, 2019, provisional application No. 62/792,635, filed on Jan. 15, 2019.

(51) Int. Cl.

| | |
|---|---|
| *B01D 53/26* | (2006.01) |
| *B01J 4/00* | (2006.01) |
| *B01J 6/00* | (2006.01) |
| *B01J 19/24* | (2006.01) |
| *C01B 3/12* | (2006.01) |
| *C01B 3/34* | (2006.01) |
| *C01B 3/48* | (2006.01) |
| *C01B 3/56* | (2006.01) |
| *C01C 1/02* | (2006.01) |
| *C01C 1/04* | (2006.01) |
| *C07C 4/02* | (2006.01) |
| *C07C 4/04* | (2006.01) |
| *C07C 29/132* | (2006.01) |
| *C07C 29/152* | (2006.01) |
| *F25J 3/02* | (2006.01) |
| *H01M 8/04082* | (2016.01) |
| *H01M 8/0606* | (2016.01) |
| *H01M 8/0612* | (2016.01) |
| *H02J 15/20* | (2026.01) |
| *H02J 15/50* | (2026.01) |
| *H01M 8/1007* | (2016.01) |

(52) U.S. Cl.
CPC .............. *B01J 4/008* (2013.01); *B01J 6/008* (2013.01); *B01J 19/0033* (2013.01); *B01J 19/2465* (2013.01); *C01B 3/12* (2013.01); *C01B 3/342* (2013.01); *C01B 3/48* (2013.01); *C01B 3/56* (2013.01); *C01C 1/02* (2013.01); *C01C 1/0417* (2013.01); *C01C 1/0488* (2013.01); *C07C 4/02* (2013.01); *C07C 4/04* (2013.01); *C07C 29/132* (2013.01); *C07C 29/152* (2013.01); *F25J 3/0233* (2013.01); *H01M 8/04201* (2013.01); *H01M 8/0606*
(2013.01); *H01M 8/0618* (2013.01); *H02J 15/20* (2026.01); *H02J 15/50* (2026.01); *B01D 2256/16* (2013.01); *B01D 2256/245* (2013.01); *B01J 2219/00051* (2013.01); *B01J 2219/00132* (2013.01); *B01J 2219/00761* (2013.01); *B01J 2219/0871* (2013.01); *C01B 2203/0216* (2013.01); *C01B 2203/0233* (2013.01); *C01B 2203/0238* (2013.01); *C01B 2203/0244* (2013.01); *C01B 2203/0261* (2013.01); *C01B 2203/0283* (2013.01); *C01B 2203/0294* (2013.01); *C01B 2203/04* (2013.01); *C01B 2203/061* (2013.01); *C01B 2203/066* (2013.01); *C01B 2203/068* (2013.01); *C01B 2203/085* (2013.01); *C01B 2203/148* (2013.01); *H01M 8/1007* (2016.02)

(58) Field of Classification Search
CPC ............ B01J 2219/0871; C07C 29/152; C07C 29/1518; C07C 31/04; C01B 3/12; C01B 3/342; C01B 3/48; C01B 3/56
See application file for complete search history.

(56) References Cited

U.S. PATENT DOCUMENTS

| | | | |
|---|---|---|---|
| 3,644,100 | A | 2/1972 | Lhonore et al. |
| 3,705,009 | A | 12/1972 | Dougherty |
| 4,140,602 | A | 2/1979 | Lewis et al. |
| 4,158,637 | A | 6/1979 | Jones |
| 4,233,127 | A | 11/1980 | Monahan |
| 4,391,794 | A | 7/1983 | Silberring |
| 4,434,133 | A | 2/1984 | Down et al. |
| 4,684,759 | A | 8/1987 | Lam |
| 5,059,404 | A | 10/1991 | Mansour |
| 5,122,299 | A | 6/1992 | Leblanc |
| 5,180,570 | A | 1/1993 | Lee et al. |
| 5,321,191 | A | 6/1994 | Alagy et al. |
| 5,620,670 | A | 4/1997 | Benham et al. |
| 6,100,303 | A | 8/2000 | Hirotani et al. |
| 6,183,703 | B1 | 2/2001 | Hsu et al. |
| 6,506,510 | B1 | 1/2003 | Sioui et al. |
| 7,288,690 | B2 | 10/2007 | Bellet et al. |
| 7,300,642 | B1 | 11/2007 | Pedersen et al. |
| 2004/0033174 | A1 | 2/2004 | Bruck |
| 2004/0060301 | A1 | 4/2004 | Aceves et al. |
| 2004/0060304 | A1 | 4/2004 | Aceves et al. |
| 2004/0127759 | A1 | 7/2004 | Van Egmond |
| 2005/0271924 | A1 | 12/2005 | Coors et al. |
| 2006/0116543 | A1 | 6/2006 | Bellet |
| 2006/0207178 | A1 | 9/2006 | Hsu |
| 2006/0211777 | A1 | 9/2006 | Severinsky |
| 2007/0204512 | A1 | 9/2007 | Self et al. |
| 2008/0156696 | A1 | 7/2008 | Niccum et al. |
| 2011/0042620 | A1 | 2/2011 | Singh et al. |
| 2011/0229780 | A1 | 9/2011 | Kershaw |
| 2012/0055331 | A1 | 3/2012 | Steele |
| 2012/0149788 | A1 | 6/2012 | Ahmed et al. |
| 2012/0186252 | A1 | 7/2012 | Schmidt |
| 2013/0177975 | A1 | 7/2013 | Goetz et al. |
| 2013/0252034 | A1 | 9/2013 | Hu et al. |
| 2014/0194539 | A1 | 7/2014 | Hammad et al. |
| 2015/0129805 | A1 | 5/2015 | Karpenko et al. |
| 2015/0232999 | A1 | 8/2015 | Busskamp et al. |
| 2015/0275108 | A1 | 10/2015 | Gueh |
| 2016/0017800 | A1 | 1/2016 | Simpson |
| 2016/0060537 | A1 | 3/2016 | Hsu |
| 2016/0122194 | A1 | 5/2016 | Markowz et al. |
| 2016/0347908 | A1 | 12/2016 | Muller et al. |
| 2016/0369191 | A1 | 12/2016 | Ward |
| 2017/0137355 | A1* | 5/2017 | Sarsani ................... C01B 3/36 |
| 2017/0362147 | A1 | 12/2017 | Won et al. |
| 2018/0237555 | A1 | 8/2018 | Buach et al. |
| 2020/0055738 | A1 | 2/2020 | Baratto et al. |
| 2020/0299143 | A1 | 9/2020 | Højlund Nielsen |

(56) References Cited

U.S. PATENT DOCUMENTS

| | | |
|---|---|---|
| 2020/0406212 A1 | 12/2020 | Mortensen et al. |
| 2021/0061655 A1 | 3/2021 | El-Halwagi et al. |
| 2021/0113980 A1 | 4/2021 | Van Der Ploeg |
| 2021/0261425 A1 | 8/2021 | Rossi et al. |
| 2021/0301685 A1 | 9/2021 | Balthasar et al. |
| 2022/0119269 A1* | 4/2022 | Huckman ............. C01C 1/0417 |

FOREIGN PATENT DOCUMENTS

| | | |
|---|---|---|
| CN | 102753656 | 10/2012 |
| CN | 103003192 | 3/2013 |
| CN | 103025649 | 4/2013 |
| CN | 105209372 | 12/2015 |
| CN | 105209373 | 12/2015 |
| CN | 107223114 | 9/2017 |
| CN | 108368037 | 8/2018 |
| DE | 102016209155 | 11/2017 |
| EA | 029413 | 3/2018 |
| EP | 0539244 A1 | 4/1993 |
| EP | 2281793 | 2/2011 |
| EP | 2662327 | 11/2013 |
| EP | 3249027 | 11/2017 |
| EP | 3017025 | 3/2018 |
| FR | 2473032 | 7/1981 |
| JP | BS4614246 | 4/1971 |
| JP | AS54136574 | 10/1979 |
| JP | AS62089634 | 4/1987 |
| JP | H0565237 | 3/1993 |
| JP | H05147903 | 6/1993 |
| JP | AH5222379 | 8/1993 |
| JP | H05222379 | 8/1993 |
| JP | AH9235564 | 9/1997 |
| JP | 2003504485 | 2/2003 |
| JP | A20045243338 | 8/2004 |
| JP | A2005515295 | 5/2005 |
| JP | A2009531529 | 9/2009 |
| JP | 4585729 B2 | 11/2010 |
| JP | 2013537042 A | 9/2013 |
| KR | 2014-0140562 | 3/2012 |
| RU | 2203214 | 4/2003 |
| RU | 2005/102272 | 7/2006 |
| RU | 2501841 | 12/2013 |
| RU | 2534192 | 11/2014 |
| RU | 2570659 | 12/2015 |
| RU | 2617772 | 4/2017 |
| SU | 823377 | 4/1981 |
| WO | WO 02/074721 | 9/2002 |
| WO | WO 03/062352 | 7/2003 |
| WO | WO 2007117919 | 10/2007 |
| WO | WO 2008/122399 | 10/2008 |
| WO | WO 2011/083333 | 7/2011 |
| WO | WO 2013/124092 | 8/2013 |
| WO | WO 2016/209508 | 12/2016 |
| WO | WO 2018/234971 | 12/2018 |
| WO | WO 2023/202973 | 10/2023 |
| WO | WO 2023/202974 | 10/2023 |

OTHER PUBLICATIONS

Bazzanella et al., "Low carbon energy and feedstock for the European chemical industry", pp. 1-3000, 2017.

Doyle, "BASF announces four research projects for reducing C02 emissions—News—The Chemical Engineer", pp. 1-14, 2019.

Ekejiuba "Evaluation of the Exact Production Quantity of Nitrogen Fertilizer in Real- Time from any Particular Associated Gas Flare Volume in Nigeria" International Journal of Applied Science and Technology vol. 7, No. 3, Sep. 3, 2017, pp. 87-100.

Extended European Search Report issued in corresponding European Application No. 20741340.2 dated Oct. 25, 2022.

Hobson, et al. "Renewable methanol report" *Methanol Institute*, Dec. 2018, pp. 1-26.

Hydrogen Council "How hydrogen empowers the energy transition" Jan. 2017 https://hydrogencouncil.com/wp-content/uploads/2-17/06/Hydrogen-Council-Vision-Document.pdf.

International Search Report and Written Opinion issued in corresponding International application PCT/US2020/013524 mailed Apr. 9, 2020.

Lewis, Jonathan "Fuels Without Carbon Prospects and the Pathway Forward for Zero-Carbon Hydrogen and Ammonia Fuels" Dec. 2018 https://www.catf.us.resouce/fuels-ithout-carbon.

Max Appl. "Ammonia, 3. Production Plants." *Ullman's Encyclopedia of Industrial Chemistry*, Wiley-VCH, 2012, pp. 227-261.

Mortensen, et al. "Direct Hysteresis Heating of Catalytically Active Ni—Co Nanoparticles as Steam Reforming Catalyst" Industrial & Engineering Chemistry Research vol. 56, No. 47, Nov. 15, 2017, pp. 14006-14013.

Office Action issued in corresponding Chinese Patent Application No. 202080021307.3, dated Apr. 20, 2023 (Machine Translation Provided).

Office Action issued in corresponding Russian Application No. 2021123895 dated Jun. 9, 2023.

Pattabathula, et al. "Introduction to Ammonia Production" Chemical Engineering Progress Sep. 2016, pp. 69-75.

Wang et al., "Greening Ammonia toward the Solar Ammonia Refinery" Joule, 2, Jun. 20, 2018, pp. 1055-1074.

Weinian, Feng, et al. "Encyclopedia of Chemical Engineering" (vol. 3 "Tool Materials—Power Generation Dao fa", pp. 407-408, Chemical Industry Press, Mar. 1993. (no translation available).

Wismann, et al., "Electrified methane reforming: A compact approach to greener industrial hydrogen production" *Science*, vol. 364, No. 6442, May 24, 2019, pp. 756-759.

Zimmermann, et al., "Ethylene" In: Ullmann's Encyclopedia of Wiley-VCH Industrial Chemistry, 2009.

Office Action issued in corresponding Chinese Application No. 202311659620.1, dated Sep. 29, 2025 (Machine Translation provided).

Rafiqul et al., "Energy efficiency improvements in ammonia production—perspectives and uncertainties." *Energy*, vol. 30, 2005, pp. 2487-2504.

Office Action issued in corresponding Chinese Application No. 202311659620.1, dated Mar. 25, 206 (Machine Translation provided).

* cited by examiner

EXAMPLE 8

USE OF RENEWABLE ENERGY IN METHANOL SYNTHESIS

CROSS-REFERENCE TO RELATED APPLICATIONS

This application is a continuation of U.S. application Ser. No. 17/310,074, filed Jul. 15, 2021, which is a national phase application under 35 U.S.C. § 371 of International Application No. PCT/US2020/013524 filed Jan. 14, 2020, which claims the benefit of priority to U.S. Provisional Patent Application No. 62/792,612 filed Jan. 15, 2019, U.S. Provisional Patent Application No. 62/792,615 filed Jan. 15, 2019, U.S. Provisional Patent Application No. 62/792,617 filed Jan. 15, 2019, U.S. Provisional Patent Application No. 62/792,619 filed Jan. 15, 2019, U.S. Provisional Patent Application No. 62/792,622 filed Jan. 15, 2019, U.S. Provisional Patent Application No. 62/792,627 filed Jan. 15, 2019, U.S. Provisional Patent Application No. 62/792,631 filed Jan. 15, 2019, U.S. Provisional Patent Application No. 62/792,632 filed Jan. 15, 2019, U.S. Provisional Patent Application No. 62/792,633 filed Jan. 15, 2019, U.S. Provisional Patent Application No. 62/792,634 filed Jan. 15, 2019, U.S. Provisional Patent Application No. 62/792,635 filed Jan. 15, 2019, U.S. Provisional Patent Application No. 62/792,636 filed Jan. 15, 2019, and U.S. Provisional Patent Application No. 62/792,637 filed Jan. 15, 2019, each of which are hereby incorporated by reference in their entireties.

TECHNICAL FIELD

The present disclosure relates to the use of renewable energy in methanol synthesis; more particularly, the present disclosure relates to the electrification of a methanol synthesis plant; still more particularly, the present disclosure relates to a reduction in environmental emissions, such as carbon dioxide, by reducing the combustion of hydrocarbons (e.g., natural gas/fossil fuels) for fuel in a methanol synthesis plant.

BACKGROUND

Chemical synthesis plants are utilized to provide a variety of chemicals. Often, a dedicated fuel is burned or 'combusted' to provide heat of reaction for chemical synthesis, energy to heat one or more process streams, energy to vaporize liquids (e.g., boil water used as a diluent), energy to do work (e.g., drive a compressor or pump), or energy for other process operations throughout the chemical synthesis plant. Such burning or combustion of fuels results in the production of flue gases, which can be harmful to the environment, and also results in a loss of energy efficiency of the process. Likewise, steam is often conventionally utilized as a plant-wide heat and/or energy transfer fluid within chemical synthesis plants. The steam utilized for the heat and/or energy transfer is often produced via the combustion of a fuel, resulting in the production of additional flue gas and further energy efficiency losses during the chemical synthesis. Additionally, the use of a material that could otherwise be utilized as a reactant for combustion as a fuel also reduces an amount of the desired chemical product produced in the chemical synthesis plant from a given amount of the material. Accordingly, a need exists for enhanced systems and methods of chemical synthesis whereby an amount of fuels, especially fossil fuels, burned to provide energy is reduced or eliminated. Desirably, such systems and methods also provide for an increase in energy efficiency and/or a decrease in emissions, such as emissions of greenhouse gases (GHG), by the chemical synthesis plant.

SUMMARY

Herein disclosed is a methanol synthesis plant comprising: a feed pretreating section operable to pretreat a feed stream comprising LPG, naphtha, biogas, methane, ethane, propane, butane, naphtha boiling range components, coal, petcoke, or a combination thereof; a synthesis gas (syngas) generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream; a methanol synthesis section comprising one or more methanol synthesis reactors operable to produce a synthesis product comprising methanol; and/or a methanol purification section operable to remove at least one component from the synthesis product to provide a purified methanol product; wherein the methanol synthesis plant is configured such that, relative to a conventional methanol synthesis plant, more of the net energy required by the methanol synthesis plant, the feed pretreating section, the syngas generation section, the methanol synthesis section, the methanol purification section, or a combination thereof, is provided by a non-carbon based energy source, a renewable energy source, and/or electricity.

Also disclosed herein is a methanol synthesis plant comprising: a feed pretreating section operable to pretreat a feed stream comprising LPG, naphtha, biogas, methane, ethane, propane, butane, naphtha boiling range components, coal, petcoke, or a combination thereof; a syngas generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream; a methanol synthesis section comprising one or more methanol synthesis reactors operable to produce a synthesis product comprising methanol; and/or a methanol synthesis section comprising one or more methanol synthesis reactors operable to produce a synthesis product comprising methanol; and/or a methanol purification section operable to remove at least one component from the synthesis product to provide a purified methanol product; wherein the methanol synthesis plant is configured such that a majority of the net energy required by the methanol synthesis plant, the feed pretreating section, the syngas generation section, the methanol synthesis section, the methanol purification section, or a combination thereof, is provided by electricity.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
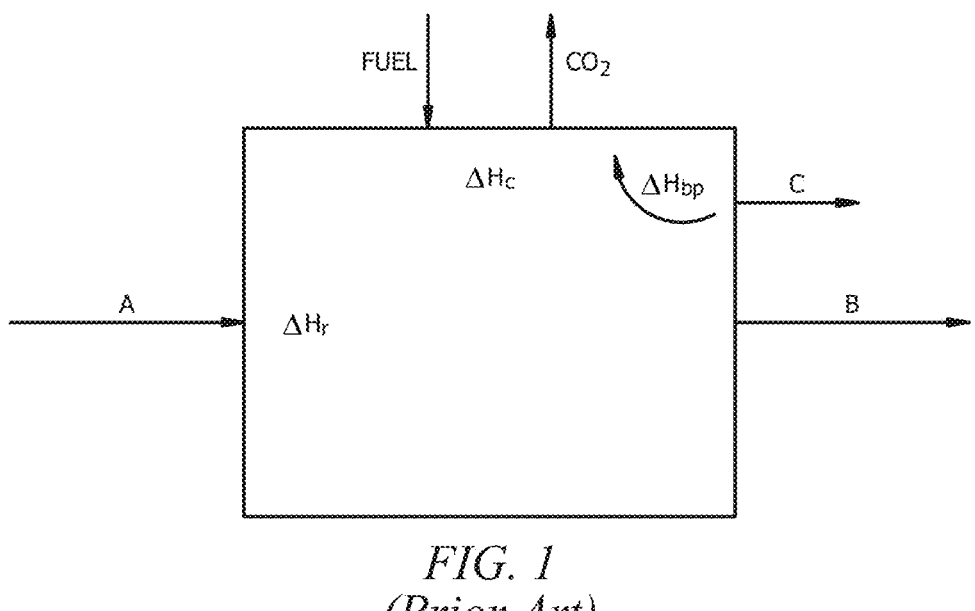
FIG. 1 shows a conceptual diagram of a typical prior art chemical process.

It should be understood at the outset that although an illustrative implementation of one or more embodiments are provided below, the disclosed compositions, methods, and/or products may be implemented using any number of techniques, whether currently known or not yet in existence. The disclosure should in no way be limited to the illustrative implementations, drawings, and techniques illustrated hereinbelow, including the exemplary designs and implementations illustrated and described herein, but may be modified within the scope of the appended claims along with their full scope of equivalents.

While the following terms are believed to be well understood by one of ordinary skill in the art, the following definitions are set forth to facilitate explanation of the presently disclosed subject matter. Unless defined otherwise, all technical and scientific terms used herein have the same meaning as commonly understood to one of ordinary skill in the art to which the presently disclosed subject matter belongs.

As utilized herein, an 'intermittent energy source' or 'IES' is any source of energy that is not continuously available for conversion into electricity and outside direct control because the used energy cannot be stored or is economically undesirable. The availability of the intermittent energy source may be predictable or non-predictable. A renewable intermittent energy source is an intermittent energy source that is also a source of renewable energy, as defined hereinbelow. 'Intermittent electricity' refers to electricity produced from an IES.

As utilized herein, 'renewable energy' and 'non-fossil based energy ($E_{NF}$)' includes energy derived from a sustainable energy source that is replaced rapidly by a natural, ongoing process, and nuclear energy. Accordingly, the terms 'renewable energy' and 'non-fossil based energy ($E_{NF}$)' refer to energy derived from a non-fossil fuel based energy source (e.g., energy not produced via the combustion of a fossil fuel such as coal or natural gas), while 'non-renewable' or 'fossil based energy ($E_F$)' is energy derived from a fossil fuel-based energy source (e.g., energy produced via the combustion of a fossil fuel). Fossil fuels are natural fuels, such as coal or gas, formed in the geological past from the remains of living organisms. Accordingly, as utilized herein, 'renewable' and 'non-fossil based energy ($E_{NF}$)' include, without limitation, wind, solar power, water flow/movement, or biomass, that is not depleted when used, as opposed to 'non-renewable' energy from a source, such as fossil fuels, that is depleted when used. Renewable energy thus excludes fossil fuel based energy ($E_F$) and includes biofuels.

As utilized herein, 'non-carbon based energy ($E_{NC}$)' is energy from a non-carbon based energy source (e.g., energy not produced via the combustion of a carbon-based fuel such as a hydrocarbon), while carbon based energy ($E_C$) is energy from a carbon-based energy source (e.g., energy produced via the combustion of a carbon-based fuel such as a hydrocarbon). Nuclear energy is considered herein a renewable, non-fossil ($E_{NF}$) based energy and a non-carbon based energy ($E_{NC}$). Carbon-based energy ($E_C$) can thus be renewable (e.g., non-fossil fuel based) or non-renewable (e.g., fossil fuel-based). For example, various carbon-based biofuels are herein considered renewable, carbon-based energy sources.

As utilized herein, 'renewable electricity' indicates electricity produced from a renewable energy source, while 'non-renewable electricity' is electricity produced from a non-renewable energy source. As utilized herein 'non-carbon based electricity' indicates electricity produced from a non-carbon based energy source, while 'carbon-based electricity' is electricity produced from a carbon-based energy source.

For example, in embodiments, renewable electricity and/or heat throughout the herein-disclosed methanol synthesis plant can be provided by the combustion of renewable hydrocarbons that come from renewable (e.g., biological) sources. For example, renewable electricity can, in embodiments, be produced via the combustion of an $E_{NF}/E_C$ energy source comprising methane produced in a digester fed with agricultural wastes. Likewise, in embodiments, an $E_{NF}/E_C$ energy source comprising synthesis gas produced using short cycle carbon waste materials can be utilized as a fuel (e.g., combusted to produce renewable electricity and/or heat). Desirably, the carbon dioxide generated by such combustion is recaptured (e.g., by the growth of a new crop).

As utilized herein, 'externally' combusting a fuel refers to combusting a fuel outside of a reactor, e.g., in a furnace. Combustion as a part of the primary reaction (e.g., combustion which takes place with reforming in autothermal reforming (ATR)) would not be considered 'externally' combusting. As utilized herein, a 'dedicated' fuel is a fuel or portion of a feed stream introduced solely to provide fuel value (e.g., combustion heat) and not be converted into product.

As utilized herein, 'heat transfer steam ($S_{HT}$)' indicates steam produced solely or primarily as an energy or heat transfer medium (e.g., steam not utilized as a diluent and/or reactant).

As utilized herein, 'net' heat input or removal refers to heat input or removal that results in primary energy consumption, e.g., heat input or removal not provided from another section or stream of the plant, e.g., not provided via heat exchange with another process stream. Similarly, 'net' energy refers to energy that results in primary energy consumption, e.g., energy not provided from another section or stream of the plant, e.g., thermal energy not provided via heat exchange with another process stream.

As utilized herein' 'powering' indicates supplying with mechanical and/or electrical energy.

As utilized herein' 'heating' indicates supplying with thermal energy. As utilized herein 'cooling' indicates the removal of thermal energy therefrom. As utilized herein, 'direct' heating or cooling refer to heating or cooling without the use of a heat transfer medium/fluid; 'indirect' heating or cooling refer to heating or cooling via a heat transfer medium/fluid.

As utilized herein' 'most' or 'a majority' indicates more than 50% or more than half.

As utilized herein, a 'desired' parameter (e.g., desired temperature) may refer to an intended or target value for the parameter, for example a predetermined value such as a set-point value used for process control.

Amount of electricity consumed: References to consumption of electricity may refer to a rate at which electricity is used (e.g., in MW), as measured at a particular location. For example, a rate may be calculated at the boundary of each electrified furnace or at an overall olefin synthesis plant boundary. This calculation may consider all electricity used within that location.

Flue gas: A mixture of gases that may be produced by the burning of fuel or other materials in a power station and/or industrial plant, where the mixture of gases may be extracted via ducts.

Flue gas heat recovery: Hue gas heat recovery may refer to the extraction of useful thermal energy from hot flue gases, for example by passing said hot flue gas over one or more heat exchangers to raise the temperature of a cooler process fluid and/or change the phase of said fluid (e.g., boil water to raise steam). Any energy remaining in the flue gas after any flue gas heat recovery may be termed flue gas (energy) loss. A flue gas heat recovery section may be the equipment and corresponding location of said equipment used to recover flue gas heat. A lack of flue gas heat recovery section may mean there is no equipment or area where heat is recovered from hot flue gases.

Convection section: A convection section may be a portion of a furnace (e.g., steam cracking furnace or reforming furnace) where heat is recovered from hot flue gases by convective heat transfer. A lack of convection section may mean that there is no equipment or area where heat is recovered by convective heat transfer from hot flue gases.

"Steam-free" or "Substantially Steam-free": "Steam free" may refer to a process where steam is not used to transfer energy from one process operation to another, or to bring energy into the process from outside. "Substantially steam-free" may mean that the use of steam to transfer energy from one process operation to another or to bring energy into the process from outside has been minimized such that the sum of all energy transfers using steam amount to less than approximately 10%, approximately 20%, or approximately 30% of the net energy provided. Steam used as a reactant, a diluent, obtained as a product, or directly mixed with a process stream may be termed "process steam" and is not included in this definition.

Primary energy transfer medium: A primary energy transfer medium may be a substance that is used to move energy in the form of thermal energy from one process operation to another, or to bring energy into a process. Note that a substance may serve more than one purpose in a process such as acting as a reactant or reaction diluent whilst also acting as a medium to transfer heat from one process operation to another. In such instances, the use of steam as reactant or diluent may be considered primary and the effect of also transferring heat may be considered secondary.

Resistive heating: Resistive heating may be heating by means of passing electric current through resistive units.

Inductive heating: Induction heating may be a process of heating an electrically conducting object (usually a metal) by electromagnetic induction.

Radiant heating: Radiant heating may be a process of heating an object via radiation from one or more hotter objects.

Externally combusting: Externally combusting may mean burning fuel to generate heat and transferring this heat to a process fluid across a surface (e.g., a tube wall) such that combustion products do not mix with the process fluid.

Thermoelectric device: A thermoelectric device may be a device for the direct conversion of temperature differences to electric voltage (or vice versa) across a thermocouple.

Isothermal operation: Isothermal operations may be operations at a constant temperature. Isothermal operation can keep temperature within 0.5%, 1%, 2%, 3%, 4%, 5% up to 10% of the predetermined operation temperature.

Convective heat transfer: Convective heat transfer may be the movement of heat from one place to another by the movement of a fluid or fluids.

Although the majority of the above definitions are substantially as understood by those of skill in the art, one or more of the above definitions can be defined hereinabove in a manner differing from the meaning as ordinarily understood by those of skill in the art, due to the particular description herein of the presently disclosed subject matter.

FIG. 1 shows a conceptual diagram of a typical traditional chemical process. The goal of this process is to convert feed A into product B, although often some byproducts (indicated as stream C) are also produced.

The unit operations used to effect this transformation require significant amounts of energy. Conventionally, this energy is primarily supplied by burning a fuel, often natural gas, to generate heat, denoted in FIG. 1 as $\Delta H_c$ (e.g., heat of combustion). This results in the undesirable production and emission of carbon dioxide ($CO_2$). Additional energy may be supplied by the heat of reaction, $\Delta H_r$, if the reaction is exothermic; if the reaction is endothermic, an additional amount of energy equal to $\Delta H_r$ will need to be added. The total energy balance may also be affected if some byproducts are burned to produce energy, indicated as $\Delta H_{bp}$. However, many chemical processes, even those involving exothermic reactions, are net energy consumers and thus require an external source of energy (typically provided by a hydrocarbon fuel(s)) to provide net process energy.

Electricity is usually only a small external input into most chemical production processes. Internal electrical requirements, such as for lighting or control, are usually so small as to be negligible, and in those few processes which require large amounts of electricity, for example, electrochemical reactors (e.g., the chlor-alkali process to make chlorine ($Cl_2$) and sodium hydroxide (NaOH)), this electricity is commonly generated within the plant boundaries by the combustion of hydrocarbons, and, even when not generated within the plant boundaries, if the electricity is obtained by the combustion of hydrocarbons rather than renewably, such use of electricity is equivalent in terms of energy efficiency and $CO_2$ emissions to on-site production of the electricity via hydrocarbon combustion.

Within most chemical production processes, energy consumption can conveniently be divided into three main categories. In the first such broad category, referred to herein as first category C1, heat is supplied directly as thermal energy by the combustion of a fuel (e.g., natural gas/fossil fuels) in a furnace. (As utilized, here, 'directly' indicates the absence of an intermediate heat transfer medium, such as steam.) These furnaces are often operated at high temperature and require large heat fluxes. The energy efficiency of such furnaces is limited by the heat losses in the furnace flue gas. Even where these heat losses are minimized by the cooling of the flue gas to recover energy, for example to generate steam or provide process heating, the conversion of the chemical energy contained in the fuel to usable thermal energy generally does not exceed 85 to 90%, even with substantial investment and loss of design and operating flexibility.

The second broad category, referred to herein as second category C2, of energy consumption in chemical processes comprises the heating of various chemical streams, primarily either to raise the temperature thereof to a desired reaction temperature or to provide energy for separations, most commonly distillation. Although some of this heat can be obtained by exchange with other chemical streams, it is most typically provided either by steam generated directly by the combustion of hydrocarbon fuels (e.g., natural gas/ fossil fuels) or by heat transfer from the flue gas from high-temperature furnaces (e.g., from category C1). Most modern chemical processes include a relatively complicated steam system (or other heat transfer fluid system which will generically be referred to herein for simplicity as a steam heat transfer system) to move energy from where it is in excess to where it is needed. This steam system may include multiple pressure levels of steam to provide heat at different temperatures, as well as a steam and condensate recovery system, and is subject to corrosion, fouling, and other operational difficulties, including water treatment and contaminated condensate disposal. The fraction of the energy contained in the steam that can be used to heat process streams is generally limited to 90 to 95% by practical constraints on heat transfer, steam condensation, and boiler water recycle. If the steam was generated by an on-purpose external boiler, at most 80 to 85% of the chemical energy contained in the fuel will be used as heat by the chemical process, since an additional 10 to 15% or more will be lost to flue gas as in first category C1.

The third major category, referred to herein as third category C3, of energy usage in chemical processes is energy utilized to perform mechanical work. This work is primarily utilized for pressurizing and moving fluids from one place to another, and is used to drive rotating equipment such as pumps, compressors, and fans. This third category C3 also includes refrigeration equipment, since it is primarily powered by compression. In most chemical facilities, the energy for this work is provided by steam, obtained either by heat transfer with hot process streams, by heat transfer with partially-cooled flue gas streams from a furnace (e.g., in the convection section) in category C1, or directly from the combustion of hydrocarbons (e.g., natural gas/fossil fuels) in an on-purpose external boiler. Because of limitations on the conversion of thermal energy to mechanical work, the energy efficiency of these uses relative to the contained chemical energy of the hydrocarbons used as fuel is low, typically only 25 to 40%.

It has been unexpectedly discovered that using electricity (e.g., renewable and/or non-renewable electricity) to replace energy obtained from a hydrocarbon fuel in a chemical process can improve the process by increasing overall energy efficiency, while decreasing carbon dioxide emissions. In some cases, using electricity (e.g., renewable and/or non-renewable electricity) to replace energy obtained from a hydrocarbon fuel in a chemical process can also improve reliability and operability, decrease emissions of, for example, NOx, SOx, CO, and/or volatile organic compounds, and/or decrease production costs (e.g., if low-cost electricity is available).

According to embodiments of this disclosure, heat conventionally supplied as thermal energy by the combustion of a fuel (e.g., natural gas/fossil fuels) in a furnace and/or other heating in first category C1 is replaced by electrical heating. Electrical heat, electrical heating, generating heat electrically, electrical heater apparatus, and the like refer to the conversion of electricity into thermal energy available to be applied to a fluid. Such electrical heating includes, without limitation, heating by impedance (e.g., where electricity flows through a conduit carrying the fluid to be heated), heating via ohmic heating, plasma, electric arc, radio frequency (RF), infrared (IR), UV, and/or microwaves, heating by passage over a resistively heated element, heating by radiation from an electrically-heated element, heating by induction (e.g., an oscillating magnetic field), heating by mechanical means (e.g. compression) driven by electricity, heating via heat pump, heating by passing a relatively hot inert gas or another medium over tubes containing a fluid to be heated, wherein the hot inert gas or the another medium is heated electrically, or heating by some combination of these or the like.

According to embodiments of this disclosure, the utilization of steam (or another heat transfer fluid) as in second category C2 is eliminated and/or any steam (or other fluid) utilized solely as an intermediate heat transfer medium is electrically produced or heated (e.g., via electrical heating of water).

According to embodiments of this disclosure, conventional rotating equipment (e.g., steam turbines) utilized in third category C3 is replaced with electrically driven apparatus. According to embodiments of this disclosure, heat removal in third category C3 is replaced by electrically-powered heat removal, e.g., cooling and/or refrigeration. Electrical cooling, electrical coolers, removing heat electrically, electrical cooling or refrigeration apparatus, and the like refer to the removal of thermal energy from a fluid. Such electrical cooling includes, without limitation, cooling by electrically powered apparatus. For example, and without limitation, electrical cooling can be provided by powering a refrigeration cycle with electricity, wherein a refrigerant is compressed by an electrically powered compressor. As another example, electrical cooling can be provided by powering a cooling fan that blows air, wherein the air cools a process fluid or element. In embodiments, electrical heating and cooling can be effected by any electrical source.

Figure 2:
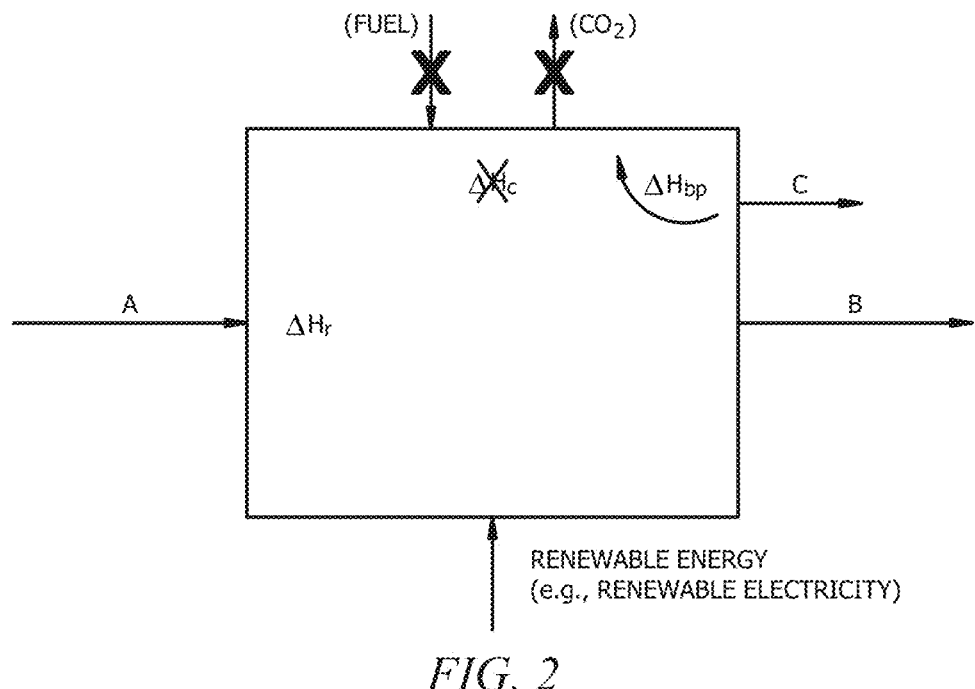
FIG. 2 shows a conceptual diagram of a chemical process powered by renewable energy, according to embodiments of this disclosure.

FIG. 2 is a schematic of a chemical process powered by renewable energy, according to embodiments of this disclosure. As shown in FIG. 2, a process driven by renewable energy can, in embodiments, appear similar to a conventional chemical process. However, a portion, a majority, or, in some cases, substantially all of the energy input supplied by fuel can be replaced by renewable energy and/or by renewable electricity. Such replacement of fuel input by non-carbon based energy, renewable energy, and/or renewable electricity will allow for a significant decrease in $CO_2$ emissions, in embodiments. In embodiments, any available form of renewable energy can be employed. However, the gains may be greatest if renewable electricity is utilized. The renewable energy can be obtained from, for example and without limitation, solar power, wind power, or hydroelectric power. Other types of renewable energy can also be applied in chemical plants according to embodiments of this disclosure. For example, in embodiments, concentrated solar power, geothermal energy, and/or the use of direct solar heating can be used to provide thermal energy and to decrease $CO_2$ emissions.

One of the main advantages to supplying needed energy via (e.g., renewable) electricity can be that the energy efficiency of the process will increase. Table 1 shows the energy efficiency of unit operations exemplifying the three categories of energy use in a chemical plant described above as C1, C2, and C3. It can be seen from Table 1 that the efficiency of each of the three categories of energy consumption is greater when electrical power is used. The gain can be greatest when steam drives for rotating equipment are replaced, according to embodiments of this disclosure, with electrical motors (as in third category C3, discussed hereinabove), which can operate with as much as three times the energy efficiency of steam drives. These gains are only realized when the electricity is derived from non-carbon based renewable sources, since the generation of electricity from carbon-based fuel combustion is only 30 to 45% energy efficient. Energy efficiency gains when using renewable electricity for heating applications (as in first category C1 and second category C2, discussed hereinabove) are smaller, but still significant. The net result is that less total energy will be used if renewable energy is used in place of carbon-based fuels (e.g., natural gas or other hydrocarbons).

TABLE 1

| Energy Efficiency of Unit Operations | | |
| --- | --- | --- |
| Use | Efficiency from Hydrocarbon Combustion | Efficiency from Electricity According to This Disclosure |
| C1: Direct Heating | up to 80-90% | 95+% |
| C2: Heating with Steam | up to 80-95% | 95+% |
| C3: Rotating Equipment | 25-40% | 90-95% |

According to this disclosure, non-carbon based energy, renewable energy, and/or electricity (e.g., from renewable and/or non-renewable sources) can be utilized rather than conventional energy sources in categories C1, C2, and/or C3 described hereinabove. In embodiments, electrification is utilized for a majority of or substantially all utilities. In embodiments, electrification is utilized for a majority of or substantially all unit operations. In embodiments, electrification is utilized for a majority of or substantially all utilities and unit operations. In embodiments, electrification is utilized for a majority of or substantially all process applications, engines, cooling and/or heating (e.g., electrically driven heat pumps, refrigeration, electrical heating), radiation, storage systems, or a combination thereof.

In embodiments, the non-carbon based and/or renewable energy source comprises wind, solar, geothermal, hydroelectric, nuclear, tide, wave, ocean thermal gradient power, pressure-retarded osmosis, or a combination thereof. In embodiments, the non-carbon based energy source comprises hydrogen. In embodiments, electricity for electrification as described herein is produced from such a renewable and/or non-carbon based energy source. In embodiments, some or all of the electricity is from a non-renewable and/or carbon-based source, such as, without limitation, combustion of hydrocarbons (e.g., renewable or non-renewable hydrocarbons), coal, or hydrogen derived from hydrocarbons (e.g., renewable or non-renewable hydrocarbons).

The majority of the $CO_2$ emitted from most chemical plants is a result of fossil fuel combustion to provide energy for the plant. An additional benefit of using renewable energy in chemical synthesis as per embodiments of this disclosure is that the amount of greenhouse gases emitted will be significantly (e.g., by greater than or equal to at least 5, 10, 20, 30, 40, 50, 60, 70, 80, 90, or 100%) reduced relative to an equivalent conventional chemical synthesis plant or method in which hydrocarbons and/or fossil fuel(s) may be combusted. The burning of hydrocarbons (e.g., natural gas, methane) to generate energy results in the production of carbon dioxide ($CO_2$); this production can be reduced or avoided by the use of renewable energy according to embodiments of this disclosure. In embodiments of this disclosure, the amount of $CO_2$ produced per ton of product produced is reduced to less than or equal to about 1.6, 1.5, 1.4, 1.3, 1.2, 1.1, 1.0, 0.75, 0.5, 0.30, 0.25, 0.2, 0.1, 0.05, or 0 tons $CO_2$ per ton chemical product (e.g., methanol). Furthermore, in embodiments of this disclosure, the use of renewable energy frees up these hydrocarbons (e.g., natural gas, methane) typically burned for fuel for use as a chemical feedstock (e.g., to make methanol), which is a higher value use.

The use of renewable electricity in the production of chemicals can also lead to operational advantages. For example, in embodiments, electric power can be utilized to provide a more accurate and tunable input of heat, for example to control the temperature profile along a reactor or to change the temperature of specific trays in a distillation column. In embodiments, the use of electric heating in a reaction section (e.g., in a pyrolysis reaction section) leads to better controlled decoking and/or faster decoking. Without limitation, other examples include the use of electric powered refrigeration units to increase the efficiency of separations, and the replacement of inefficient stand-by gas-fired boilers with quick-acting on-demand electrical heaters and steam generators and for other utility uses. The use of electricity may also allow for significant operational advantages during start-up or shut-down, or to respond to process variability. In general, electricity as an energy source can be applied in specific locations and in precise and tunable amounts with a rapid response to process changes, leading to a variety of advantages over the use of thermal/combustion energy.

The use of renewable electricity according to embodiments of this disclosure can also increase the energy efficiency of utilities that supply energy to more than one chemical plant (e.g., a methanol synthesis plant and a nearby ammonia synthesis plant or a methanol synthesis plant and a nearby olefin synthesis plant). For example, if the compressors in an air separation unit that provides oxygen and nitrogen to several different production facilities are powered with renewable electricity, significant energy gains can be achieved relative to supplying this power with steam derived from the combustion of natural gas.

Energy recovery may be provided, in embodiments, via high temperature heat pumps or vapor recompression. The plant may further comprise heat and/or energy storage, for example, for use when an intermittent energy source (IES) is utilized. In embodiments, waste heat can be upgraded to usable temperature levels via electrically driven heat pumps. In other embodiments, energy can be recovered as electricity when process stream pressures are reduced by using a power-generating turbine instead of a control valve. In other embodiments, energy can be recovered as electricity using thermoelectric devices.

The use of renewable electricity to replace natural gas or other hydrocarbons as a source of energy, according to embodiments of this disclosure, can be done as part of a retrofit of an existing chemical process (e.g., an existing methanol synthesis plant) or as an integral component of the design of a new chemical plant (e.g., a new methanol synthesis plant). In a retrofit, opportunities for using renewable energy can depend on elements of the existing design, such as the steam system; in a retrofit, careful examination of the entire energy balance and steam system will be required, as electrifying individual pieces of equipment without regard to these considerations may result in energy inefficiencies. In embodiments, as seen in Table 1, the highest efficiency gains are achieved by replacing steam drives for rotating equipment (e.g., in third category C3) with electric motors. However, differing objectives may lead to different choices in partial electrification; in embodiments, in some instances greater $CO_2$ reductions at the expense of smaller increases in energy efficiency may sometimes be realized by first replacing hydrocarbon-fired furnaces (e.g., in first category C1). In embodiments, if thermal energy and/or steam are obtained from more than one hydrocarbon source, the most advantageous operation can be achieved by eliminating the most expensive and/or polluting fuel sources first. How much renewable energy can be included and to what extent existing fuel consumption and carbon dioxide ($CO_2$) emissions can be decreased can vary depending on the application, and will be within the skill of those of skill in the art upon reading this disclosure.

In embodiments, planning for the use of renewable energy in the design of a grass-roots chemical facility (e.g., a grass-roots methanol synthesis plant) can allow for more significant opportunities for better energy efficiency and lower $CO_2$ emissions. In embodiments, powering all rotating equipment (e.g., in third category C3) with electricity is utilized to realize large gains in energy efficiency. In embodiments, substantially all (or a majority, or greater than 40, 50, 60, 70, 80, or 90%) electric heating (e.g., in first category C1 and/or second category C2) is utilized, and the inefficiencies due to the loss of heat in flue gas are substantially reduced or even avoided. In embodiments, the use of steam generated via the combustion of a fossil fuel (e.g., in second category C2) can be minimized or avoided altogether. In embodiments, a change in catalyst and/or a modification of reactor operating conditions is utilized to allow for less heat generation in a reactor and/or the production of fewer byproducts that are burned. In embodiments, a plant (e.g., methanol synthesis plant) design based on the use of renewable electricity allows for enhanced optimization of separations operations, since the relative costs of compression and refrigeration are changed via utilization of renewable electricity as per this disclosure. Such enhanced separations can, in embodiments, also allow for further capture of minor byproducts from vent streams, freeing these minor products up for further use as feedstocks or products. Furthermore, the use of low-cost electricity, according to embodiments of this disclosure, may allow for the introduction of novel technologies such as, without limitation, hybrid gas and electric heaters, variable speed compressor drives, distributed refrigeration, heat pumps, improved distillation columns, passive solar heating of fluids, precise control of reactor temperature profiles, new materials of construction, and quench or cooling using electrically refrigerated diluents. If the cost of electricity is sufficiently low, utilization of such electricity as taught herein may favor the introduction of new electrochemical processes. For new construction, it may be less capital intensive to drive processes electrically, due, for example, to the lack of a (e.g., plant-wide) steam distribution system.

According to embodiments of this disclosure, non-carbon based energy, renewable energy, and/or electricity (renewable, non-renewable, carbon-based, and/or non-carbon based electricity) can be used in the production of nearly every chemical, including but not limited to methanol, ammonia, olefins (e.g., ethylene, propylene), aromatics, glycols, and polymers. Non-carbon based energy, renewable energy, and/or electricity can also be used, in embodiments, in the preparation of feedstocks for chemicals and for fuels production, such as in methyl tert-butyl ether (MTBE) synthesis, cracking, isomerization, and reforming. In such embodiments, some (e.g., at least about 10, 20, 30, 40, or 50%), a majority (e.g., at least about 50, 60, 70, 80, 90, or 95%), or all (e.g., about 100%) of the heating throughout the plant/process or a section thereof can be provided by electrical heating and/or some (e.g., at least about 10, 20, 30, 40, or 50%), a majority (e.g., at least about 50, 60, 70, 80, 90, or 95%), or all (e.g., about 100%) of the cooling throughout the plant/process or a section thereof can be provided by electrical cooling as described hereinabove. Disclosed hereinbelow is the use of renewable energy, non-carbon based energy, and/or electricity in methanol synthesis applications.

The disclosures of U.S. Provisional Patent Application Nos. 62/792,612 and 62/792,615, entitled Use of Renewable Energy in Olefin Synthesis, U.S. Provisional Patent Application Nos. 62/792,617 and 62/792,619, entitled Use of Renewable Energy in Ammonia Synthesis, U.S. Provisional Patent Application Nos. 62/792,622 and 62/792,627, entitled Use of Renewable Energy in Methanol Synthesis, and U.S. Patent Application Nos. 62/792,631, 62/792,632, 62/792, 633, 62/792,634, and 62/792,635, entitled Use of Renewable Energy in the Production of Chemicals, which are being filed on Jan. 15, 2019, are hereby incorporated herein for purposes not contrary to this disclosure.

This disclosure describes a methanol synthesis plant for producing methanol, wherein the plant is configured such that a majority of the net energy required by one or more sections, units, or groups of like units or unit operations of the methanol synthesis plant is provided by non-carbon based energy ($E_{NC}$) from a non-carbon based energy source (e.g., not produced via the combustion of a carbon-based fuel such as a hydrocarbon), from renewable energy (e.g., from non-fossil fuel derived energy ($E_{NF}$) from a non-fossil fuel based energy source (e.g., not produced via the combustion of a fossil fuel such as coal or natural gas)), and/or from electricity. The $E_{NC}$ or $E_{NF}$ source may, in embodiments, comprise, primarily comprise, consist essentially of, or consist of electricity. The $E_{NC}$ or $E_{NF}$ source may, in embodiments, comprise, primarily comprise, consist essentially of, or consist of renewable electricity. In embodiments a portion (e.g., greater than or equal to about 5, 10, 20, 30, 40, 50),), a majority (e.g., greater than or equal to about 50, 60, 70, 80, 90, or 95%), or all (e.g., about 100%) of the net energy needed by the overall methanol synthesis plant, a section of the plant (e.g., a feed pretreating section, a synthesis gas (or 'syngas') production (e.g. reforming) section, a methanol synthesis section, and/or a methanol purification section), a group of like units (e.g., compressors, power providing units, heating units, reboilers, cooling units, refrigeration units, separators, reformers, methanol synthesis reactors, distillation/fractionation columns), or unit operations (e.g., compression, powering, heating operations, cooling operations, reforming operations, separations) of the plant, or a combination thereof is provided by electricity, renewable energy (e.g., non-fossil fuel derived energy ($E_{NF}$)), and/or non-carbon based energy ($E_{NC}$). In embodiments, electricity is provided from a renewable energy source, such as, without limitation, wind (e.g., via wind turbines), solar (e.g., photovoltaic (PV) panels or solar thermal), hydroelectric, wave, geothermal, nuclear, tide, biomass combustion with associated capture of $CO_2$ in replacement crops, or a combination thereof. In embodiments a portion (e.g., greater than or equal to about 5, 10, 20, 30, 40, 50), a majority (e.g., greater than or equal to about 50, 60, 70, 80, 90, or 95%), or all (e.g., about 100%) of the electricity, renewable energy (e.g., non-fossil fuel derived energy ($E_{NF}$)), or non-carbon based energy ($E_{NC}$) needed by the overall methanol synthesis plant, a section of the plant (e.g., a feed pretreating section, a syngas generation section, a methanol synthesis section, and/or a methanol purification section), a unit or a group of like units (e.g., compressors, power providing units, heating units, reboilers, cooling units, refrigeration units, reformers, methanol synthesis reactors, separators, distillation/fractionation columns) or unit operations (e.g., compressing, powering, separating, heating, cooling, reforming) of the methanol synthesis plant, or a combination thereof, and conventionally provided in a similar methanol synthesis plant via combustion of a fuel, a carbon-based fuel, and/or a fossil fuel and/or the use of steam (e.g., that was itself generated via the combustion of such a fuel) as an intermediate heat (and/or energy) transfer fluid, is provided without combusting a fuel, a carbon-base fuel, and/or a fossil fuel and/or without the use of steam generated by the combustion of such a fuel as an intermediate heat (and/or energy) transfer fluid. In embodiments, the net energy for the overall plant or one or more sections, units or groups of like units of the plant is provided by electricity from a renewable energy source. For example, in embodiments, heating is electrically provided via resistive heating or otherwise converting electrical energy into thermal and/or mechanical energy.

In embodiments, a methanol synthesis plant of this disclosure is configured such that a majority (e.g., greater than 50, 60, 70, 80, or 90%) of the net energy needed (e.g., in addition to heat exchange between process streams) for powering, heating, cooling, compressing, separating, or a combination thereof utilized via a feed pretreating system, one or more reformers, one or more methanol synthesis reactors, a methanol purification system, or a combination thereof, as described hereinbelow, is provided by electricity.

In embodiments, a methanol synthesis plant according to embodiments of this disclosure is a large plant having a production capacity for methanol of greater than or equal to about 200,000 tons per year, 1,000,000 tons per year, or 5,000,000 tons per year. At the larger sizes anticipated in this disclosure, the amount of energy provided by a non-carbon based energy source, a renewable energy source and/or electricity will be correspondingly large. In embodiments, a partially or completely electrified plant according to the methods of this disclosure will consume 20, 50, 100, 150, 200, 500, 750, or 1000 MW or more of electricity.

Although a specific embodiment of a methanol synthesis plant will be utilized to describe the electrification of a methanol synthesis plant, as disclosed herein, it is to be understood that numerous arrangements of units and a variety of methanol synthesis technologies utilizing a variety of feedstocks (e.g., natural gas, methane, LPG, naphtha, petcoke, coal, or a combination thereof) can be electrified as per this disclosure, as will be obvious to those of skill in the art upon reading the description herein. Although described at times hereinbelow with regard to the production of methanol via reforming of a feed comprising natural gas, methanol synthesis plants utilizing other technologies for the synthesis of methanol from a variety of feeds can be electrified as per this disclosure.

Figure 3:
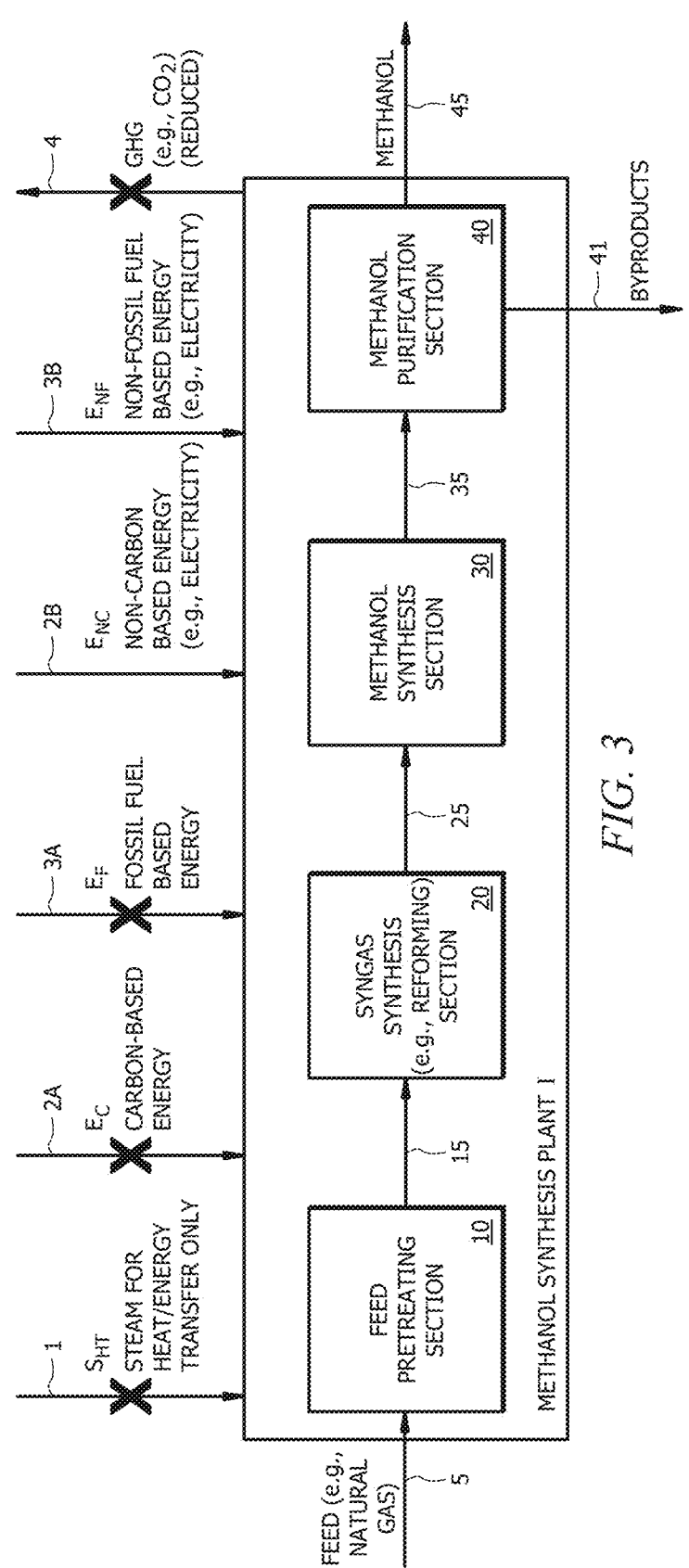
FIG. 3 shows a block flow diagram of a generalized methanol synthesis plant or process I, according to embodiments of this disclosure.

With reference to FIG. 3, which is a block flow diagram of a generalized methanol synthesis plant I, a methanol synthesis plant may be considered to include one or more of the following process sections for converting a feed stream 5 into a methanol product stream 45 (and optionally one or more byproduct streams 41): a feed pretreating section 10, a syngas synthesis section 20, a methanol synthesis section 30, a methanol purification section 40, or a combination thereof. Such sections will be described briefly in the next few paragraphs, and in more detail hereinbelow.

As indicated in the methanol synthesis block flow diagram of FIG. 3, a feed pretreating section 10 of a methanol synthesis plant is operable to prepare (e.g., remove undesirable components (e.g., sulfur) from, adjust temperature and/or pressure of a feed) a feed 5 for reforming, providing a pretreated feed 15. In applications, a methanol synthesis plant of this disclosure does not comprise a feed pretreating section. A syngas synthesis section 20 is operable to produce synthesis gas from feed 5 or pretreated feed 15 to produce a syngas synthesis product 25 comprising carbon monoxide (CO) and hydrogen ($H_2$). In embodiments, such as depicted in FIG. 2 and discussed further hereinbelow, syngas generation section 20 is a syngas synthesis section operable to carry out steam reforming of the feed (e.g., of a feed 5 or pretreated feed 15 comprising natural gas) to produce a reformer product comprising carbon monoxide (CO) and hydrogen ($H_2$). The syngas synthesis (or 'reformer') product 25 can further comprise carbon dioxide ($CO_2$), water, methane ($CH_4$), and/or impurities. A methanol synthesis section 30 is operable to produce methanol from the syngas synthesis product 25 and thus provide a crude methanol stream 35. A methanol purification section 40 is operable to separate a purified methanol product 45 and byproducts 41 from the crude methanol stream 35.

As depicted in FIG. 3 and mentioned above, energy (E) input to or within the methanol synthesis plant or one or more sections or groups of units, like units, or unit operations thereof (that may conventionally be provided via a carbon based energy ($E_C$) 2A from a carbon based energy source, a fossil fuel derived energy ($E_F$) 3A from a fossil fuel-based energy source, or via the use of steam (e.g., steam generated for this purpose using energy derived from a carbon or fossil fuel based energy source) solely or primarily as a heat or energy transfer medium ($S_{HT}$) 1), may be partially or completely replaced by non-carbon based energy ($E_{NC}$) 2B from a non-carbon based energy source, renewable/non-fossil fuel based energy ($E_{NF}$) 3B from a renewable energy source, and/or electricity (e.g., electricity and/or renewable electricity). The carbon based energy ($E_C$) 2A, the fossil fuel derived energy ($E_F$) 3A, or both can be partially or completely replaced by electricity. The electricity may be derived from a non-carbon based fuel, a renewable fuel, a renewable energy source, or a combination thereof, in embodiments. A benefit derived via the herein disclosed system and method may be a reduction in the greenhouse gas (GHG) emissions 4 from the methanol synthesis plant or process. The above-noted elimination or reduction of the steam system may also result in lower capital and operating costs, in embodiments.

According to this disclosure, when cooling process streams, as much heat as possible should be used to heat other process streams. However, below a certain temperature, further heat transfer is no longer effective or useful, and blowers, cooling water, and/or refrigeration (which require an energy input for heat removal) are utilized. In such embodiments, for example, heat exchangers, refrigeration units, or a combination thereof for altering the temperature of process streams may be powered electrically. In embodiments, steam is not utilized solely as an intermediate heat and/or energy transfer stream, and the plant or section(s) thereof do not comprise an elaborate steam system such as conventionally employed for energy transfer. In embodiments, steam is used as a heat transfer fluid and is not used to do mechanical work, for example to drive a pump or compressor. In embodiments, heating is provided via resistive heating. In embodiments, heating is provided via inductive heating.

Figure 4:
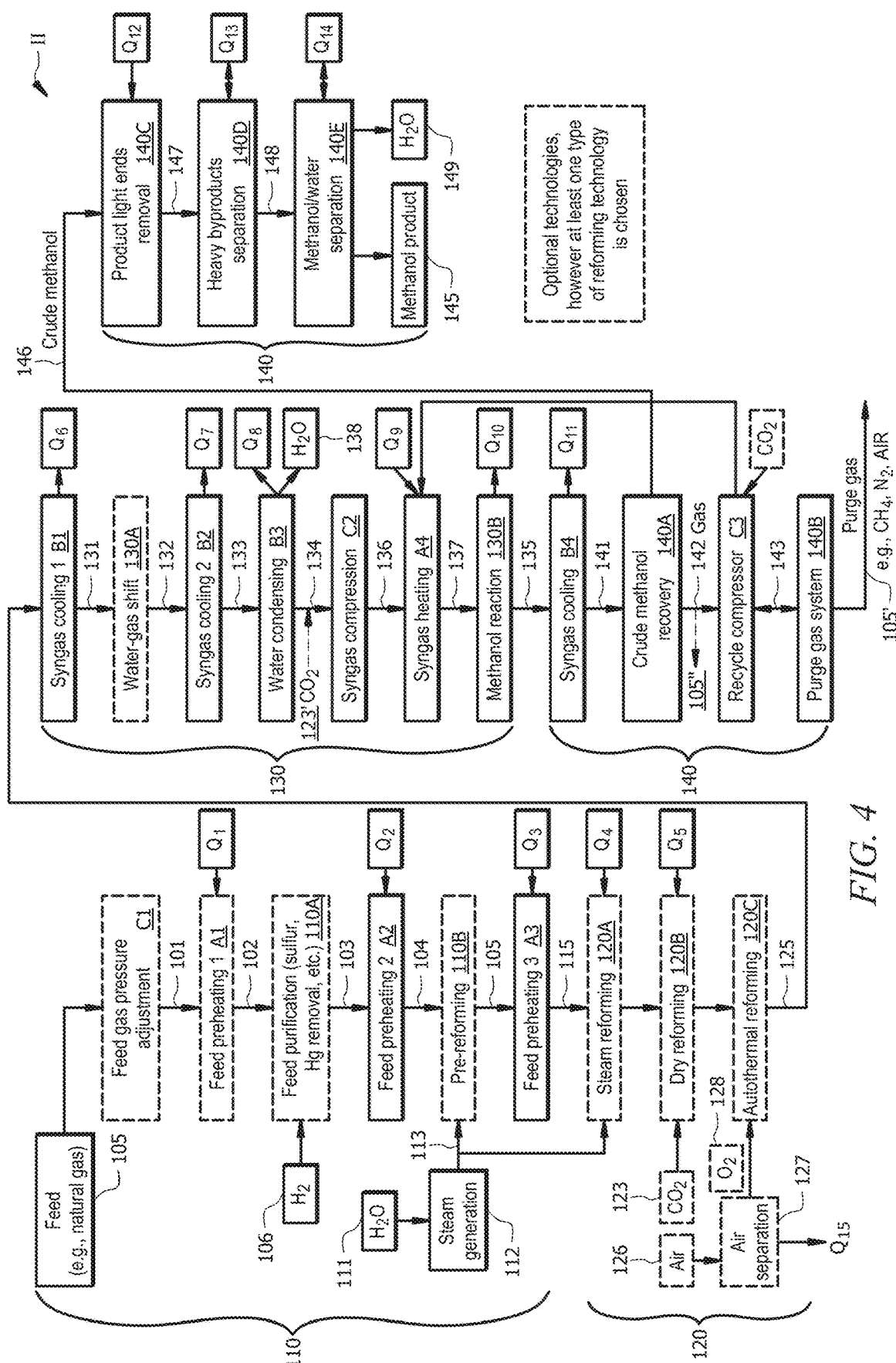
FIG. 4 shows a block flow diagram of an exemplary methanol synthesis plant or process II, according to embodiments of this disclosure.

Although not intending to be limited by the examples provided herein, a description of some of the ways a methanol synthesis plant can be electrified according to embodiments of this disclosure will now be provided with reference to the exemplary methanol synthesis block flow diagram of methanol synthesis plant II of FIG. 4. The steps, sections, groups of units or unit operations described may be present or operated in any suitable order, one or more of the steps, sections, units, or unit operations may be absent, duplicated, replaced by a different step, section, unit, or unit operation, and additional steps, sections, units, or unit operations not described herein may be employed, in various embodiments. Additionally, although a step (e.g., syngas cooling B1) is noted as being in a particular section (e.g., in methanol synthesis section 30/130), the step could also be considered a part of another section (e.g., syngas synthesis (or 'reforming') section 20/120).

As noted hereinabove with reference to the embodiment of FIGS. 3 and 4, in embodiments, a methanol synthesis plant of this disclosure comprises a feed pretreating section 10/110. Such a feed pretreating section 10/110 can be operable to remove one or more components such as, without limitation, sulfur and/or mercury, from a feed (e.g., a natural gas feed), adjust the pressure of the feed to a desired operating pressure, adjust the temperature of the feed to a desired operating temperature, pre-reform the feed, or a combination thereof.

As noted hereinabove, in embodiments, the pretreating section 10/110 is operable to provide the feed at a desired operating pressure for the downstream syngas synthesis section 20/120. In the exemplary methanol synthesis plant II of FIG. 4, feed pretreating section 110 comprises apparatus for feed gas pressure adjustment C1, operable to adjust the pressure of a feed introduced thereto via natural gas feed stream 105. One or more compressors may be utilized to increase the pressure of the feed stream 105. In other embodiments, if the delivery pressure of the feed is higher than that required for the process, the pressure is lowered through a power-generating turbine such that the energy of the excess pressure is recovered, e.g. as electrical energy.

As noted hereinabove, in embodiments, the pretreating section 10/110 is operable to provide the feed at a desired operating temperature. For example, in the exemplary methanol synthesis plant II of FIG. 4, feed pretreating section 110 comprises first feed preheating A1, second feed preheating A2, and third feed preheating A3, operable to adjust the temperature of a feed introduced thereto to a desired downstream temperature. In the embodiment of FIG. 4, first feed preheating A1 is configured to increase the temperature of the feed in stream 101 (via a first heat input Q1) to a desired temperature for feed purification at 110A (described below) in stream 102; second feed preheating A2 is configured to increase the temperature of the feed in stream 103 from feed purification 110A (via a second heat input Q2) to a desired temperature for feed pre-reforming at 110B (described below) in stream 104; third feed preheating A3 is configured to increase the temperature of the feed in stream 105 from feed pre-reforming (via a third heat input Q3) to a desired temperature in feed stream 115 for downstream reforming in downstream syngas synthesis section 120.

In embodiments, the heat obtained from cooling the reformer products (e.g., Q6, Q7, and/or Q8 discussed further hereinbelow) is used to preheat the feed (e.g., used to provide a first portion of the heat Q1, Q2, and/or Q3). In embodiments, a remainder of the heat needed for Q1, Q2, and/or Q3 is provided by resistive heating, superheated steam, internal oxidation obtained by adding a small amount of oxygen or air, or a combination thereof.

As noted hereinabove, in embodiments, the pretreating section 10/110 is operable to remove one or more components from a feed stream prior to downstream synthesis gas production in downstream syngas synthesis (e.g., reforming) section 20/120. For example, impurities such as sulfur compounds, carbon dioxide, nitrogen, mercury, or a combination thereof may be removed from a feed stream (e.g., a natural gas feed stream) by pretreating section 10/110. For example, if the feed comprises sulfur, sulfur compounds may be removed because sulfur deactivates the catalyst(s) used in subsequent steps. Sulfur removal can utilize catalytic hydrodesulfurization (HDS) to convert sulfur compounds in the feedstocks to gaseous hydrogen sulfide via the Equation (1):

$$H_2 + RSH \rightarrow RH + H_2S(gas). \tag{1}$$

The gaseous hydrogen sulfide can then be adsorbed and removed by passing it through beds of, for example, zinc oxide, where it is converted to solid zinc sulfide via the Equation (2):

$$H_2S + ZnO \rightarrow ZnS + H_2O. \tag{2}$$

For example, in the exemplary methanol synthesis plant II of FIG. 4, feed pretreating section 110 comprises feed purification (e.g., sulfur removal, Hg removal, etc.) 110A. Hydrogen stream 106 may be introduced into feed purification apparatus of feed purification (e.g., sulfur removal, Hg removal, etc.) 110A. Feed purification apparatus utilized in 110A can be any suitable contaminant/poison removal apparatus known to those of skill in the art.

As noted hereinabove, in embodiments, the pretreating section 10/110 is operable to pre-reform a feed. For example, in the exemplary methanol synthesis plant II of FIG. 4, feed pretreating section 110 comprises feed pre-reforming 110B. Pre-reforming apparatus may be operable to remove higher hydrocarbons that may foul the main reformer. Feed pre-reforming apparatus utilized in 110B can be any suitable pre-reforming apparatus known to those of skill in the art.

According to embodiments of this disclosure, feed pre-treating can be effected with a reduced usage of non-carbon based energy, non-fossil based energy, the use of renewable energy, or the use of electricity (e.g., electricity from renewable and/or non-renewable source(s)). For example: compressors of the pretreating section (e.g., feed gas pressure adjustment C1) can be operated with electric motors rather than gas or steam driven turbines, feed preheating A1, A2 and/or A3 can be effected with resistive heating, steam produced at steam generation 112 for pre-reforming (and/or downstream reforming or other syngas synthesis described below) can be generated electrically, feed purification apparatus at 110A and/or pre-reforming apparatus at 110B may be operated electrically, or a combination thereof. In embodiments, pretreatment beds can be regenerated using heat, steam, or other gases wherein the energy is supplied electrically. In embodiments, a feed preheater for a hydrodesulfurization reactor can use electrically powered heating. In embodiments, vapor compression heat pumps may be used to heat the feed and/or thermoelectric heaters and coolers may be used to heat or cool the feed. For example, steam generated by an electrode boiler, which converts over 99% of the input electrical energy into making steam, can be utilized to provide higher energy efficiency than a conventional hydrocarbon (or fossil fuel) fired steam boiler.

In embodiments, feed preheating can be done by electric resistive heating elements that can be arranged internally to a process conduit, within a heat transfer element sheath, and/or externally to the process conduit while heating the feed through the conduit. Heat from resistive heating elements may flow through heat transfer equipment (e.g. metal surfaces, fins, tubes, etc.) heat transfer gases, vapors, fluids, solids, plasmas, and/or other media and may transfer to the process in conductive, convective and/or radiative form. Ohmic resistive heating or inductive heating of the process conduits or equipment can be utilized, in embodiments. In embodiments, mechanical heating can be utilized. In embodiments, heating by electromagnetic waves, either by absorption of the process fluid or by absorption by another media that subsequently transfers heat to the process fluid can be utilized. In embodiments, vapor compression heat pumps, and/or thermoelectric heaters and/or coolers can be utilized. In embodiments, steam is generated using an electrode boiler or a resistive immersion heater. In embodiments, preheating is effected by the injection of a hot process fluid. In embodiments, this hot process fluid comprises steam. In embodiments, the steam is heated electrically. In embodiments, the steam is obtained from the oxidation of hydrogen or from fuel cell exhaust.

A methanol synthesis plant according to this disclosure comprises a syngas generation section operable to reform the hydrocarbon feed to produce hydrogen and carbon monoxide (e.g., synthesis gas or 'syngas'). Although described with reference to the embodiment of FIG. 4, which comprises a syngas synthesis section as syngas generation section 120, synthesis gas for the methanol synthesis may also or additionally be produced via partial oxidation (e.g. methane partial oxidation), and/or gasification (e.g. coal gasification), and such is intended to be within the scope of this disclosure.

Syngas synthesis section 20/120 can be or can include a reforming section, a partial oxidation section, a gasification section, or a combination thereof. In embodiments, such as the embodiment of FIG. 4, syngas synthesis section 20/120 comprises reforming. In the embodiment of FIG. 4, syngas synthesis section 120 can include steam methane reforming 120A, dry reforming 120B, autothermal reforming 120C, or a combination thereof. Optional technologies (not shown) include, without limitation, mixed reforming with steam, oxygen, and/or carbon dioxide. In embodiments, a reforming syngas synthesis section 120 comprises a steam methane reformer or reactor, a partial oxidation reformer or reactor, an autothermal reforming reactor, a dry reforming reactor, or a combination thereof. As indicated in the embodiment of FIG. 4, a heat input Q4 may be utilized to maintain a desired steam methane reforming temperature at 120A and/or a heat input Q5 may be utilized to maintain a desired dry reforming temperature at 120B. Carbon dioxide stream 123 may be utilized for dry reforming 120B and/or oxygen stream 128 may be utilized for autothermal reforming 120C. An air separation unit 127 may be utilized to provide oxygen stream 128 from air stream 126 for autothermal reforming 120C. Heat removal Q15 can be utilized to effect air separation in air separation unit(s) 127, for example cryogenic air separation unit(s), in embodiments. Steam stream 113 may be produced from water in water stream 111 via steam generation apparatus 112. As depicted in FIG. 4, the steam 113 can be utilized in a pre-reformer (when present) and a reformer (e.g., a steam methane reformer 120A).

A reforming section as syngas synthesis section 20/120 can be operable to effect catalytic steam reforming of the (e.g., sulfur-free) methane feed to form hydrogen plus carbon monoxide via Equation (3):

$$CH_4 + H_2O \rightleftharpoons CO + 3H_2. \tag{3}$$

The water gas shift reaction shown in Equation (4) also occurs:

$$CO + H_2O \rightleftharpoons CO_2 + H_2. \tag{4}$$

Generally, at equilibrium, the reactions of Equations (3) and (4) can be combined to provide the overall reaction of Equation (5):

$$CH_4 + 2H_2O \rightleftharpoons CO_2 + 4H_2. \tag{5}$$

For example, syngas synthesis section 120 of the embodiment of FIG. 4 comprises steam methane reforming at 120A, whereby methane in methane feed 115 and steam in line 113 are combined and then fed to a steam methane reforming furnace of steam methane reforming 120A where the methane is partially converted to carbon monoxide and hydrogen via Equation (3). In embodiments, steam methane reforming (SMR) is effected at a temperature in a range of from about 500° C. to about 1000° C. (about 930° F. to 1830° F.) and a pressure in a range of from about 8 to about 35 bars. The steam methane reforming (SMR) reaction is endothermic and the heat of reaction is conventionally provided by burning methane and/or process purge gases at furnace burners to provide heat input, indicated as Q4. As described further hereinbelow, according to embodiments of this disclosure, the heat input Q4 is provided via a renewable energy source and/or electricity. The renewable energy source can comprise electricity from a renewable energy source (such as wind or solar energy, etc.). Thus, according to embodiments of this disclosure, a steam methane reforming apparatus 120A is not heated via combustion of a dedicated fuel (e.g., is not produced via combustion of a carbon-based and/or fossil-based fuel in a furnace to provide heat for the reactions). Carbon dioxide produced via Equation (4) or (5) can be converted to methanol and thus not result in emissions conventionally seen when a dedicated fuel is combusted in a furnace to provide heat for the reactions and concomitantly produces a flue gas comprising $CO_2$.

In embodiments, a system or method of methanol synthesis according to this disclosure results in the production of less than or equal to about 2, 1.5, 1, 0.5, 0.1, or 0 (e.g., no) tons of a combustion flue gas produced via combustion of a fuel (e.g., a carbon-based fuel, a fossil fuel, or a combination thereof) per ton of methanol produced. In embodiments of this disclosure, the amount of $CO_2$ produced per ton of methanol produced is reduced to 0.30, 0.25, 0.2, 0.1, 0.05, or 0 tons $CO_2$ per ton methanol. In embodiments, no flue gas is produced, for example, within the syngas synthesis section, one or more sections or all the sections of the methanol synthesis plant of this disclosure.

In embodiments, the steam methane reformer(s) is (are) heated electrically. In embodiments, the steam reformer(s) are heated with resistive or inductive heating. In embodiments, the steam reformer(s) are heated by means of radiative panels that are heated electrically (e.g., via resistive heating, inductive heating, ohmic heating, or the like.)

In embodiments, a 2-stage reformer is utilized, and oxygen 128 is added to the partially converted mixture from the first stage reformer wherein it combusts with methane to generate carbon oxides and heat via partial oxidation. For example, in embodiments, the temperature rises to a temperature in a range of from about 1200 to 1250° C. at an inlet of an autothermal catalyst bed and to about 700 to 900° C. at an exit of the autothermal catalyst bed). The combination of steam reforming and partial oxidation can be utilized, in embodiments, to control the composition of the resultant synthesis gas.

In embodiments, $CO_2$ stream 123 is utilized to add some $CO_2$ into the process gas stream either ahead of a syngas synthesis reactor (e.g., a steam reformer) or downstream of a syngas synthesis reactor (e.g., a steam reformer). This can allow a larger fraction of the hydrogen produced by the SMR to be incorporated into methanol molecules (e.g., by reaction with $CO_2$). In embodiments, $CO_2$ is introduced upstream of one or more methanol synthesis reactors of methanol synthesis section 30/130 (described further hereinbelow) to consume extra hydrogen, balance the heat in the one or more methanol synthesis reactors (e.g., make it less exothermic so that there is less required heat removal Q10), and allow for the electric conversion of $CO_2$ to methanol. Alternatively or additionally, $CO_2$ can be introduced, in embodiments, to a reverse water gas shift (WGS) reactor (e.g., to WGS 130A of methanol synthesis section 30/130, further described hereinbelow) to provide for endothermic and low-temperature WGS and/or an easy and low-temperature sink for electricity and/or excess low-grade heat from cooling product streams.

Syngas synthesis section 20/120 can comprise dry reforming. In dry reforming, reaction of methane and carbon dioxide produces synthesis gas in a process called dry reforming as no steam or less than normal quanitites of steam utilized for Steam Methane Reforming is employed. Dry reforming proceeds as per Equation (6):

$$CH_4 + CO_2 \rightleftharpoons 2CO + 2H_2 \quad \Delta H_{298K} = 59.1 \text{ kcal/mol}. \tag{6}$$

The reaction of Eq. (6) is more endothermic than steam methane reforming and produces a gas with significant hydrogen deficit for methanol synthesis. While this is a disadvantage for methanol synthesis, dry reforming may be utilized, in embodiments. In embodiments, dry reforming is utilized in conjunction with steam reforming.

The production of synthesis gas is generally strongly endothermic and requires the addition of thermal energy (provided as heat Q). As noted above, conventionally, a fuel (e.g., natural gas, methane, purge gas from the methanol synthesis section) is burned to provide heat (e.g., Q4 and/or Q5) needed to attain a desired reforming temperature and provide the necessary heat of reaction. In embodiments of this disclosure, a desired reforming temperature is attained without burning a fuel externally in a furnace. In embodiments of this disclosure, a desired reforming temperature is attained without burning a carbon-based fuel. In embodiments, a desired reforming temperature is achieved by the injection of steam produced electrically or from the combustion of hydrogen. Desirably, no fossil-based fuel, no carbon based fuel (e.g., methane, or natural gas), and/or no hydrogen is burned as a dedicated fuel in embodiments of this disclosure, as such materials conventionally burned as a fuel can then be utilized as a feed to produce additional methanol product according to embodiments of this disclosure.

In embodiments, syngas synthesis section 20/120 is configured for the production of carbon dioxide ($CO_2$) by combustion internally to the process to add heat to the syngas generation section and reduce heat generation in the one or more methanol synthesis reactors of a methanol synthesis section 30/130, described further hereinbelow. In embodiments, such carbon dioxide is produced via combustion of a renewable (e.g., a non-fossil) fuel.

In embodiments, the syngas synthesis section 20/120 is configured to supply syngas and/or purified hydrogen as a product. This can be done, for example, by cleaning contaminants by absorbing them in an absorbing solvent and then regenerating the solvent by electric heating. Alternately, pressure-swing or temperature swing adsorption could be employed in hydrogen separation and purification. Alternatively, membrane separations with electrically powered recycle or charge compressors could be used for the separation. Cryogenic distillation that is electrically driven could be employed in the purification. In other embodiments, the syngas or purified hydrogen product is an intermediate stream that is integrated with another chemical process that is the consumer of the hydrogen or syngas. In embodiments, the amount of hydrogen produced is increased by purposefully manipulating various process variables, e.g., steam to carbon ratio or oxygen to carbon ratio.

In embodiments, reforming can be effected with a reduced usage of non-carbon based energy ($E_{NC}$), the use of renewable energy (e.g., non-fossil fuel based energy ($E_{NF}$)), or the use in electricity (e.g., electricity from renewable source(s)). For example: compressors and pumps of the syngas synthesis section (such as a compressor or pump for introducing steam 113, carbon dioxide 123, or oxygen 128) can be operated with electric motors or otherwise electrically-driven rather than via gas or steam driven turbines, the heat input Q4 or Q5 required to attain a desired reforming temperature (in a steam methane reformer 120A or a dry reformer 120B) can be electrically provided, or a combination thereof.

In embodiments, $H_2O$ (e.g., water stream 111, $CO_2$ (e.g., $CO_2$ stream 123), $O_2$ (e.g., $O_2$ stream 128), or a combination thereof can be preheated electrically before introduction. In embodiments, steam for reforming is generated using an electrode boiler. In embodiments, $H_2O$ and/or $CO_2$ (e.g., in water stream 111 and/or $CO_2$ stream 123), can be superheated electrically to raise the temperature of the process stream when they are introduced. Alternatively or additionally, in embodiments, the heat (e.g., Q3, Q4, and/or Q5) for the reforming reaction of a syngas synthesis section 20/120 can be provided electrically. In embodiments, reforming heat (e.g., Q3, Q4, and/or Q5) can be provided by electric resistive heating elements that can be arranged internally to a process conduit, within a heat transfer element sheath, and/or externally to the process conduit while heating the process through the conduit. Heat from resistive heating elements may flow through heat transfer equipment (e.g. metal surfaces, fins, tubes, etc.) heat transfer gases, vapors, fluids, solids, plasmas, and/or other media and may transfer to the process in conductive, convective or radiative form. Ohmic resistive heating or inductive heating of the process conduits or equipment may be utilized, in embodiments. In embodiments, mechanical heating can be utilized. Heating by electromagnetic waves, either by absorption of the process fluid or by absorption by another media that subsequently transfers heat to the process fluid may be utilized, in embodiments.

In embodiments, thermoelectric devices can be utilized to heat the reaction of syngas synthesis section 20/120 (e.g., steam reforming section 120A, dry reforming section 120B, and/or autothermal reforming section 120C) while providing cooling for the hot syngas. Multi-stage thermoelectric devices may be used to provide heat to the reaction coming from the downstream methanol synthesis reaction of methanol synthesis section 30/130 or another part of the process. Thermoelectric devices may be used to generate electricity while cooling the oxidation reaction (e.g., of a partial oxidation syngas synthesis section 20/120) or the reformer effluent (of a reforming syngas synthesis section 20/120). In cases where electric heating is used, one resulting advantage can be enhanced heat distribution and more heat uniformity. For example the tube metal temperature is a design limitation of a heater from a conventional combustion source, with the hottest part being located near the flame. By eliminating the flame, the design can be of an overall higher temperature on the process side, with more uniformity, potentially leading to higher conversions in the reformer and thus higher overall conversion. In embodiments, steam supplied to the syngas synthesis section 20/120 can be generated electrically. In embodiments, steam is used as a reactant and/or for dilution in syngas synthesis section 20/120, and the steam used for reactant and/or dilution is generated using electricity. In embodiments, oxygen supplied to the oxidative part of a reforming section of a syngas synthesis section 20/120 can be made by air separation powered by electricity. In embodiments, carbon dioxide supplied to dry or mixed reforming can be recovered and/or supplied by electrically heated and/or powered equipment.

In embodiments, at least 5%, 10%, 20%, 30%, 40%, 50%, 60%, 70%, 80%, 90%, a majority, or all of the air separation units (ASUs) of syngas synthesis section 20/120 or elsewhere in a methanol synthesis plant of this disclosure are electrically powered.

As noted above, a methanol synthesis plant of this disclosure can comprise a methanol synthesis section 30/130. After the reforming is complete, the syngas stream can be partially cooled, optionally fed to a water-gas shift reactor where additional hydrogen is formed by shifting water and carbon monoxide to produce additional hydrogen and carbon dioxide. The shifted stream can be cooled to near ambient temperature and much of the water condensed out to provide a largely dry gas called dry gas for the methanol synthesis. The pressure of the largely dry gas can be increased to a desired methanol synthesis reaction pressure, which can be, for example, from about 1000 to 3000 psia, via one or more compressors. Thus, with reference to FIG. 4, in embodiments, the methanol synthesis section 30/130 can comprise cooling the syngas produced in the syngas synthesis section 20/120 at syngas cooling B1 and/or B2, water gas shifting the synthesis gas at 130A, condensing water at cooling B3, compressing the syngas at C2, heating the syngas at A4, forming methanol from the syngas at methanol reaction 130B, or a combination thereof. Methanol synthesis section 30/130 can thus comprise cooling apparatus to effect cooling B1/B2/B3 operable to remove heat from the syngas; water gas shift apparatus operable to subject the syngas to water-gas shifting at 130A, compression apparatus (also referred to herein as a syngas compressor) operable to compress the dry syngas at C2; heating apparatus operable to heat the syngas at syngas heating A4 for introduction into methanol synthesis at 130B; and/or methanol synthesis apparatus to carry out methanol synthesis at 130B.

As noted above, a methanol synthesis section 30/130 of this disclosure can comprise synthesis gas cooling B1/B2/B3. For example, after reforming in syngas synthesis section 20/120, the synthesis gas can be cooled. For example first syngas cooling B1 may be operable for heat removal (indicated at Q6) upstream of a water-gas shift 130A, second syngas cooling B2 may be operable for heat removal (indicated at Q7) downstream of a water-gas shift 130A, water condensing or third syngas cooling B3 may be operable for heat removal (indicated at Q8) and removing water 138 from the syngas upstream of methanol synthesis at 130B. As noted above, the methanol synthesis section 30/130 can comprise a water removal, "water condensing" or third cooling apparatus B3. In the embodiment of FIG. 4, the optionally shifted syngas stream 132 stream is cooled in second syngas cooling B2 and the water 138 is condensed out (with heat removal indicated at Q8) at water condensing B3, to produce a dry gas stream 134.

As noted below, in embodiments, a majority, greater than 20, 30, 40, 50, 60, 70, 80, or 90%, or substantially all of the cooling B1/B2/B3 is powered by a non-carbon based energy source, e.g., electricity from a renewable energy source and/or cooling via heat exchange with the process stream in another section of the plant. For example, cooling can be at least partly achieved, in embodiments, by heat exchanging with the compressed syngas stream 136 (described hereinbelow) exiting syngas compression (e.g., using Q7 to provide some or all of the energy Q9). In embodiments, some or all of the heat recovered in cooling B1/B2/B3 is used in feed preheating A1/A2/A3. In embodiments, this is done using one or more feed/effluent heat exchangers.

As noted above, a methanol synthesis section 30/130 of this disclosure can comprise synthesis gas shifting 130A. For example, after reforming is complete, the reformer product stream 25/125 can be subjected to water gas shifting in a shift conversion section 130A to produce additional hydrogen via the water gas shift (WGS) reaction of Equation (4) above.

Desirably, and without limitation, reforming and/or shifting are operated, in embodiments, to provide a synthesis gas (e.g., for feeding to the methanol synthesis reactors of methanol synthesis 130B) that has a ratio of hydrogen to carbon monoxide ($H_2/CO$) of about 2 and a $(H_2-CO_2)/(CO+CO_2)$ ratio, or stoichiometric number, equal to or slightly greater than 2. The shifting can be effected via any suitable methods known in the art, in embodiments. For example, shifting can comprise high temperature shift, low temperature shift, or both. In the embodiment of FIG. 4, the reformer product in reformer product stream 125 is partially cooled at first cooling step or unit(s) B1 (with heat removal indicated by Q6) to produce a cooled reformer product indicated by stream 131. Cooled reformer stream 131 is introduced into shift reactor(s) at 130A where additional hydrogen ($H_2$) is formed by shifting $H_2O$ and CO to produce $CO_2$ and additional hydrogen via the water gas shift (WGS) reaction of Equation (4) above to provide shifted stream 132. Cooling B2 of the shifted stream 132 may be performed in second cooling step or unit(s) B2 (with heat removal indicated by Q7) and water removal via cooling B3 (with heat removal indicated by Q8), whereby the stream is further cooled to provide cooled, shifted streams 133 and 134, respectively. Without limitation, a methanol synthesis plant of this disclosure may comprise both high temperature shift and low temperature shift at 130A because low temperature is needed to drive the reaction to near completion, but the reaction proceeds faster at high temperature.

In embodiments, a shift reactor is utilized downstream of the methanol synthesis reaction, for example, downstream of crude methanol recovery 140A and upstream of purge gas system 140B. In such embodiments, the shift reactor can be utilized to shift a portion of the gas stream 142 prior to introduction, for example, into a hydrogen purification apparatus for separation and recycle of hydrogen to methanol synthesis at 130B. In such embodiments, a portion of the gas stream 142 can be recycled to methanol synthesis at 130B (e.g., via the hydrogen purification apparatus) without shifting. Similarly, at least a portion of a shifted stream from an upstream shift reactor (e.g., a portion of shifted syngas stream 133 from water gas shifting at 130A) can be introduced into a hydrogen purification apparatus prior to introduction into methanol synthesis at 130B. In embodiments, a portion of the syngas can be diverted for the isolation of a purified hydrogen product.

As noted above, a methanol synthesis section 30/130 of this disclosure can comprise syngas compression C2. For example, following water removal via cooling B3, the dry syngas is compressed to provide a compressed stream 136 prior to methanol synthesis at 130B. As noted herein, compression of the dry syngas can be effected, in embodiments, without the use of a gas and/or steam (wherein the steam is produced via combustion of hydrocarbon(s)) turbine, in embodiments. For example, in embodiments, such as for example a retrofit application, an electrically-driven compressor or electric motor or a steam turbine operated with electrically-produced steam may be utilized to compress the dry syngas prior to methanol synthesis at 130B. As noted above, the methanol synthesis section 30/130 can comprise syngas compression C2. For example, in the embodiment of FIG. 4, the dry gas stream 134 is introduced to the methanol synthesis reaction 130B via compression C2 with one or more compressors. Compression C2 can raise the pressure to about 1000 to about 3000 psia in compressed syngas stream 136, in embodiments.

As noted above, a methanol synthesis section 30/130 of this disclosure can comprise synthesis gas heating A4.

Syngas heating may be utilized to heat the dry, compressed syngas stream 136 to a desired methanol synthesis reaction temperature in heated syngas feed 137. In embodiments, the desired methanol synthesis reaction temperature can be in a range of from about 150° C. to 260° C., depending on the design of the methanol synthesis reactor.

As per this disclosure, a majority, greater than 20, 30, 40, 50, 60, 70, 80, or 90%, or substantially all of the heating of the compressed stream 135 via syngas heating A4 (and heat input indicated at Q9) may be effected electrically and/or otherwise does not require fuels combustion (e.g. via heat exchange with another process gas stream, such as, without limitation, cooled, shifted syngas stream 133), in embodiments.

As noted above, a methanol synthesis section 30/130 of this disclosure comprises methanol synthesis 130B. Thus, a methanol synthesis plant of this disclosure comprises methanol synthesis apparatus for carrying out the methanol synthesis 130B. The methanol synthesis section 30/130 can comprise one or more methanol synthesis reactors or catalyst beds for carrying out the methanol synthesis 130B. The number and placement of methanol synthesis reactors is generally known to those skilled in the art. For example a methanol synthesis reactor may be 1-pass methanol synthesis reactor, downstream of syngas compression and with a second compressor for recycle after crude methanol recovery (as in the embodiment of FIG. 4), a 1-pass methanol synthesis reactor followed by a methanol synthesis reactor with recycle, 2 methanol synthesis reactors in series within the syngas recycle loop, or any of a variety of other configurations for methanol synthesis known to those of skill in the art.

The methanol synthesis involves the following three equations, Eqs. (7)-(9):

$$CO + 2H_2 \rightleftharpoons CH_3OH \quad \Delta H^\circ_{500K} = -23.4 \ \text{kcal/mol} \tag{7}$$

$$CO_2 + 3H_2 \rightleftharpoons CH_3OH + H_2O \quad \Delta H^\circ_{500K} = -13.9 \ \text{kcal/mol} \tag{8}$$

$$\text{Reverse } WGS \ CO_2 + H_2 \rightleftharpoons CO + H_2O \quad \Delta H^\circ_{500K} = 9.5 \ \text{kcal/mol} \tag{9}$$

In the methanol synthesis, CO, $CO_2$, and $H_2$ in the syngas feed in stream 137 react to produce methanol via Equations (7) and (8). The reaction may be carried out, for example, at about 235° C. over a copper or zirconium containing catalyst. In embodiments, a mixture of copper and zinc oxides, supported on alumina, is utilized as catalyst. The reaction is exothermic (with heat removal indicated at Q10) and conversion is equilibrium limited. Heat removal can be integrated into the reactor design, for example by interstage cooling between multiple reactors and/or catalyst beds within the same reactor, through water cooling, or through the injection of cold gas including syngas. The water-gas shift reaction (Eq. (8)) also takes place over the catalyst. As the Equations (7), (8), and (9) are reversible, it is important to control process conditions regarding temperature, pressure, and synthesis gas mixture. Many reactor designs have been implemented, and the main reactor design differences are in how the reaction temperature is controlled. As per this disclosure, any suitable methanol synthesis technology may be utilized, as long as the operation follows the energy constraints provided herein. For example, in embodiments, a methanol synthesis reactor is operated with cooling to maintain a desired methanol synthesis temperature effected electrically. Electrically controlling the reactor temperature, as per this disclosure, may enable improved temperature control, in embodiments. For example, in embodiments a combination of heating and cooling techniques may be used for the methanol synthesis in methanol synthesis section 30/130. In embodiments, an electric heater is used to heat the syngas to the methanol synthesis reaction temperature. In embodiments, a vapor compression heat pump is used to heat the syngas to the methanol synthesis reaction temperature. In embodiments, a heat pump (vapor compression, chemical, absorption, or adsorption) is used to cool the methanol synthesis reactor. In embodiments a thermoelectric device is used to heat, cool, or simultaneously heat part of the reaction and cool another part of the reaction. In embodiments the heat of the methanol synthesis reaction is removed by heating water to make steam, by heating another heat transfer fluid, and/or by heat exchange with a process gas or gaseous heat transfer media. For example, in embodiments, heat produced at Q10 and/or Q11 may be utilized to provide some or all of the heat input needed at Q9 via heat exchange between methanol product stream 135 and compressed syngas stream 136. The product methanol may be removed from methanol synthesis 130B via methanol product stream 135.

According to embodiments of this disclosure, methanol synthesis 30/130 can be effected with a reduced usage of non-carbon based energy, the use of renewable energy, and/or the use of electricity (e.g., electricity from renewable and/or non-renewable source(s)). For example: in embodiments, the heat removal Q6 required to attain a desired water gas shifting temperature by cooling B1 can be electrically provided; the heat removal Q7 required to effect syngas cooling B2 can be electrically provided; the heat removal Q8 for cooling and water removal/condensing B3 can be electrically provided; the compression provided at syngas compression C2 can be effected via a motor or an otherwise electricity-driven compressor rather than via a steam or gas-driven turbine or via a turbine driven by electrically-produced steam; the heating Q9 needed to reach a desired methanol synthesis temperature at heating A4 can be electrically provided; electrical cooling may be utilized for heat removal Q10 from methanol synthesis reactor(s) of methanol synthesis 130B, or a combination thereof.

As noted above, a methanol synthesis plant of this disclosure can comprise a methanol purification section 40/140. The methanol purification section 40/140 can be operable to remove a crude methanol product from the methanol synthesis product, remove one or more components (e.g., light ends, heavy byproducts, water, or a combination thereof) from the crude methanol product, recycle syngas vapor to methanol synthesis 130B, and/or purge gas from the system. In embodiments, any suitable methanol purification system known in the art can be utilized, so long as it has been modified to include non-carbon based energy, renewable energy, and/or electricity (e.g., has been electrified to use renewable and/or non-renewable electricity for power) as per this disclosure.

In embodiments, the methanol purification section 40/140 can comprise crude methanol separation apparatus, a recycle compressor to recycle syngas vapor to the methanol synthesis apparatus, a purge gas system operable to purge gas (e.g., a portion of the unconverted synthesis gas enriched in inerts and other less desired components, such as $CO_2$ and $N_2$) from the methanol purification section, a light ends removal apparatus, a heavy byproducts separation apparatus, a methanol/water separation apparatus, associated heating, cooling, and/or compressing apparatus, or a combination thereof, as described further hereinbelow.

As noted above, a methanol purification section 40/140 can comprise cooling. For example, cooling B4 may be utilized downstream of methanol synthesis 130B (with heat removal indicated at Q11). In embodiments, the methanol synthesis reactor effluent is cooled at cooling B4 to near ambient temperature, where the crude methanol and formed water from the reaction condenses. In embodiments, a majority, greater than 20, 30, 40, 50, 60, 70, 80, or 90%, or substantially all of the energy consumed to provide the heat removal Q1l needed at syngas cooling B4 is provided from a non-carbon based energy source, from a renewable energy source, such as renewable electricity, and/or from electricity (from a renewable and/or non-renewable source). In embodiments, some or a majority of a number of pumps utilized to circulate cooling water are electrically driven. Desirably, as noted hereinabove, heat removal Q11 is effected via heat exchange with compressed syngas stream 136 to provide the heat input Q9 at syngas heating A4.

As noted above, a methanol purification section 40/140 can comprise crude methanol recovery at 140A. In embodiments, crude methanol recovery is effected by a gas/liquid separator operable to separate the water and methanol condensed at cooling B4 from the gas (e.g., syngas vapor).

As noted above, the methanol purification section 40/140 can comprise compression apparatus (also referred to herein as a recycle compressor) C3 operable to recycle unconverted syngas to the one or more methanol synthesis reactor(s). In the embodiment of FIG. 4, the unreacted gas is compressed via recycle compressor C3, and recycled back to methanol synthesis 130B via gas recycle stream 144. In embodiments, recycle compression may also be combined with syngas compression. The production of synthesis gas from methane via steam reforming produces three moles of hydrogen for every mole of carbon monoxide (Eq. (3)), while the methanol synthesis (Eq. (6)) consumes only two moles of hydrogen gas per mole of carbon monoxide. To deal with excess hydrogen, carbon dioxide may be injected into the methanol synthesis reactor(s), in embodiments. Thus, in embodiments, carbon dioxide may be introduced into the one or more methanol synthesis reactor(s) via compressor C2 or C3, as indicated by $CO_2$ stream 123' in the embodiment of FIG. 4.

Residual methane and other inerts, such as nitrogen and argon, as well as unreacted CO, $H_2$ and $CO_2$, build up in the recycle gas stream. These can be purged from the recycle gas via a purge gas system. As noted above, the methanol purification section 40/140 can thus comprise a purge gas system operable to purge gas (e.g., including methane, nitrogen, argon) from the methanol purification section 40/140. In embodiments, to handle residual gas (e.g., methane, nitrogen, argon) build-up in the recycle gas in gas recycle stream 144, a portion of the gas is purged from the recycle gas via a purge gas system 140B. In the embodiment of FIG. 4, purge gas in line 143 enters purge gas system 140B, and is removed from the methanol synthesis plant via purge line 105'. In embodiments, a purge stream 105" is utilized to extract purge gas upstream of recycle compressor C3. In embodiments, all or a part of the purge gas may be introduced into pretreating section 10/110 or syngas synthesis section 20/120 as a component of the reformer feed. Purge gas system 140B can involve heat removal, which can be provided electrically, in embodiments. Additional steps, such as water scrubbing, can be used to help improve the per pass recovery of methanol and avoid losses. Some purge gas systems include additional separations to recover specific purge gas components, such as hydrogen. Such additional steps, separations, and apparatus therefor (e.g., hydrogen removal and/or hydrogen purification apparatus, water scrubbing and/or water scrubbing apparatus) are within the scope of this disclosure. In embodiments, fractionation, adsorption, gas permeable membrane separation, molecular sieves, absorption may be used as separation methods. In embodiments, chemical reactions (e.g., methanation) may be used to enhance or enable the practical feasibility or efficacy of the separation methods. In embodiments, such additional separations are also electrified and/or otherwise effected at least in part without the use of non-renewable carbon-based energy. In embodiments, purge gas is not burned for its fuel value, as is common in conventional operation. In embodiments, less than or equal to about 50, 40, 30, 20, 10, 5, 4, 3, 2, or 1 weight percent (wt %) of the purge gas is combusted (e.g., within the syngas synthesis section 20/120 or elsewhere in the methanol synthesis plant). In embodiments, purge gas is not burned for its fuel value, but is separated into one or more different streams comprising specific compounds or groups of compounds, where such one or more different streams are further processed in specific beneficial manners. For example in embodiments, methane and/or nitrogen are removed (e.g., via fractionation) from the purge gas. In embodiments, the methane and nitrogen are removed from the purge gas by cryogenic fractionation that is cooled by a vapor compression heat pump where the compressor is powered by an electric motor. In embodiments, the methane is recycled for use as a feed for methanol synthesis. In embodiments, nitrogen and/or methane removed from the process is sent for use in an ammonia synthesis process. In embodiments, inert gases such as nitrogen and argon are removed from the process while some or all of the remaining components (e.g., CO, $CO_2$, methane, and/or hydrogen) are recycled. In embodiments, hydrogen is separated from the purge gas in purge gas stream 105' or 105", and the separated hydrogen is recycled directly to the methanol synthesis section 30/130 and/or utilized for some other duty within the plant (e.g., utilized in the feed pretreatment section, such as for hydrodesulfurization via Equation (1) or burned to provide heat). In embodiments, hydrogen separated from the purge gas in purge gas stream 105' or 105" is removed from the process and consumed elsewhere.

In embodiments, the purge gas separation system comprises multiple systems, taking gas streams from different parts of the plant, for example, a high pressure purge gas system for the methanol synthesis loop purge gases and a low pressure purge gas system for the crude methanol degassing column light ends. In embodiments, different streams of the multiple systems can be connected together in series or parallel in the overall purge gas processing scheme. In embodiments a compressor is used to increase the pressure of a low pressure purge gas to enable recycle or treatment in a purge gas separation system operating at higher pressure. In embodiments, the purge gas system is a single, unified processing unit.

In embodiments, the methanol synthesis plant further comprises a hydrogen separation apparatus downstream from the methanol synthesis section and configured to separate hydrogen produced in the reformer from a purge gas, thus providing a separated hydrogen stream, a hydrogen purification apparatus configured to purify the separated hydrogen stream, thus providing a purified hydrogen stream; and/or one or more fuel cells operable to make electricity from the purified hydrogen stream. The methanol synthesis plant can further comprise storage apparatus configured for storage of the separated hydrogen, the purified hydrogen, or a combination thereof, such that the separated hydrogen, the purified hydrogen, or the combination thereof can be stored when electricity is readily available, and whereby the stored hydrogen can be utilized to make electricity in the one or more fuel cells when other sources of electricity are not readily available and/or are not available at a desirable price. In embodiments, the separated hydrogen is sent to an ammonia synthesis and/or other process.

As noted above, a methanol purification section 40/140 can comprise separating methanol from the crude methanol product in crude methanol stream 146. Any suitable separations can be utilized, so long as they are effected in accordance with the utilization by the methanol synthesis plant of non-carbon based energy, renewable energy, and/or electricity (e.g., renewable and/or non-renewable electricity) as per this disclosure. The temperature in the purification section for separating the methanol from the crude methanol stream is generally 150° C. or lower, in embodiments. In embodiments, separating methanol from the crude methanol stream comprises removing light ends, heavy byproducts, and/or water from the methanol to provide a purified methanol product 145.

In embodiments, separating methanol from the crude methanol stream 146 comprises removing light ends from the crude methanol product at 140C. In embodiments, a degassing column is utilized at 140C to separate the crude methanol in stream 147 from light gases. Heat (as indicated at Q12) may be introduced to effect this light ends removal, in embodiments. As per this disclosure, in embodiments, a majority, greater than 20, 30, 40, 50, 60, 70, 80, or 90%, or substantially all of the net heat input (Q12) needed at product light ends removal 140C is provided from a non-carbon based energy source, from a renewable energy source, such as renewable electricity, and/or from electricity (e.g., electricity from a renewable and/or a non-renewable source).

In embodiments, separating methanol from the crude methanol stream further comprises separating heavy byproducts at heavy byproducts separation 140D. Hydrocarbon and higher alcohol byproducts that are formed in the methanol synthesis reaction at methanol synthesis 130B can be separated by fractionation. These heavy byproducts can be taken out either as a side draw from either the light ends removal apparatus (e.g., a degassing column) utilized at light ends removal 140B or from a methanol/water separation apparatus (e.g., a methanol purification tower) at methanol/water separation 140E, or by a top or bottom product from a separate distillation tower. For example, as indicated in the embodiment of FIG. 4, a methanol stream 147 from light ends removal 140C can be introduced into a heavy byproducts separation apparatus at 140D, wherein heavy byproducts can be removed from the methanol stream 148. Heat (as indicated at Q13) may be introduced or removed to effect this heavy byproducts removal, in embodiments. As per this disclosure, in embodiments, a majority, greater than 20, 30, 40, 50, 60, 70, 80, or 90%, or substantially all of the net heat input or removal (Q13) needed at heavy byproducts separation 140D is provided from a non-carbon based energy source, from a renewable energy source (e.g., from a non-fossil fuel based energy source $E_{NF}$), such as renewable electricity, and/or from electricity (e.g., electricity from a renewable and/or non-renewable source).

In embodiments, separating methanol from the crude methanol stream further comprises separating methanol and water at methanol/water separation 140E. In embodiments, methanol and water are distilled to purify methanol, and thus provide a purified methanol product 145 and water 149. Where sufficiently free from detrimental contaminants or trace chemistry modifiers, such as NaOH, water 149 can be recycled to a shift reactor(s) for shifting at 130A and/or to steam generation 112. Alternatively, water 149 can be cleaned prior to recycle.

The methanol/water separation at 140E can be effected in a single fractionating tower (e.g., distillation column) or multiple towers (e.g., multiple distillation columns) for heat integration purposes. Heat (as indicated at Q14) may be introduced or removed to effect this methanol/water separation, in embodiments. As per this disclosure, in embodiments, a majority, greater than 20, 30, 40, 50, 60, 70, 80, or 90%, or substantially all of the net heat input or removal (Q14) needed at methanol/water separation 140E is provided from a non-carbon based energy source $E_{NC}$, from a renewable energy source (e.g., from a non-fossil fuel based energy source $E_{NF}$), such as renewable electricity, and/or from electricity (e.g., electricity from a renewable and/or non-renewable source). In embodiments, the temperatures of individual trays on a distillation column of methanol/water separation 140E are controlled electrically to improve separation efficiency.

According to embodiments of this disclosure, methanol purification can be effected with a reduced usage of non-carbon based energy and/or non-renewable energy, with the (increased) use of renewable energy, and/or with the use of electricity (e.g., renewable electricity from renewable and/or non-renewable source(s)). For example, in embodiments, the net heat removal Q11 (e.g., any heat removal needed beyond that provided by heat exchange with another process stream) needed at syngas cooling B4 can be electrically provided; the compression provided at recycle compressor C3 can be effected via a motor or an otherwise electricity-driven compressor rather than via a steam or gas-driven turbine or via a turbine driven by electrically-produced steam; the net heat input or removal Q12 needed for light ends removal at 140C can be electrically provided; the net heat input or removal Q13 needed for heavy byproduct separation 140D can be electrically provided; the net heat input or removal Q14 needed for water/methanol separation 140E can be electrically provided; or a combination thereof.

As noted in Table 1 hereinabove, electrical heating provides a higher energy efficiency than heating via fuels combustion. In embodiments, distillation column feeds can be heated by mechanical heating, resistive heating elements, impedance, thermoelectric devices, and/or electromagnetic waves heating the process fluid or another media from which the heat is transferred. In embodiments, distillation columns can be heated electrically at the reboilers and/or in individual sections by mechanical heating, electric resistance heaters, impedance, thermoelectric devices, and/or electromagnetic waves heating the process fluid or another media from which the heat is transferred. Heat pumps (vapor compression, absorption, adsorption, or chemical) may be used. Thermoelectric devices may be used as heat pumps, in embodiments. In embodiments, distillation column condensers and product coolers can be cooled by electrically powered air coolers, cooling water circuits, thermoelectric devices, and/or heat pumps.

In embodiments, one or more of the Q1-Q15 can be provided by recovered heat, rather than by externally supplied energy. In embodiments, a majority, greater than 20, 30, 40, 50, 60, 70, 80, or 90%, or substantially all of the net heat input or removal needed within the methanol synthesis plant, the feed pretreating section, the syngas synthesis section, the methanol synthesis section, the methanol purification section, or a combination thereof is provided from a non-carbon based energy source $E_{NC}$, from a renewable energy source (e.g., from a non-fossil fuel based energy source $E_{NF}$), such as renewable electricity, and/or from electricity (e.g., electricity from renewable and/or non-renewable source(s)). In embodiments, a majority, greater than 20, 30, 40, 50, 60, 70, 80, or 90%, or substantially all of the net heat input or removal needed within the methanol synthesis plant, the feed pretreating section, the syngas synthesis section, the methanol synthesis section, the methanol purification section, or a combination thereof is provided from a non-carbon based energy source $E_{NC}$, from a renewable energy source (e.g., from a non-fossil fuel based energy source $E_{NF}$), such as renewable electricity, and/or from electricity (e.g., electricity from renewable and/or non-renewable source(s)).

In embodiments, a majority, greater than 20, 30, 40, 50, 60, 70, 80, or 90%, or substantially all of the energy needed for compression (e.g., at feed gas pressure adjustment C1, syngas compression C2, and/or recycle compressor C3) within the methanol synthesis plant, the feed pretreating section, the syngas synthesis section, the methanol synthesis section, the methanol purification section, or a combination thereof is provided from a non-carbon based energy source, from a renewable energy source, such as renewable electricity, and/or from electricity (e.g., electricity from renewable and/or non-renewable source(s)). For example, an electric motor, an electrically-driven turbine, and/or a turbine driven by steam produced electrically may be utilized to provide compression throughout the methanol synthesis plant or one or more sections thereof. In embodiments, a majority, greater than 20, 30, 40, 50, 60, 70, 80, or 90%, or substantially all of the compressors are replaced by or utilize an electric motor, an electrically-driven turbine, and/or a turbine driven by steam produced electrically.

In embodiments, electricity can be used to provide the motive force for fluids. For example, electricity can be used to power pumps to move and/or pressurize liquids, and/or to power air blowers and/or fans. In embodiments, a fraction, a majority, or all (e.g., 20, 30, 40, 50, 60, 70, 80, 90, or 100%) of the number of pumps utilized in the methanol synthesis plant are electrified.

In embodiments, electricity is utilized to produce slightly colder (e.g., 2, 5, 10 or 15° C. colder) cooling water than conventional.

As noted above, when utilizing electricity from a renewable source that has a potentially or known intermittent supply (e.g., an intermittent energy source or IES), various steps can be taken to maintain operation of the methanol synthesis plant, according to embodiments of this disclosure. Such handling of an IES can be as described in U.S. Provisional Patent Application Nos. 62/792,636 and 62/792,637, entitled Use of Intermittent Energy in the Production of Chemicals, which are being filed on Jan. 15, 2019, the disclosure of each of which is hereby incorporated herein for purposes not contrary to this disclosure. For example, in embodiments, compressed hydrogen is stored for intermittency of electric supply. Alternatively or additionally, one or more cryogenic liquids can be stored for intermittency of electric supply. Alternatively or additionally, heat can be stored for intermittency of electric supply. Alternatively or additionally, batteries can be kept for intermittency of electric supply. Backup power for key components may be provided; non-renewable electricity may be utilized as a back-up for intermittent renewable electricity, in embodiments. For example, such backup power may be produced via apparatus driven by compressed gas or a flywheel. Alternatively or additionally, in embodiments, a feed (e.g., a natural gas feed) can be compressed and stored when electricity is available and expanded through a power-generating turbine to provide feed and electricity during times of low electric supply. Alternatively or additionally, recovered $H_2$ (e.g., from purge gas 143, 105', 105") can be pressurized and stored when electricity is available and used to generate electricity using a fuel cell during times of low electric supply.

Electrification of the methanol synthesis plant of this disclosure can be provided via an electricity supply that can be high voltage or low voltage. The electric devices can be operable or operated on alternating (single or multiphase) or direct current.

In embodiments, steam generated by the combustion of fuels or produced solely for heat and/or energy transfer is not utilized in a methanol synthesis plant and method of this disclosure (e.g., in the pretreating section 10, the syngas synthesis/reforming section 20/120, the methanol synthesis section 30/130, and/or the methanol purification section 40/140). In this manner, a methanol synthesis plant according to this disclosure can be operated, in embodiments, without an elaborate steam heat and/or energy transfer system (which may be conventionally utilized in a chemical plant for producing methanol). In some applications, for example where steam is utilized within a reactor as a feed component and/or diluent, such steam may be produced via heat transfer with a process stream within the methanol synthesis plant and/or may be produced electrically. In embodiments, steam generated via heat transfer with a process stream may be superheated using electricity. In embodiments, steam is not utilized throughout the methanol synthesis plant as a commodity or utility. In embodiments, a methanol synthesis plant of this disclosure is essentially steam-free, or utilizes substantially less steam (e.g., uses at least 10, 20, 30, 40, 50, 60, 70, 80, 90, or 100 volume percent (vol %) less steam) than a conventional plant for producing methanol. For example, a conventional plant for producing methanol may utilize steam production for reboilers of distillation columns of the feed pretreating section 10 and/or the methanol purification section 40/140, may utilize steam production to drive steam turbines for compressing process and/or recycle streams, or may utilize steam production to drive steam turbines for refrigeration. In embodiments, steam is not produced for these operations in a methanol synthesis plant according to this disclosure, or substantially less steam is produced (e.g., at least 10, 20, 30, 40, 50, 60, 70, 80, 90, or 100 volume percent (vol %) less steam). In embodiments, steam is used as a heat transfer fluid, but is not used to do mechanical work (e.g., to drive a compressor or pump.) In embodiments, the steam generated for these operations is primarily (e.g., of the total steam utilized, the greatest percentage is electrically produced), mainly (e.g., greater than 50% of the steam is electrically produced) or substantially all electrically produced. In embodiments, the steam utilized as a reactant or diluent is primarily (e.g., of the total steam utilized, the greatest percentage is electrically produced), mainly (e.g., greater than 50% of the steam is electrically produced) or substantially all electrically produced.

In embodiments, in a methanol synthesis plant or process of this disclosure, more energy is utilized directly 'as-is', for example, utilizing heat from a hot product effluent stream to heat a feed stream, rather than being transformed, e.g., via the generation of steam and the conversion of the thermal energy to mechanical energy via a steam turbine. According to embodiments of this disclosure, the use of energy directly can increase the energy efficiency of the methanol synthesis plant, for example by reducing energy efficiency losses that occur when heat is converted to mechanical energy.

As energy consumption is a large fraction of the operating costs of a traditional methanol synthesis plant, increasing energy efficiency (e.g., via electrification) as per this disclosure and/or utilizing methane conventionally burned to provide heat for reforming and/or burned for compression (e.g., burned to produce steam for a steam turbine or burned for a gas turbine) to produce additional methanol may provide economic advantages over a conventional methanol synthesis plant. Concomitantly, the reduction of the burning of fossil fuels (e.g., natural gas, methane) as a fuel enabled via this disclosure provides for reduced greenhouse gas (GHG) emissions relative to a conventional methanol synthesis plant in which hydrocarbons are burned as fuel. In embodiments, GHG emissions (e.g., carbon dioxide emissions) are reduced by at least 5, 10, 20, 30, 40, 50, 60, 70, 80, 90, or 100% relative to a conventional methanol synthesis plant in which hydrocarbons are burned as fuel. In embodiments of this disclosure, the amount of $CO_2$ produced per ton of methanol produced is reduced to 0.30, 0.25, 0.2, 0.1, 0.05, or 0 tons $CO_2$ per ton methanol. In embodiments, energy efficiency (e.g., reduced energy losses) is increased by the elimination of the flue gas, since the loss of heat contained in the flue gas to the atmosphere is eliminated. In embodiments, energy efficiency (e.g., reduced energy losses) is increased by a decrease in or elimination of the use of steam to do mechanical work. In embodiments, the energy efficiency of the process is increased such that the specific energy consumption (the total net energy input, including feed methane, fuel, and electricity, and giving credit for byproducts produced, to the process divided by the production rate) is 34, 33, 32, 31, 30, 29, 28, or 27 GJ/ton of methanol produced, where the specific energy consumption is calculated using the higher heating value of the fuel, feed, and byproducts. In embodiments, aspects of this disclosure can lead to an increase in carbon efficiency of a process, i.e. to a fraction of carbon consumed in the process that reappears as a useful product. In embodiments, the carbon efficiency of the process is greater than or equal to about 82, 84, 86, 88, 90, 92, 94, 95, 96, 97, 98, 99, or 100%.

Conventionally, the energy required for unit operations in chemical processes is generally provided by the burning of fossil fuels, especially natural gas. Herein-disclosed are systems and methods by which this energy input can be reduced or replaced, in embodiments, with non-carbon based energy, renewable energy, such as renewable electricity, and/or by electricity from any source (e.g., renewable and/or non-renewable), such that energy efficiency is improved. The herein-disclosed use of non-carbon based energy, renewable energy (e.g., non-fossil fuel based energy), and/or electricity in the production of chemicals, such as the production of methanol via syngas reforming or partial oxidation, increases energy efficiency of and/or decreases and/or eliminates carbon dioxide emissions from and fossil fuel consumption within the methanol synthesis process.

In embodiments, no steam is used as an energy transfer medium anywhere within the process. In embodiments, steam is only used as an energy transfer medium to move thermal energy within the process, e.g., to facilitate the use of heat recovered from cooling one process stream into the heating of a second process stream. In embodiments, some or all of the heat recovered from cooling one or more process streams is used only to heat one or more other process streams via direct heat exchange (i.e., via direct or indirect heat transfer with another process stream without utilizing steam as a heat transfer intermediate). In embodiments, no steam is used to do mechanical work within the methanol synthesis plant. In embodiments, no flue gas is produced via the combustion of a fuel, a carbon-based fuel, a fossil fuel, or a combination thereof within the methanol synthesis plant. In embodiments, hydrogen recovered from the methanol synthesis process (e.g. from purge gas stream 143, 105', 105") is sent to an ammonia synthesis plant. In embodiments, hydrogen recovered from the process (e.g. from purge gas stream 143, 105', 105") is sent to another chemical process, e.g., for use in the refining of oil and/or oil derivatives.

In embodiments, electric heating is used to impose a temperature profile on a reactor (e.g., a reformer) of syngas synthesis section 20/120, a methanol synthesis reactor and/or a water-gas shift reactor, such as at methanol synthesis 130B and water-gas shift 130A, of a methanol synthesis section 30/130, or a combination thereof. In embodiments, mechanical heating is used to heat a feed to a reactor (e.g., a reformer) of syngas synthesis section 20/120, a methanol synthesis reactor and/or a water-gas shift reactor, such as methanol synthesis 130B and water-gas shift 130A, of a methanol synthesis section 30/130, or a combination thereof.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner. As utilized herein between components or process steps, a slash "/" indicates and/or, for example, 'feed preheating A1/A2/A3' indicates 'feed preheating A1, A2, A3, or a combination thereof'. Similarly, '140D/140E' indicates '140D, 140E, or both'. Although specific operating conditions are utilized in the process simulations of the Examples, it is to be understood that other operating conditions (e.g., temperatures, flow rates, etc.) may be apparent to those of skill in the art upon reading this disclosure and are intended to be included within the scope of this disclosure.

Comparative Example 1

A process simulation was performed to determine the heat and mass flows for a typical process III for the production of methanol from natural gas. The process simulation utilized in this Comparative Example 1 was made using Aspen Plus®, a commercial chemical process simulation software tool. It does not represent a specific operating plant, but it is representative of a typical plant or process III as described hereinbelow with reference to FIG. 5; the design parameters were taken from knowledge of specific plants, as well as literature information on typical process operations. Although variations will be obvious to one skilled in the art, this Comparative Example 1 represents a typical process III that can be used as a basis for comparing the effects of electrification modifications according to embodiments of this disclosure.

Process III of Comparative Example 1 is configured to produce 5,000 metric tons per day of methanol. If operated for 8,000 hours in a year, this would result in the production of 1.67 million tons of methanol, although variations in downtime due to upsets and maintenance could increase or reduce this output. This size is typical of contemporary large methanol plants.

The natural gas composition used in Comparative Example 1 and all of the subsequent Examples and Comparative Examples is typical of natural gas found in some parts of the Middle East. It contains 88.9 mol % methane, 2.3 mol % ethane, 0.8 mol % $C_{3+}$ hydrocarbons, 7.8% $N_2$, and 0.2% $CO_2$. It has a higher heating value (HHV) of 48.0 GJ/t.

Figure 5:
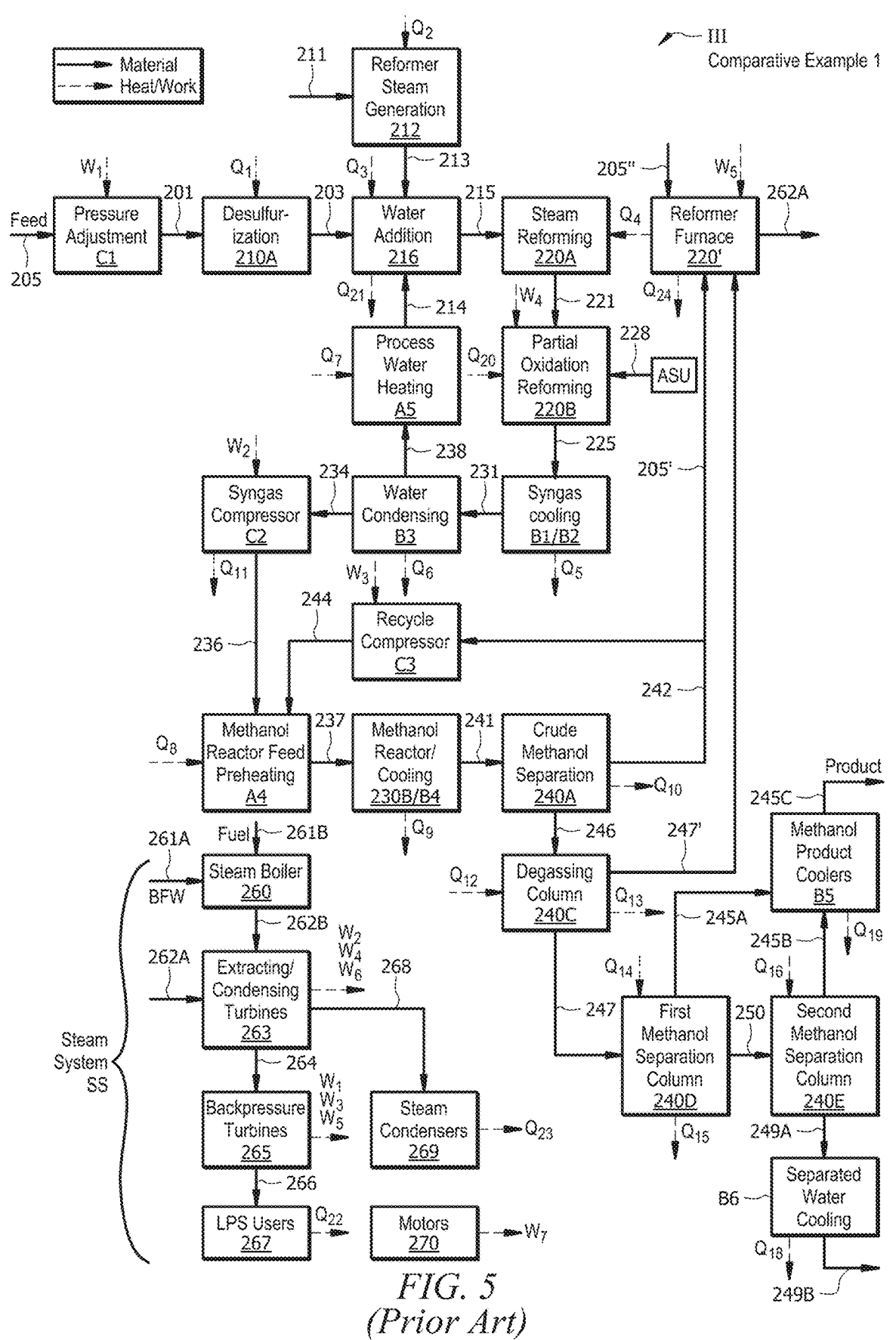
FIG. 5 shows a block flow diagram of a conventional methanol synthesis plant or process III, discussed in Comparative Example 1 of this disclosure.

As shown in FIG. 5 (which has been simplified to show only the essential features of process III of this Comparative Example 1), 135 metric tons per hour (t/h) of natural gas feed 205 are fed to the feed pretreatment section where it underdoes pressure adjustment (e.g., at C1) and desulfurization (e.g., at 210A) (hydrogen addition not shown) after heating (e.g., at feed pretreatment A1) to the desired desulfurization temperature of 385° C. Water 214 and steam 213 are added to provide a reforming feed 215 (e.g., with a steam to carbon molar ratio of 1.8), and the feed 215 is preheated (e.g., at feed pretreatment A1/A2/A3) and fed to a steam methane reformer of 220A where the feed is passed over a reforming catalyst while being heated in the radiant section of a reforming furnace 220'. The effluent 221 of the steam reformer is passed to a partial oxidation reforming unit 220B where 95 t/h of oxygen 228 is added and reacted with the gas stream. The temperature of the effluent 225 exiting the partial oxidation reformer 220B is 976° C. The reforming product 225 is cooled down (e.g., in syngas cooling B1/B2) to close to the mixture dew point before further cooling of the cooled syngas 231 to 45° C. in a water condensing and removal section (e.g., water condensing B3) to generate an essentially dry syngas stream 234 and a recycle water stream 238. The dried syngas 234 is passed to a syngas compressor C2 where the pressure is increased from 35 to 99 bar. The compressed, dried syngas 236 is mixed with recycled syngas 244 and preheated (e.g., at syngas heating A4) to 165° C. The preheated syngas 237 is fed to the methanol reactors of 230B where it is heated to the final reaction temperature and passed over a methanol synthesis catalyst. The methanol synthesis reaction, which is exothermic, is cooled (e.g., at cooling B4, which is integrated in this example into the methanol synthesis reactors of 230B) by water which is vaporized, sent to the water addition section 216 and condensed to provide the heat required for the water addition to the feed. The methanol reactor effluent 241 is cooled down to 45° C. in crude methanol recovery/separation 240A where vapor and liquid phases are separated. The vapor phase 242 is passed to the recycle compressor C3 after taking 34 t/h off as a purge gas stream 205'. This purge gas 205' from the synthesis loop is combined with the low pressure off gases 247' from a degassing column of light ends removal 240C to provide a 44.6 t/h stream containing 53 mol % $H_2$, 19 mol % $N_2$, 13 mol % $CH_4$, 10 mol % $CO_2$, and 4% other compounds; this stream is then burned in the reformer furnace 220' for fuel, along with 10.3 t/h of natural gas 205". The liquid stream 247 is fed to a degassing column at 240C where it is heated to remove light gases 247' dissolved in the crude methanol stream 246. The degassed crude methanol 247 is fractionated to provide a substantially pure methanol product stream. This is effected, in this Comparative Example 1, via a 2 column sequence where a partial recovery 245A of the methanol is taken in the first column 240D and the remaining methanol 245B is purified by fractionation in the second column 240E. Heavy byproducts are purged via a small side stream in the column (not shown). The overhead streams (245A/245B) of each of the columns (240D/240E, respectively) are cooled in methanol product coolers at B5 to 45° C. before being sent to methanol product handling and storage as methanol product 245C.

The water 249A separated from the methanol is cooled as well, e.g., in separated water cooling at B6, before discharging as cooled water 249B. Water 238 that was condensed from the syngas 231 is reheated (e.g., at process water heating A5) and recycled to the water addition 216. A small fraction of the water (not shown in the Figures) can be purged from the system to prevent the buildup of impurities.

The major energy consumers of Comparative Example 1 are (see Table 2, discussed further hereinbelow): (1) heat (e.g., Q4) supplied to the steam reformer, (2) generation of the steam required as feed for syngas production, (3) methanol distillation (e.g., in a first methanol separation column of 240D and a second methanol separation column of 240E), (4) reformer feed preheat (e.g., at feed preheating A1/A2/A3), (5) methanol reactor feed preheat (e.g., at syngas heating A4), (6) energy (e.g., for work W2) to drive the syngas compressor C2, and (7) energy to drive an air separation unit ASU for the production of oxygen 228. Smaller amounts of energy are used for a variety of other purposes. As is common practice, very little electricity is consumed in Comparative Example 1, primarily for some smaller pumps; the electrical demand for process users is only 1.7 MW. A significant amount of the energy used can be obtained by heat exchange with the product streams as they are cooled, most notably the hot syngas (e.g., 221/225) from the reformer (e.g., at 220A/220B) and the product from the methanol reactor(s) at 230B/B4. The remaining energy is supplied as combusted fuels in the reforming furnace 220' and a steam boiler 260. The reforming furnace 220' serves multiple purposes, supplying heat for the steam reforming reaction from the radiant section, providing some feed preheating in the convection section, and supplying heat in the convection section for use in high pressure steam 262A generation. Cooling of the syngas is also utilized in the generation of high pressure steam 262A. The remaining high pressure steam 262B is generated by the steam boiler 260. The high pressure steam 262A/262B is directed through a system of steam turbines (e.g., 363/265) to drive the large power users of the plant. In Comparative Example 1 the syngas charge compressor C2, the air separation unit ASU, and the cooling water pumps are partly extracting plus condensing turbines (e.g., indicated at 263). The gas feed booster compressor, reformer air/flue gas fans, and the syngas recycle compressor C3 are backpressure turbines (e.g., indicated at 265) that exhaust 182 t/h low pressure steam 266 that is used for heating in the process III. In Comparative Example 1, there are two major locations which utilize external sources of energy. The first is in the reformer at 220A, which consumes 10.3 t/h of natural gas 205" with a contained chemical energy (high-heating value, or HHV) of 138 MW plus 44.6 t/h of process off gases comprising purge gas 205' from the synthesis loop and the low pressure off gases 247' having a contained chemical energy (high-heating value, or HHV) of 252 MW. The remaining external energy is supplied by a steam boiler 260 that converts boiler feed water BFW 261A to high pressure (HP) steam 262B utilizing 9.7 t/h of natural gas fuel 261B with a contained chemical energy of 130 MW. How to most efficiently allocate this energy to the various consumers of energy in the process with the highest efficiency is an engineering problem that can be addressed by one of skill in the art upon reading this disclosure via careful matching of temperatures, types of energy, and energy content. Some of the energy can be transferred directly via heat exchange, while some can be converted to steam that can either be used for heat exchange or to do mechanical work, such as drive a compressor. In Comparative Example 1 a typical strategy has been adopted for matching heat inputs and outputs, but other arrangements are possible, as will be obvious to one skilled in the art upon reading this disclosure. The use of combustion furnaces to supply the external energy input needed for the process comes with a concomitant disadvantage—the stack or flue gas from these furnaces contains energy that cannot be usefully recovered because of its low temperature. For example, in the process of Comparative Example 1, this unrecovered energy, sometimes referred to as stack losses, amounts to 71 MW at the reformer furnace 220' of steam reforming 220A and 26 MW at the steam boiler 260. Energy is also lost in several process steps, primarily in water condensing from various points such as from the syngas (e.g., at water condensing B3) because the temperature is too low for returning the energy to useful purposes.

Comparative Example 1 shows the energy integration configuration chosen for the purposes of this example. One with skill in the art would recognize a number of ways the heat recovery of the syngas cooling and reformer stack could be configured for raising the high pressure steam. For example, the ratios of how much energy is supplied in water preheating, vaporization, and steam superheating can be reassigned among the units according to the design and equipment configuration. Likewise the steam heat raised in the methanol synthesis reactor at 230B could be used for distillation heating (e.g., at 240D/240E) rather than reformer water (e.g., at A5) and steam heating (e.g., at 212). These and other heat integration choices are known art and for various reasons different choices could be taken by one skilled in methanol plant design, while remaining within the scope of this disclosure.

Table 2 shows the energy balance for the process III of Comparative Example 1. As seen in Table 2, an amount of 520 MW of chemical energy is supplied through the combustion of purge gas 205', process off-gas 247', and natural gas 205" in the reformer furnace 220' of steam reforming at 220A and of natural gas fuel 261B in the steam boiler 260; this represents all but 2 MW of the total energy input to the process III that is supplied from external sources. Including the heat supplied by the reforming furnace 220', a large amount of heat (1410 MW) is available within the process III. In addition to the methanol synthesis chemical reaction and cooling hot process streams, heat is internally generated within the process through the reaction of the natural gas with oxygen 228 in the partial oxidation reformer at 220B. A total of 705 MW is recovered from process sources; however, because of the available heat supplied by the steam turbines (e.g., 263/264), as well as the temperature and enthalpy requirements of the process, 385 MW of heat is rejected to cooling water. Additionally the steam system SS rejects 213 MW of heat to cooling water in the condensing turbines (e.g., 269). Furnace stack losses total 97 MW. Overall 705 MW of energy, 50% of the total heat available, is rejected rather than being taken as useful for the process.

Table 3 provides relevant energy use statistics for process III of Comparative Example 1. As seen in the data in Table 3, the carbon efficiency of process III, defined by the carbon contained in the product methanol (e.g., at 245C) divided by the carbon of the total natural gas consumed, is 76.8%. The combustion of this fuel results in the atmospheric emissions of 86 t/h of $CO_2$, or 0.69 million tons of $CO_2$ annually. Net specific energy consumption is 35.8 GJ (33.9 MMBTU) per ton of methanol produced. Net specific energy consumption includes the energy content of the natural gas feedstock (in higher heating value) for making methanol plus the external energy supplied in other forms such as electricity and natural gas for fuel; because the purge gas combusted in reforming furnace 220' is internal to the plant, the energy content of the natural gas feedstock includes the heat content of the purge gas.

Example 1

Example 1 is a partial electrification process IV comprising partial electrification as per an embodiment of this disclosure of the methanol process III described in Comparative Example 1. In Example 1, the external steam boiler is removed and the energy supplied to that boiler by the combustion of natural gas is replaced by a smaller amount of renewable electrical energy that is used to power the air separation unit (ASU).

Figure 6:
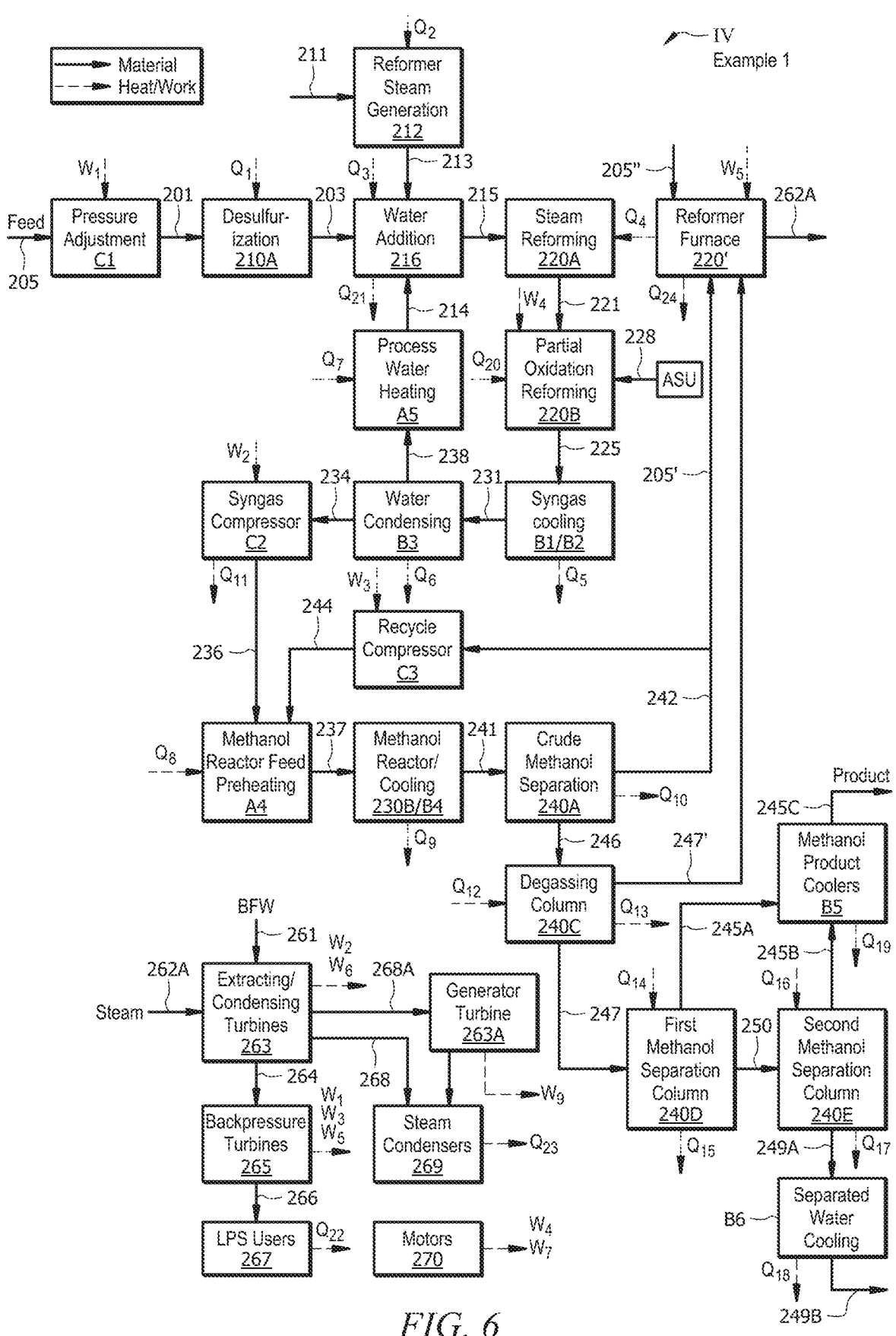
FIG. 6 shows a block flow diagram of an exemplary partially electrified methanol synthesis plant or process IV, according to the embodiment of Example 1 of this disclosure.

The key elements of the partially electrified plant or process IV of Example 1 are shown in FIG. 6. As in Comparative Example 1, an amount of 135 t/h of natural gas 205 is fed to process IV. The main difference in Example 1 is that the energy (e.g., W4) for the oxygen production unit ASU is not obtained from the steam system but is replaced with the power of an electric motor supplied by renewable energy. This reduces the total demand of high pressure steam such that running a steam boiler (e.g., steam boiler 260 of process III of FIG. 5) is no longer necessary and 9.7 t/h of fuel (e.g., 261B in FIG. 5) can be saved. There is additionally a small amount of excess high pressure steam 268A that is run through a turbine connected to an electric generator 263A to recover 2.4 MW of power.

Table 2 shows the energy balance for the partial electrification process IV of Example 1. An amount of 390 MW of chemical energy is supplied through the combustion of process gases (e.g., purge gas 205' and light gases 247') and natural gas (e.g., 205") and 24 MW of renewable electricity are supplied; this represents a total net energy input to process IV of 414 MW, or 21% less than in process III of Comparative Example 1. Total losses from the system from the flue gas, inefficiencies in the use of steam and electricity, and losses in process IV are 15% less than in process III of Comparative Example 1.

Table 3 provides relevant energy use statistics for process IV of this Example 1, according to an embodiment of this disclosure. The carbon efficiency of process IV is 82.0%, an improvement of approximately 5% over that of process III of Comparative Example 1. In this Example 1, the natural gas consumption results in the atmospheric emissions of 63 t/h of $CO_2$, or 0.54 million tons of $CO_2$ annually; this represents a 27% decrease over process III of Comparative Example 1. The 78,000 tons per year of natural gas saved via process IV can be used elsewhere, for example as a feed for an ammonia synthesis process and/or for another methanol plant. Net specific energy consumption of process IV is 33.9 GJ (32.2 MMBTU) per ton of methanol produced, which is 5% less than in that of process III of Comparative Example 1.

Example 2

Example 2 is a complete electrification process V comprising complete electrification, as per an embodiment of this disclosure, of the methanol process III described in Comparative Example 1. In Example 2, the energy supplied to the external steam boiler and the reformer furnace by combustion is replaced with renewable electricity, which powers all pumps and compressors, supplies the energy for steam reforming, and provides some process heat. As a result, there is no external steam system in Example 2. There is also no flue gas, and the only $CO_2$ emitted comes from a small amount of $CO_2$ released from waste water streams. The purge gas that was burned in Comparative Example 1 to provide heat is now exported for other uses.

Figure 7:
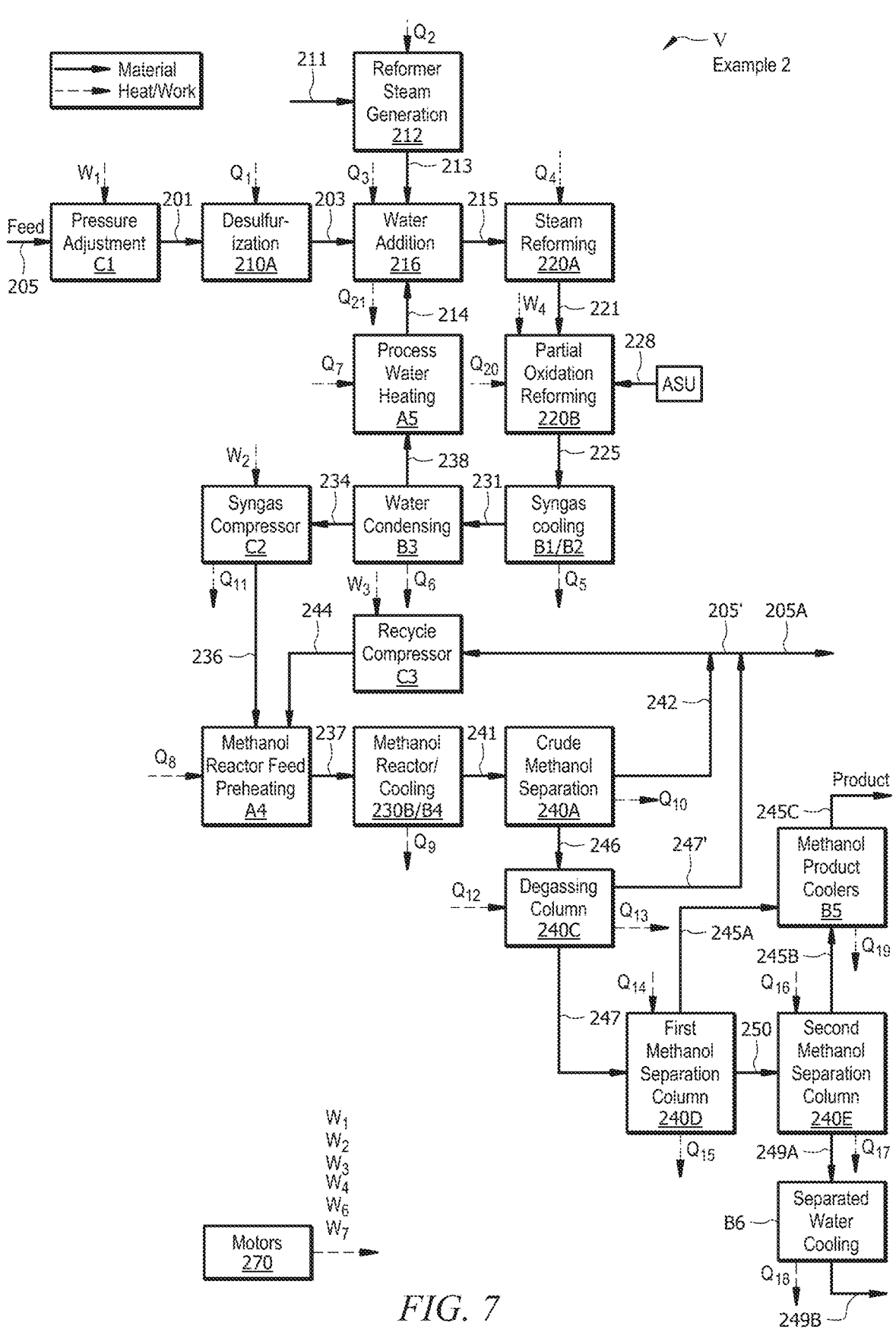
FIG. 7 shows a block flow diagram of an exemplary substantially completely electrified methanol synthesis plant or process V, according to the embodiment of Example 2 of this disclosure.

The key elements of this electrified plant V are shown in FIG. 7. An amount of 135 metric tons per hour (t/h) of natural gas feed 205 is fed to the feed pretreatment section where it underdoes pressure adjustment at C1 and desulfurization at 210A after heating (e.g., at feed preheating A1) to the desired desulfurization temperature of 385° C. Water 214 and steam 213 are added and the feed is preheated (e.g., at feed preheating A1/A2/A3). In this Example 2, the feed 215 is preheated by the effluent 225 of the oxidation reforming unit at 220B and fed to a first steam methane reformer at 220A where the feed is passed over a reforming catalyst while being heated by cooling the effluent 225 of the partial oxidation reforming unit at 220B. The effluent 221 from steam reforming at 220A then passes over a second reforming catalyst bed of partial oxidation reforming 220B that is electrically heated in this embodiment. The effluent 221 of the steam reformer at 220A is passed to the partial oxidation reforming unit 220B where 95 t/h of oxygen 228 is added (e.g., from the ASU) and reacted with the gas stream. The temperature of the effluent 225 exiting the partial oxidation reformer at 220B is 976° C. The reforming product 225 is cooled down (e.g., in syngas cooling B1/B2) to close to the mixture dew point before further cooling the cooled syngas 231 to 45° C. in a water condensing and removal section (e.g., water condensing at B3) to generate an essentially dry syngas stream 234 and a recycle water stream 238. The dried syngas 234 is passed to a syngas compressor C2 where the pressure is increased from 35 to 99 bar. The compressed, dried, syngas 236 is mixed with recycled syngas 244 and preheated (e.g., in syngas heating at A4). The preheated syngas 237 is fed to the methanol reactors at 230B where it is heated to the final reaction temperature and passed over a methanol synthesis catalyst. The methanol reactor effluent 235 is cooled down (e.g., by methanol reactor cooling B4, which is integrated, in this example, into the methanol synthesis reactors of 230B) to 45° C. and vapor and liquid phases are separated (e.g., at crude methanol separation at 240A). The vapor phase 242 is taken to the recycle compressor C3 after taking 34 t/h off as a purge gas stream 205'. The liquid stream 246 is fed to a degassing column at 240C where it is heated to remove light gases 247' dissolved in the crude methanol stream 246. The purge gas 205' from the synthesis loop combined with the low pressure off gases 247' amounts to 44.6 t/h. The total purge gas 205A is a valuable product containing 53 mol % $H_2$, 19 mol % $N_2$, 13 mol % $CH_4$, 10 mol % $CO_2$, and 4% other compounds that can be utilized as a product for other useful purposes with or without further separation, as known to those of skill in the art. Useful purposes can include, without limitation, ammonia production, (substantially) pure hydrogen production, and hydrogenation reactions, among other uses. The degassed crude methanol 247 is fractionated to provide a substantially pure methanol product stream. This is done, in process V, in a two column sequence where a partial recovery 245A of the methanol is taken in the first column 240D and the remaining methanol 245B is purified by fractionation in the second column 240E. The majority of the energy (e.g., Q14/Q16) for the distillation column reboilers is provided by heat recovery. In this embodiment, the remaining 75 MW of heat required for the methanol column reboiler(s) is supplied by electric process heaters. Heavy byproducts are purged via a small side stream in the column (not shown). The overhead streams (e.g., 245A/245B) of each of the columns (e.g., 240D/240E, respectively) are cooled (e.g., in methanol product cooler(s) at B5) to 45° C. before being sent to methanol product handling and storage or the like as methanol product 245C. The separated water 249A separated from the methanol can also be cooled (e.g., in separated water cooling at B6) before discharging. Water 238 that was condensed from the syngas 231 is reheated (e.g., at process water heating A5) and recycled to the water addition 216. A small fraction of the water (not shown in the Figures) can be purged from the system to prevent the buildup of impurities.

How to most efficiently allocate energy from the various sources of energy to the various consumers of energy in the process with the highest efficiency is an engineering problem that can be addressed by one of skill in the art upon reading this disclosure via careful matching of temperatures, types of energy, and energy content. In Example 2 a logical strategy has been adopted for matching heat inputs and outputs, but the same overall energy balance can be achieved with other arrangements, as will be obvious to one skilled in the art upon reading this disclosure. The sequence and amount of heat integration among the oxidation reformer at 220B, steam reformer at 220A, and electric furnace of 220A is considered to be a flexible variable as it is mainly governed by equipment selection and heat integration choices. For example, tighter heat integration between the oxidative reformer at 220B and steam reformer at 220A (by lowering the approach temperature, for example) can reduce the amount of electricity used in the reforming reaction. Similarly, the sequence of reforming heat by heat recovery vs. electric heating is flexible to the extent of temperature availability of both services. For example, electric heat does not need to be applied above 700° C. as 600° C. is sufficient when heat recovery is available above that. Similarly, the 75 MW of low temperature electric heat could be applied in a different manner and still achieve the same overall net heat balance. For example electric heaters can be installed for the heat required (e.g., for process water heating at A5) in the water addition step 216 of the process, thus saving the higher temperature methanol reactor heat for the column reboilers (e.g., at 240D/240E), which could be a capital investment saving alternative due to having higher temperature driving forces, and therefore less heat exchanger area in the column reboilers.

The major energy consumers of Example 2 are (see Table 2, discussed further hereinbelow): (1) heat (e.g., Q4) supplied to the steam reformer at 220A, (2) generation of the steam required as feed for syngas production, (3) methanol distillation (e.g., at 240D/240E), (4) reformer feed preheat (e.g., at feed preheating A1/A2/A3), (5) methanol reactor feed preheat (e.g., at syngas heating A4), (6) energy (e.g., for work W2) to drive the syngas compressor (e.g., at C2), and (7) energy (e.g., work W4) to drive the air separation unit ASU for production of oxygen 228. Smaller amounts of energy are used for a variety of other purposes. A significant amount of the energy used can be obtained by heat exchange with the product streams as they are cooled, most notably the hot syngas from the reformer and the methanol reactor. The external energy inputs are 22 MW of heat supplied by electricity to the steam reforming section 220A, 75 MW of heat supplied by electric heaters to the distillation section (e.g., at 240D/240E), and 74 MW of power required for process drives (e.g., motors 270). By reacting the natural gas with oxygen 228 in the autothermal reformer (e.g., at 220B) and from the methanol synthesis chemical reaction a large amount of heat is also internally generated within the process V. Of the total process heat, 597 MW are transferred internally during the cooling of the various process streams according to this Example 2 according to this disclosure. Although a significant amount of heat is recovered in the process V, 363 MW of heat ends up being rejected to cooling water.

Table 2 shows the energy balance for this complete electrification process V of Example 2. An amount of 180 MW of renewable electricity is supplied to process V; this represents a total net energy input to the process of approximately 65% less than that of process III in Comparative Example 1. Unlike in Comparative Example 1, there is no steam system in the embodiment of Example 2 beyond the steam used as diluent in the feed. Another difference from Comparative Example 1 is that the fully electrified methanol process V does not have stack losses or steam system losses. Overall 372 MW of energy is rejected rather than being taken as useful for process V, which is a 47% reduction relative to process III of Comparative Example 1. The off-gas product 205A has an energy content (higher heating value) of 252 MW.

Table 3 provides relevant energy use statistics for Example 2 according to this disclosure. In Example 2, natural gas is consumed only as a chemical feedstock. The carbon efficiency of process V is 88.2%, an improvement of approximately 11% over process III Comparative Example 1. A relatively minor amount of $CO_2$ is produced, 12,000 tons per year, from combustion of the low pressure off-gases, which amounts to 2% of the $CO_2$ production of process III of Comparative Example 1. The natural gas consumption is 13% less than in process III of Comparative Example 1. The 161,000 tons per year of natural gas saved via process V can be used elsewhere, for example, without limitation, as a feed for an ammonia synthesis process and/or as feed for the or another methanol synthesis process. Net specific energy consumption (calculated as the energy content of the natural gas feedstock for making methanol plus the external energy supplied as electricity less the energy content of the exported purge gases, per ton of methanol produced) is 29.9 GJ per ton of methanol, which is 16% lower than in the process III of Comparative Example 1.

Example 3

Example 3 is a complete electrification process VI, according to an embodiment of this disclosure, comprising substantially complete electrification of the methanol process III described in Comparative Example 1. Example 3 shows how, within the scope of this disclosure, a methanol synthesis process can be designed differently than in Example 2, while still providing all external energy from renewable electricity. As in Example 2, Example 3 does not have an external steam boiler and all pumps and compressors are powered electrically. In contrast to Example 2, in Example 3 the purge gases are separated and used internally rather than exported. The methane from the purge gas is recycled for use as feed, decreasing the amount of natural gas consumed, while the hydrogen is burned to generate steam and heat for a final reforming reactor. Because the purge gas has been separated and only hydrogen is burned, the first steam reformer is heated electrically and no $CO_2$ is emitted by the reforming reactors. (A small amount of $CO_2$ is formed by the combustion of the off-gas from the methanol degassing column.) As in Example 2, there is no steam system in Example 3.

Figure 8:
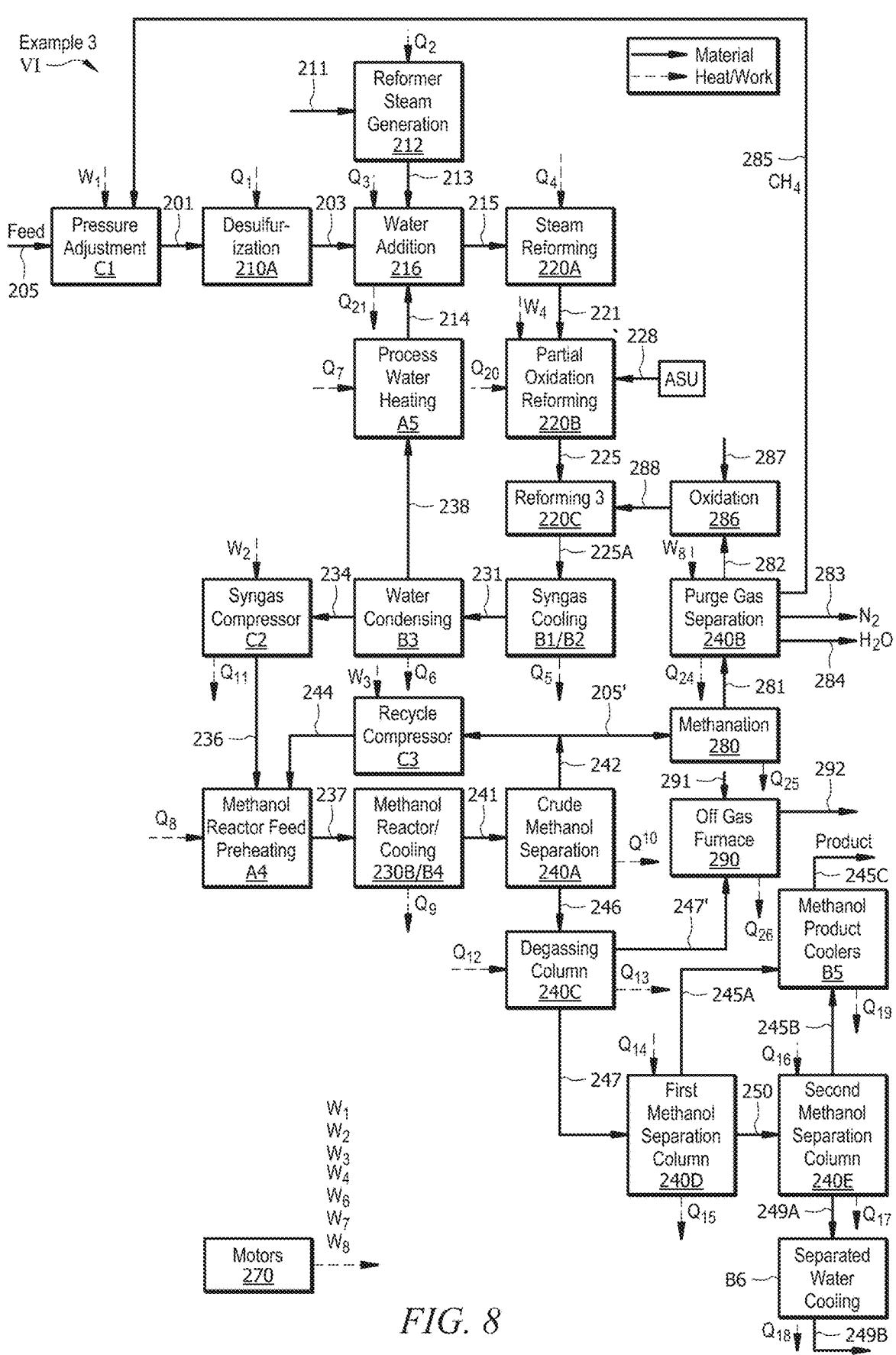
FIG. 8 shows a block flow diagram of an exemplary substantially completely electrified methanol synthesis plant or process VI, according to the embodiment of Example 3 of this disclosure.

As in Comparative Example 1, process VI is configured to produce 5,000 metric tons per day of methanol. The key elements of this electrified plant or process VI are shown in FIG. 8. One distinguishing feature is a Purge Gas Separation unit 240B, which is configured/utilized to recover methane 285 for recycle use as natural gas feed, purges nitrogen 283 from the process VI, and return a hydrogen-rich stream 282 to the process. An amount of 123.2 metric tons per hour (t/h) of natural gas feed 205 is combined with the 3.8 t/h recovered methane stream 285 from the Purge Gas Separation unit 240B and fed to the feed pretreatment section where it underdoes pressure adjustment at C1 and desulfurization at 210A after heating (e.g., at feed preheating A1) to the desired desulfurization temperature (e.g., 385° C.). Water 214 and steam 213 are added and the feed 215 is preheated (e.g., at feed preheating A1/A2/A3). The feed is preheated by the effluent 225 of the oxidation reforming unit 220B and fed to a steam methane reformer at 220A where the feed is passed over a reforming catalyst while being heated by cooling the effluent 225 of a partial oxidation reforming unit 220B. The effluent 221 of the steam reformer at 220A is passed to the partial oxidation reforming unit at 220B where 89 t/h of oxygen 228 from the ASU is added and reacted with the gas stream. The temperature of the effluent 225 exiting the partial oxidation reformer at 220B is 972° C., in embodiments. The 11 t/h hydrogen-rich stream 282 (approximately 76 mol % $H_2$, 24 mol % $N_2$) from the Purge Gas Separation unit 240B is reacted with oxygen 287 to generate a high temperature water stream 288 that is mixed with the partial oxidation reformer product 225. The gas is further reacted over a third reforming catalyst bed at 220C giving a final reformer outlet temperature of effluent 225A of 1071° C. The reforming product 225A is cooled down (e.g., via syngas cooling B1/B2) to close to the mixture dew point before further cooling to 45° C. in a water condensing and removal section (e.g., water condensing B3) to generate an essentially dry syngas stream 234 and a recycle water stream 238. The dried syngas 234 is passed to a syngas compressor C2 where the pressure is increased from 35 to 99 bar. The compressed, dried, syngas 236 is mixed with recycled syngas 244 and preheated (e.g., via syngas heating at A4). The preheated syngas 237 is fed to the methanol reactors at 230B where it is heated to the final reaction temperature and passed over a methanol synthesis catalyst. The methanol reactor effluent 235 is cooled (e.g., by methanol reactor cooling at B4, which is integrated, in this example, into the methanol synthesis reactors of 230B) down to 45° C. where vapor and liquid phases are separated (e.g., in crude methanol separation 240A). The vapor phase 242 is taken to the recycle compressor C3 after taking 35 t/h off as a purge gas stream 205' containing 61 mol % $H_2$, 30 mol % $N_2$, 5 mol % $CO_2$, 1 mol % CO, and 3 mol % $CH_4$. The liquid stream 246 is fed to a degassing column at 240C where it is heated to remove light gases 247' dissolved in the crude methanol stream 246. The degassed crude methanol 247 is fractionated to provide a substantially pure methanol product stream. This is done in this Example 3 via a 2 column sequence where a partial recovery 245A of the methanol is taken in the first column at 240D and the remaining methanol 245B is purified by fractionation in the second column at 240E. The majority of the energy for the distillation column reboilers is provided by heat recovery, in this embodiment. The remaining 11 MW of heat required for the methanol column reboiler(s) is supplied by electric process heaters in this embodiment. Heavy byproducts are purged via a small side stream in the column (not shown). The overhead streams (e.g., 245A/245B) of each of the columns (e.g., at 240D/240E, respectively) are cooled (e.g., in methanol product cooler(s) at B5) to 45° C. before being sent to methanol product handling and storage as methanol product

245C. The water 249A separated from the methanol is also cooled (e.g., in separated water cooling 249B) before discharging as cooled water 249B. Water 238 that was condensed from the syngas 231 is reheated (e.g., at process water heating A5) and recycled to the water addition 216. A small fraction of the water (not shown in the Figures) can be purged from the system to prevent the buildup of impurities. The low pressure purge gas 247' from the methanol degassing column at 240C is sent to an off-gas furnace 290 where it is burned (e.g., with fuel 291 to produce outlet gas 292) to supply 20 MW as heat (e.g., Q26). The purge gas 205' is sent to a Purge Gas Separation system 240B for component recovery. The embodiment in Example 3 employs a cryogenic fractionation of the purge gas 205'. Because the purge gas contains carbon dioxide, the purge gas is preheated and then contacted with a methanation catalyst at methanation 280 where the hydrogen contained in the purge gas reacts with $CO_2$ and CO to form methane and water in methanation product 281. The methanation reaction product is cooled to 40° C. and some water (e.g., removed at 284) is separated. The methanation product 281 is dried over a molecular sieve adsorbent bed (which is regenerated using electrically-heated gas) to remove remaining traces of water to sufficiently low levels suitable for the subsequent cryogenic separation step at 240B. The cryogenic separation system 240B consists of a closed loop vapor compression refrigeration loop, a fractionation column, a stripping column, and integrating heat exchangers among the systems. The refrigerant in the closed loop refrigeration system is nitrogen operating between 43 bar and 2.6 bar of pressure. The gas feed to the Purge Gas Separation system enters a series of heat exchangers where it is cooled from 40° C. to −130° by exchanging heat with the product streams (e.g., 282/283/284) and the refrigerant. The cooled feed stream is fractionated in a fractionation column operating at 32 bar pressure. The bottoms product of the column is high purity methane at −94° C. It is vaporized and re-warmed by sending through the feed-effluent heat exchanger train of the system. The overhead of the column is a mixture of hydrogen and nitrogen. The overhead is cooled from −163° C. to −180° C. by evaporation of the nitrogen refrigerant. The liquid nitrogen is separated from the vapor and pumped back into the column as a refluxing liquid. The vapor overhead contains hydrogen and nitrogen in a 3:1 molar ratio. This stream is warmed by sending through the feed-effluent heat exchanger train of the unit. A liquid side draw is taken from the fractionation column and sent to the stripping column. The stripping column is reboiled by a partial condenser operating on an intermediate stage of the fractionation column. Hydrogen is stripped from the stripping column feed and returned to the fractionation column. The bottom product of the stripping column is liquid nitrogen at −149° C., which is vaporized and reheated in the unit feed-effluent heat exchanger. The nitrogen refrigerant enters the feed-effluent heat exchanger and is cooled along with the process feed stream by the process effluent streams to −70° C. Then it is cooled to −92° C. by the providing the heat for the fractionation column reboiler. Then it is further cooled to −130° C. by heat exchange with the process effluent streams, returning low pressure refrigerant, and a portion (about 14%) of the refrigerant stream that is split from the main stream, expanded to 3 bar in a turboexpander, and fed back through the cold side of the feed-effluent heat exchanger. The remainder of the refrigerant stream is fed through a heat exchanger contacting with the hydrogen product stream and returning refrigerant stream. Then it is passed through a turboexpander to 3.4 bar pressure where additional energy is removed, resulting in a stream containing liquid nitrogen at −185° C. This liquid nitrogen containing stream is vaporized in the overhead condenser of the fractionation column and returned through the feed-effluent heat exchanger train of the system. The refrigerant is compressed to the starting pressure of 43 bar in multiple stages with intercoolers and an aftercooler, completing the cycle. The 14 t/h nitrogen product 283 is about 99% pure with small amounts of residual hydrogen and argon, and can be used as a drying gas or sent elsewhere for other useful purposes, for example to an ammonia synthesis process.

The energy integration of process VI of Example 3 is configured in one specific way, although one skilled in the art could recognize upon reading this disclosure that the same or comparable resulting overall energy balances can be achieved with variations in the configuration, which are to be considered within the scope of this disclosure. The sequence and amount of heat integration between the oxidation reformer at 220B and steam reformer at 220A is considered to be a flexible variable as it is mainly governed by equipment selection and heat integration choices. For example, lesser heat integration between the oxidative reformer at 220A and steam reformer at 220B (e.g., by raising the approach temperature) can increase the external heat requirement of the reforming reaction, where the energy gap could be filled with an electric furnace, in embodiments. Alternately, rather than combusting the hydrogen containing gas 282 to generate water 288, it could simply be recycled to the reformer feed, eliminating the third reforming catalyst bed at 220C but equilibrating the reaction product at a somewhat lower final temperature. Alternatively, the hydrogen containing gas 282 could be sent to a fuel cell to generate electricity for use in the process (as described in Examples 6 and 7 hereinbelow). Similarly, the sequence of reforming by external heating and partial oxidation could be rearranged or divided into a larger number of steps. Likewise, the 11 MW of low temperature electric heat could be applied in a different manner and still achieve the same overall net heat balance. For example electric heaters could be installed for drying gas heating and methanol reaction preheating (e.g., at A4). Rather than combusting (e.g., at off-gas furnace 290) the small amount of low pressure off-gas 247' it could either be recompressed and fed back to the process VI or it could be exported off-site for other useful purposes, such as ammonia production.

The major energy consumers of this Example 3 are (see Table 2, discussed further hereinbelow): (1) heat (e.g., Q4) supplied to the steam reformer at 220A, (2) generation of the steam required for syngas production, (3) methanol distillation (e.g., at 240D/240E), (4) reformer feed preheat (e.g., at feed preheating A1/A2/A3), (5) methanol reactor feed preheat (e.g., at A4), (6) energy (e.g., for work W2) to drive the syngas compressor at C2, and (7) energy (e.g., as work W4) to drive the air separation unit ASU for the production of oxygen 228. Smaller amounts of energy are used for a variety of other purposes. The purge gas separation system 240B requires 12 MW for the electrically-driven refrigeration compressor. A significant amount of the energy used can be obtained by heat exchange with the product streams as they are cooled, most notably the hot syngas (e.g., 225) from the reformer and the product 235 of the methanol reactor at 230B. The external energy inputs are 11 MW of heat supplied by electricity to the methanol distillation (e.g., at 240D/240E), and 89 MW of power required for process drives (e.g., at 270). By reacting the natural gas 221 with oxygen 228 in the oxidation reformer at 220B, by burning hydrogen-rich stream 282, and from the methanol synthesis chemical reaction at 230B a large amount of heat is internally generated within the process VI. 1052 MW of heat is recovered during cooling of the various process streams; of this, 663 MW is transferred internally for other process uses according to process VI of this Example 3 according to this disclosure. A significant amount of the heat is recovered in process VI, however, 378 MW of heat ends up being rejected to cooling water.

Table 2 shows an energy balance for the complete electrification process VI of this Example 3. An amount of 130 MW of renewable electricity is supplied to process VI; this represents a total net energy input to the process of approximately 75% less than in Comparative Example 1. Unlike like in process III of Comparative Example 1, there is no steam system SS for generation of power for process drives 270 in the process VI of this Example 3. An important difference from Comparative Example 1 is that the electrified methanol process VI of Example 3 has very minimal stack losses or steam system losses. Overall 388 MW of energy is rejected in process VI, primarily in cooling, rather than being taken as useful for the process, which is a 45% reduction relative to process III of Comparative Example 1.

Table 3 provides relevant energy use statistics for process VI of this Example 3 according to this disclosure. In Example 3, no natural gas is consumed solely for heat generation. In addition, the amount of natural gas fed to the process is reduced by 8.7% relative to Comparative Example 1. Taken together, the total natural gas consumption of process VI is 20% less than that of Comparative Example 1. The 254,000 tons per year of natural gas saved via process VI can be used elsewhere, for example, without limitation, as a feed for an ammonia synthesis process. A relatively minor amount of $CO_2$ is produced in the process of Example 3, 10,000 tons per year, from combustion of the low pressure off-gases 247' (e.g., at off-gas furnace 290), a 98.6% decrease in $CO_2$ production compared to Comparative Example 1. Net specific total energy consumption of process VI is 30.2 GJ (28.7 MMBTU) per ton of methanol produced, which is 15% less than that of process III of Comparative Example 1. The carbon efficiency of process VI of this Example 3 is 97%, a significant increase over the 77% carbon efficiency of process III of Comparative Example 1.

Comparative Example 2

Comparative Example 2 describes a conventional (e.g., non-electrified) process VII for the production of methanol that does not contain a partial oxidation reactor. Because there is no partial oxidation internal to the process, additional external energy must be supplied. Process VII does not represent a specific operating plant or process, but it is representative of a typical plant or process VII as described hereinbelow with reference to FIG. 9; the design parameters were taken from knowledge of specific plants, as well as literature information on typical process operations. Although variations will be obvious to one skilled in the art upon reading this disclosure, this Comparative Example 2 represents a typical process VII that can be used as a basis for comparing the effects of electrification modifications (of subsequent Examples 4-6) according to embodiments of this disclosure.

The process VII of Comparative Example 2 is configured to produce 5,000 metric tons per day of methanol. If operated for 8,000 hours in a year, this would result in the production of 1.67 million tons of methanol, although variations in downtime due to upsets and maintenance could increase or reduce this output. This size is typical of contemporary large methanol plants.

Figure 9:
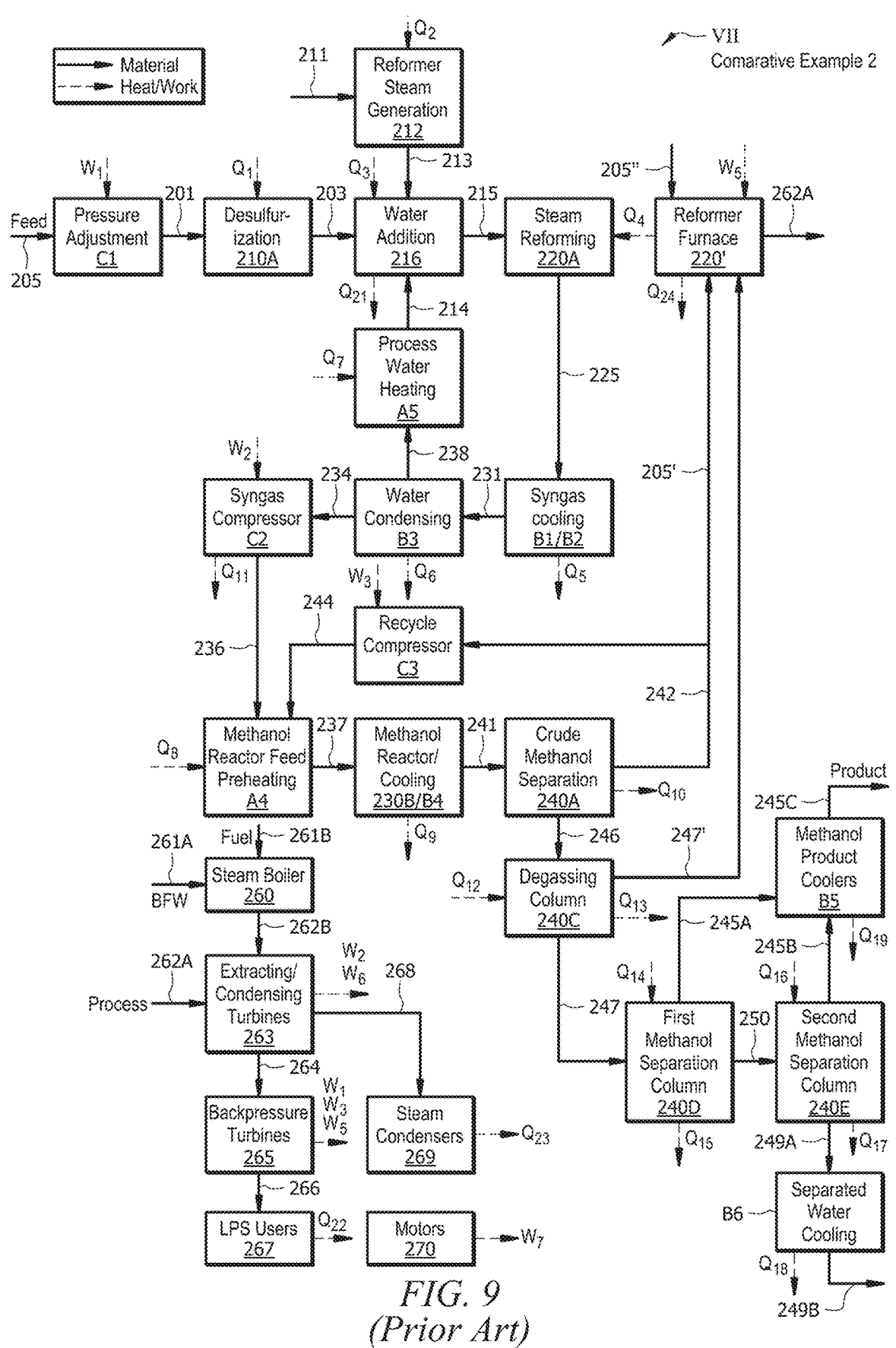
FIG. 9 shows a block flow diagram of a conventional methanol synthesis plant or process VII, discussed in Comparative Example 2 of this disclosure.

As shown in FIG. 9 (which has been simplified to show only the essential features of the process VII of this Comparative Example 2), 141 metric tons per hour (t/h) of natural gas feed 205 are fed to the feed pretreatment section where it underdoes pressure adjustment at C1 and desulfurization at 210A (hydrogen addition not shown) after heating (e.g., at feed preheating A1) to the desired desulfurization temperature (e.g., 385° C.). Water 214 and steam 213 are added to provide a reforming feed 215 (e.g., with a steam to carbon molar ratio of 2.8) and the feed 215 is preheated (e.g., at feed preheating A1/A2/A3) and fed to a steam methane reformer at 220A where the feed is passed over a reforming catalyst while being heated in the radiant section of a reforming furnace 220' (e.g., to 860° C.). The reforming product 225 is cooled down (e.g., at syngas cooling B1/B2) to close to the mixture dew point before further cooling to 45° C. in a water condensing and removal section (e.g., water condensing B3) to generate an essentially dry syngas stream 234 and a recycle water stream 238. The dried syngas 234 passes to a syngas compressor C2 where the pressure is increased from 15 to 99 bar. The compressed, dried, syngas 236 is mixed with recycled syngas 244 and preheated (e.g., at syngas heating A4) to 165° C. The preheated syngas 237 is fed to the methanol reactors at 230B where it is heated to the final reaction temperature and passed over a methanol synthesis catalyst. The effluent 235 of the methanol synthesis reaction, which is exothermic, is cooled by water (e.g., at cooling B4, which is integrated, in this example, into the methanol synthesis reactors of 230B) which is vaporized, sent to the water addition section 216 and condensed to provide the heat required for the water addition to the feed. The cooled methanol reactor effluent 241 is cooled down to 45° C. (e.g., at crude methanol separation 240A) where vapor and liquid phases are separated. The vapor phase 242 is passed to the recycle compressor C3 after taking 51 t/h off as a purge gas stream 205'. This purge gas 205' from the synthesis loop is combined with the low pressure off gases 247' to provide a 54 t/h stream containing 79 mol % H$_2$, 11 mol % CH$_4$, 7 mol % N$_2$, and 3 mol % other compounds, which is burned in the reformer furnace 220' for fuel, along with 11.7 t/h of natural gas 205''. The liquid stream 246 is fed to a degassing column at 240C where it is heated to remove light gases 247' dissolved in the crude methanol stream 246. The degassed crude methanol 247 is fractionated to provide a substantially pure methanol product stream. This is effected in this Comparative Example 2 via a 2 column sequence where a partial recovery 245A of the methanol is taken in the first column at 240D and the remaining methanol 245B is purified by fractionation in the second column at 240E. Heavy byproducts are purged via a small side stream in the column (not shown). The overhead streams (e.g., 245A/245B) of each of the columns (e.g., 240D/240E, respectively) are cooled (e.g., at methanol product cooler(s) B5) to 45° C. before being sent to methanol product handling and storage or the like as methanol product 245C. The water 249A separated from the methanol is also cooled (e.g., at separated water cooling B6) before discharging as cooled water 249B. Water 238 that was condensed from the syngas 231 is reheated (e.g., at process water heating A5) and recycled to the water addition 216. A small fraction of the water (not shown in the Figures) is purged from the system to prevent the buildup of impurities.

The major energy consumers of process VII of this Comparative Example 2 are (see Table 2, discussed further hereinbelow): (1) heat (e.g., Q4) supplied to the steam reformer, (2) generation of the steam required as feed for syngas production, (3) methanol distillation (e.g., at 240D/240E), (4) methanol reactor feed preheat (e.g., at syngas heating A4), (5) reformer feed preheat (e.g., at feed preheating A1/A2/A3), and (6) energy (e.g., for work W2) to drive the syngas compressor (e.g., at C2). Smaller amounts of energy are used for a variety of other purposes. As is common practice, very little electricity is consumed in process VII of this Comparative Example 2, primarily for some smaller pumps; the electrical demand for process users is only 1.7 MW. A significant amount of the energy used can be obtained by heat exchange with the product streams as they are cooled, most notably the hot syngas (e.g., 225) from the reformer at 220A and the effluent 235 from the methanol reactor(s) at 230B. The remaining energy is supplied as combusted fuels in the reforming furnace 220' and a steam boiler 260. The reforming furnace 220' serves multiple purposes, supplying heat for the steam reforming reaction from the radiant section, providing some feed preheating in the convection section, and supplying heat in the convection section for use in generation of high pressure steam 262A. Cooling of the syngas is also utilized in the generation of high pressure steam 262A. The remaining high pressure steam 262B is generated by the steam boiler 260. The high pressure steam 262A/262B is directed through a system of steam turbines (e.g., 263/265) to drive the large power users of the plant. In Comparative Example 2 the syngas charge compressor C2 and the cooling water pumps are partly extracting plus condensing turbines 263. The gas feed booster compressor, reformer air/flue gas fans, and the syngas recycle compressor C3 are backpressure turbines 265 that exhaust 231 t/h low pressure steam 266 that is used for heating in the process VII. In Comparative Example 2, there are two major locations which utilize external sources of energy. The first is in the reformer furnace 220' at steam reforming 220A, which consumes 11.7 t/h of natural gas 205'' with a contained chemical energy (high-heating value, or HHV) of 157 MW plus the process off gases (e.g., purge gas 205' and light gases 247') with contained chemical energy (high-heating value, or HHV) of 781 MW. In this embodiment, the remaining energy is supplied by a steam boiler 260 that converts 21.8 t/h of natural gas fuel 261B with a contained chemical energy of 290 MW to produce high pressure (HP) steam 262B from BFW 261A. How to most efficiently allocate this energy to the various consumers of energy in the process with the highest efficiency is an engineering problem that can be addressed by one of skill in the art upon reading this disclosure via careful matching of temperatures, types of energy, and energy content. Some of the energy can be transferred directly via heat exchange, while some can be converted to steam that can either be used for heat exchange or to do mechanical work, such as drive a compressor. In Comparative Example 2 a typical strategy has been adopted for matching heat inputs and outputs, but other arrangements are possible, as will be obvious to one skilled in the art. The use of combustion furnaces to supply the external energy input needed for the process comes with a concomitant disadvantage—the stack or flue gas from these furnaces contains energy that cannot be usefully recovered because of its low temperature. For example, in the process of Comparative Example 2, this unrecovered energy, sometimes referred to as stack losses, amounts to 177 MW at the reformer furnace 220' and 58 MW at the steam boiler 260. Energy is also lost in several process steps, primarily in water condensing from various points such as from the syngas (e.g., at water condensing B3) because the temperature is too low for returning the energy to useful purposes.

Comparative Example 2 shows the energy integration configuration chosen for the purposes of this example. One with skill in the art would recognize a number of ways the heat recovery of the syngas cooling and reformer stack could be configured for raising the high pressure steam. For example, the ratios of how much energy is supplied in water preheating, vaporization, and steam superheating could be reassigned among the units according to the design and equipment configuration. Likewise the steam heat raised in the methanol synthesis reactor at 230B could be used for distillation heating (e.g., at 240D/240E) rather than reformer water and steam heating (e.g., at process water heating A5 and/or reformer steam generation 212). These and other heat integration choices are known art and for various reasons different choices could be taken by one skilled in methanol plant design upon reading this disclosure; such variations are intended to be within the scope of this disclosure.

Table 2 shows the energy balance for the process VII of this Comparative Example 2. As seen in Table 2, an amount of 1228 MW of chemical energy is supplied through the combustion of process off-gas (e.g., purge gas 205' and light gases 247') and natural gas (e.g., 205") in the reformer furnace 220' of steam reformer at 220A and fuel/methane 261B to the steam boiler 260; this represents all but 2 MW of the total energy input to the process VII that is supplied from external sources. Including the heat supplied by the reforming furnace 220', a large amount of heat (1991 MW) is available within the process. A total of 775 MW is recovered from process sources; however, because of the available heat supplied by the steam turbines (e.g., 263/265), as well as the temperature and enthalpy requirements of the process, 455 MW of heat is rejected to cooling water. Additionally the steam system rejects 272 MW of heat to cooling water in the condensing turbines (e.g., 269). Furnace stack losses total 235 MW. Overall 975 MW of energy, 49% of the total heat available, is rejected rather than being taken as useful for the process.

Table 3 provides relevant energy use statistics for the process VII of this Comparative Example 2. As seen in the data in Table 3, the carbon efficiency of process VII, defined by the carbon contained in the product methanol (e.g., methanol product 245C) divided by the carbon of the total natural gas consumed, is 68.4%. The combustion of this fuel results in the atmospheric emissions of 132 t/h of $CO_2$, or 1.06 million tons of $CO_2$ annually. Net specific energy consumption is 40.1 GJ (38.1 MMBTU) per ton of methanol produced in process VII. Net specific energy consumption includes the energy content of the natural gas feedstock for making methanol plus the external energy supplied in other forms such as electricity and natural gas for fuel.

Example 4

Example 4 is a complete electrification process VIII, according to this disclosure, comprising a substantially complete electrification of the methanol process VII described in Comparative Example 2. In Example 4, the energy supplied to the external steam boiler and the reformer furnace is replaced with renewable electricity, which powers all pumps and compressors, supplies the energy for steam reforming, and provides some process heat. As a result, there is no external steam system in Example 4. There is also no flue gas, and the only $CO_2$ emitted comes from a small amount of $CO_2$ released from waste water streams. The purge gas that was burned in Comparative Example 2 to provide heat is exported in this example for other uses.

Figure 10:
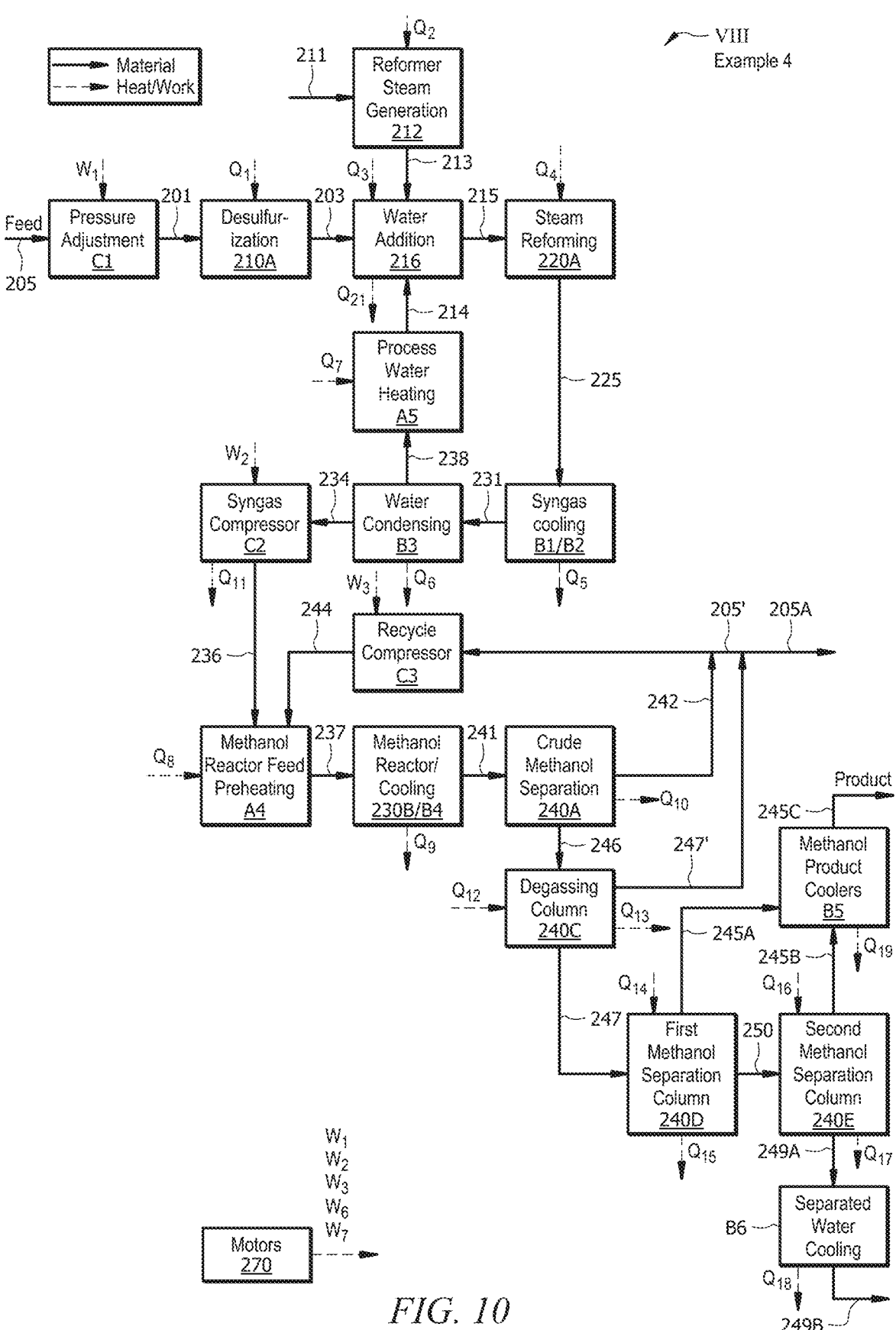
FIG. 10 shows a block flow diagram of an exemplary substantially completely electrified methanol synthesis plant or process VIII, according to the embodiment of Example 4 of this disclosure.

The key elements of this electrified plant or process VIII are shown in FIG. 10. An amount of 141 metric tons per hour (t/h) of natural gas feed 205 is fed to the feed pretreatment section where it underdoes pressure adjustment at C1 and desulfurization at 210A after heating (e.g., at feed preheating A1) to the desired desulfurization temperature (e.g., 385° C.). Water 214 and steam 213 are added to produce a reforming feed 215 (e.g., with a steam to carbon molar ratio of 2.8) and the feed 215 is preheated (e.g., at feed preheating A1/A2/A3). The feed is preheated by the effluent 225 of the steam reformer at 220A while being fed to the steam reformer at 220A. The feed 215 passes over a reforming catalyst bed that is electrically heated in this embodiment. The temperature of the effluent 225 exiting the reformer 220A is 860° C. The reforming product 225 is cooled down (e.g., by heat exchange at syngas cooling B1/B2) to close to the mixture dew point before further cooling to 45° C. in a water condensing and removal section (e.g., at water condensing B3) to generate an essentially dry syngas stream 234 and a recycle water stream 238. The dried syngas 234 passes to a syngas compressor C2 where the pressure is increased from 15 to 99 bar. The compressed, dried, syngas 236 is mixed with recycled syngas 244 and preheated (e.g., at methanol reactor feed preheating A4) to 165° C. The preheated syngas 237 is fed to the methanol reactors at 230B where it is heated to the final reaction temperature and passed over a methanol synthesis catalyst. The methanol reactor effluent 235 is cooled down (e.g., via methanol reactor cooling B4, which is integrated, in this example, into the methanol synthesis reactors of 230B) and crude methanol separation 240A to 45° C. where vapor and liquid phases are separated. The vapor phase 242 is passed to the recycle compressor C3 after taking 51 t/h off as a purge gas stream 205'. The liquid stream 246 is fed to a degassing column 240C where it is heated to remove light gases 247' dissolved in the crude methanol stream 246. The purge gas 205' from the synthesis loop combined with the low pressure off gases 247' amounts to 54 t/h. The total purge gas 205A is a valuable product containing 79 mol % $H_2$, 11 mol % $CH_4$, 7 mol % $N_2$, and 3 mol % other compounds can be utilized as a product for other useful purposes with or without further separation, as will be apparent to those of skill in the art upon reading this disclosure. Useful purposes can include, without limitation, ammonia production, (substantially) pure hydrogen production, hydrogenation reactions, and the production of electricity, among other uses. The degassed crude methanol 247 is fractionated to provide a substantially pure methanol product stream. This is effected in this Example 4 in a two column sequence where a partial recovery 245A of the methanol is taken in the first column at 240D and the remaining methanol 245B is purified by fractionation in the second column at 240E. The majority of the energy (e.g., Q14/Q16) for the distillation column reboilers is provided by heat recovery. The remaining 75 MW of heat required for the methanol column reboiler(s) is supplied by electric process heaters in this embodiment. Heavy byproducts are purged via a small side stream in the column (not shown). The overhead streams (e.g., 245A/245B) of each of the columns (e.g., 240D/240E) are cooled (e.g., at methanol product cooler(s) B5) to 45° C. before being sent to methanol product handling and storage or the like as methanol product 245C. The water 249A separated from the methanol is also cooled (e.g., at separated water cooling B6) before discharging as cooled water 249B. Water 238 that was condensed from the syngas 231 is reheated (e.g., at process water heating A5) and recycled to the water addition 216. A small fraction of the water (not shown in the Figures) can be purged from the system to prevent the buildup of impurities. In this embodiment, the recycled water is converted back into medium pressure steam by an electrically powered steam boiler supplying 71 MW heat.

How to most efficiently allocate energy from the various sources of energy to the various consumers of energy in the process with the highest efficiency is an engineering problem that can be addressed by one of skill in the art upon reading this disclosure via careful matching of temperatures, types of energy, and energy content. In Example 4 a logical strategy has been adopted for matching heat inputs and outputs, but the same overall energy balance can be achieved with other arrangements, as will be obvious to one skilled in the art upon reading this disclosure. The sequence and amount of heat integration between the syngas cooling and electric furnace is considered to be a flexible variable as it is mainly governed by equipment selection and heat integration choices. For example, tighter heat integration between feed 215 and effluent 225 of the steam reformer at 220A (by lowering the approach temperature, for example) can reduce the amount of electricity used in the reforming reaction. Similarly, the 75 MW of low temperature electric heat could be applied in a different manner and still achieve the same overall net heat balance. For example electric heaters can be installed for the heat required in the water addition step 216 of the process VIII, thus saving the higher temperature methanol reactor heat for the column reboilers (e.g., at 240D/240E), which could be a capital investment saving alternative due to having higher temperature driving forces, and therefore less heat exchanger area in the column reboilers.

The major energy consumers of process VIII of this Example 4 are (see Table 2, discussed further hereinbelow): (1) heat (e.g., Q4) supplied to the steam reformer, (2) generation of the steam required as feed for syngas production, (3) methanol distillation (e.g., at 240D/240E), (4) reformer feed preheat (e.g., at feed reheating A1/A2/A3), (5) methanol reactor feed preheat (e.g., at syngas heating A4), (6) energy (e.g., for work W2) to drive the syngas compressor (e.g., at C2). Smaller amounts of energy are used for a variety of other purposes. A significant amount of the energy used can be obtained by heat exchange with the product streams as they are cooled, most notably the hot syngas (e.g., 225) from the reformer at 220A and the effluent 235 from the methanol reactor at 230B. The external energy inputs are 415 MW of heat supplied by electricity to the steam reforming section at 220A, 75 MW of heat supplied by electric heaters to the distillation section (e.g., at 240D/240E), 71 MW of heat supplied for reforming steam generation (e.g., at 212), and 90 MW of power required for process drives (e.g., at 270). A large amount of heat is internally generated within process VIII, amounting to 1627 MW of heat. Of this, 651 MW are transferred internally during the cooling of the various process streams according to this Example 4 according to this disclosure. Although a significant amount of heat is recovered in the process, 413 MW of heat ends up being rejected to cooling water.

Table 2 shows the energy balance for the complete electrification process VIII of this Example 4. 687 MW of renewable electricity is supplied to process; this represents a total net energy input to the process of approximately 44% less than process VII in Comparative Example 2. Unlike in Comparative Example 2, there is no steam system in Example 4 beyond the steam used as diluent in the feed. Another difference from Comparative Example 2 is that the fully electrified methanol process does not have stack losses or steam system losses. Overall 448 MW of energy is rejected rather than being taken as useful for the process, which is a 54% reduction relative to process VII of Comparative Example 2. The off-gas product (e.g., 205A) has an energy content in terms of higher heating value of 781 MW.

Table 3 provides relevant energy use statistics for process VIII of Example 4 according to this disclosure. In Example 4, natural gas is consumed only as a chemical feedstock. The carbon efficiency of the process is 84.7%, an improvement of approximately 16.3% relative to process VIII of Comparative Example 2. A relatively minor amount of $CO_2$ is produced, 13,000 tons per year, from decomposition of dissolved organics in the wastewater stream, which amounts to 1% of the $CO_2$ production of process VII of Comparative Example 2. The natural gas consumption by process VIII is 19% less than that of process VII of Comparative Example 2. The 268,000 tons per year of natural gas saved by process VIII can be used elsewhere, for example, without limitation, as a feed for an ammonia synthesis process and/or as feed for the or another methanol synthesis process. Net specific energy consumption (calculated as the energy content of the natural gas feedstock for making methanol plus the external energy supplied as electricity less the energy content of the exported purge gases, per ton of methanol produced) is 30.8 GJ per ton of methanol, which is 23% lower than in the process VII of Comparative Example 2.

Example 5

The process VIII in Example 4 illustrates that, unexpectedly, some process variables that were formerly at optimal conditions for the methanol plant/process VII in Comparative Example 2 can benefit from re-optimization in the electrified version of the plant. In a process IX of this Example 5, having the same physical layout as shown for Example 4 in FIG. 10, the optimal purge gas rate for the process IX from the methanol synthesis loop was found to be reduced from 51 to 47 t/h. This provides an increase in the recycle gas flow 244 to the methanol synthesis reactor at 230B. Table 2 provides the energy balance details of process IX of this Example 5. Electrical inputs were increased by 20 MW to 707 MW. Table 3 provides relevant energy use statistics for process IX of this Example 5. The carbon efficiency is increased to 85.9%, which is 1.1 percentage points higher than in process VIII of Example 4. The specific natural gas consumption of this process IX is 1.9 t/h, or 15,000 tons per year, less than process VIII of Example 4. The net specific total energy consumption of this process IX is 31.2 GJ per ton of methanol produced, which is 0.4 GJ/ton more than that of process VIII of Example 4 but is still 22% less than that of Comparative Example 2. Example 5 shows that different modes of electrification according to this disclosure may be desirable depending on what inputs are to be optimized. Process IX of Example 5 is slightly less energy efficient than Process VIII of Example 4, but it consumes less natural gas and has a higher carbon efficiency.

Example 6

Figure 11:
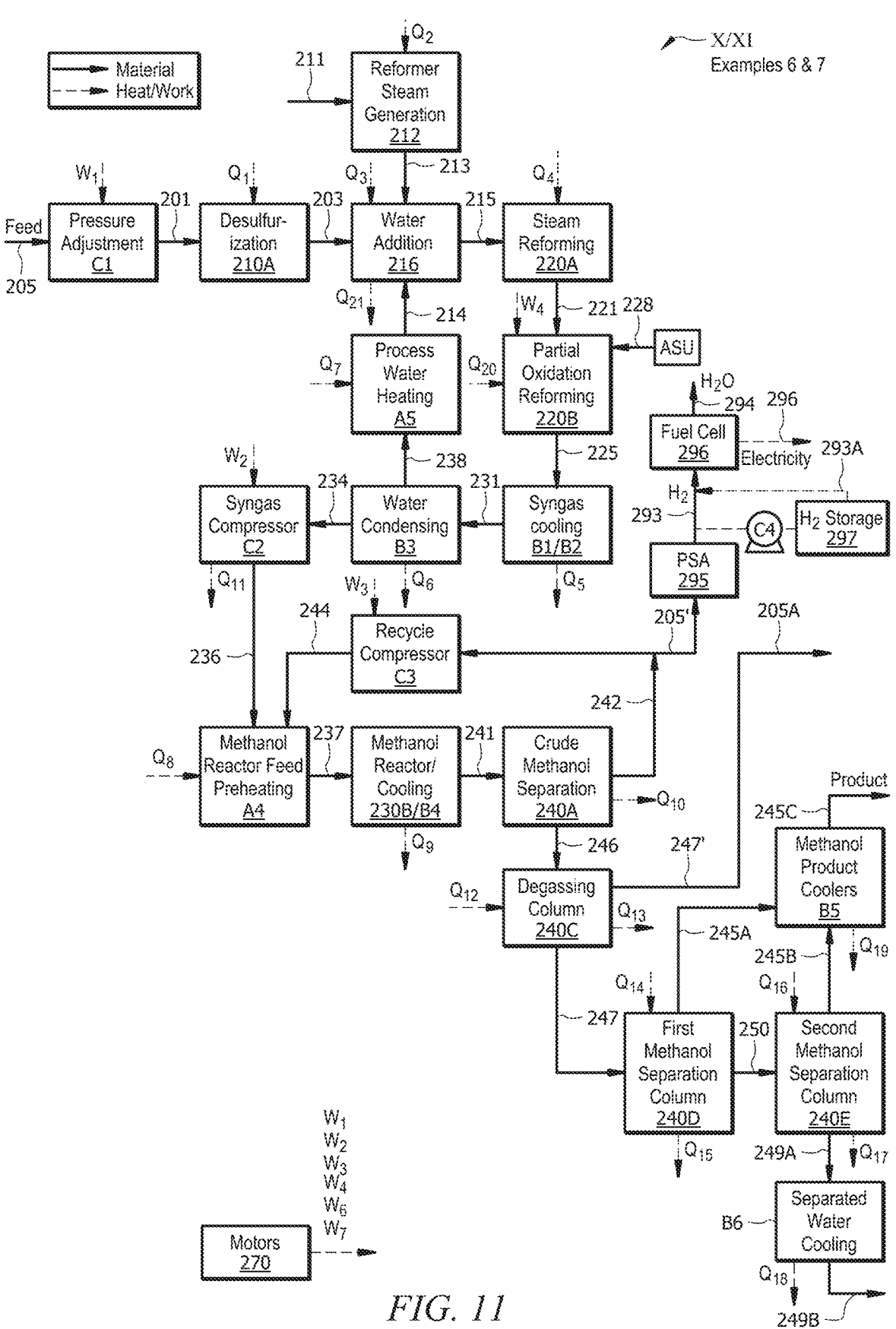
FIG. 11 shows a block flow diagram of exemplary substantially completely electrified methanol synthesis plant or processes X and XI, according to the embodiments of Examples 6 and 7 of this disclosure.

As depicted in FIG. 11, a process X comprises a pressure swing adsorption (PSA) gas separation unit 295 and a fuel cell 296 added to the process V described in Example 2. PSA 295 is operable to purify the purge gas stream 205'; this PSA unit 295 recovers 80% of the 3.37 t/h of hydrogen available. The resulting 2.7 t/h of purified hydrogen 293 is fed to a fuel cell 296, where the hydrogen is converted to water 291 and electricity 296 with an electrical efficiency of 45%, giving continuous production of 48 MW of electricity. This electricity is used to supply approximately 27% of the 180 MW of electricity required for the process X (see Table 2.)

Example 7

As depicted via dashed lines in FIG. 11, a process XI according to this disclosure comprises a compressor C4 and storage vessel 297 added to the process IX of Example 6. As noted in Example 6 hereinabove, pressure swing adsorption (PSA) gas separation unit 295 is operable to purify the purge gas stream 205'; this PSA unit 295 recovers 80% of the 3.37 t/h of hydrogen available. The resulting 2.7 t/h of purified hydrogen 293 is compressed at C4 and stored in storage vessel 297 for use when the availability of renewable electricity is lower, or when it is more expensive. When needed, the stored hydrogen 293A is combined with the hydrogen 293 being produced at that time by the process XI, and both are converted to electricity using the fuel cell 296. When to use the stored hydrogen for electricity production will be determined by a variety of factors, as will be appreciated by those of skill in the art. As one possibility, if some renewable electricity is available on a diurnal basis, 32.4 tons hydrogen could be collected, compressed at C4 and stored at 297 over a twelve hour period. When released over the next twelve hours and combined via stored hydrogen stream 293A with the 2.7 t/h hydrogen 293 still being produced by the process IX, approximately 96 MW of electricity can be available continuously for the twelve hours. This electricity would supply approximately 53% of the 180 MW of electricity required for the operation of the process XI.

TABLE 2

| CE 1 drawing label | Example (Process) | CE 1 (III) (values in MW) | 1 (IV) (values in MW) | 2 (V) (values in MW) | 3 (VI) (values in MW) | CE 2 (VII) (values in MW) | 4 (VIII) (values in MW) | 5 (IX) (values in MW) |
|---|---|---|---|---|---|---|---|---|
| | Energy inputs to the battery limits Fired fuels | | | | | | | |
| 25 | Process gases | 252 | 252 | 0 | 24 | 781 | 0 | 0 |
| 28 | Reformer NG | 138 | 138 | 0 | 0 | 157 | 0 | 0 |
| 29 | BoilerNG | 130 | 0 | 0 | 0 | 290 | 0 | 0 |
| | Electricity | 2 | 24 | 180 | 105 | 2 | 687 | 707 |
| | Total external energy inputs Process Heat sinks | 522 | 414 | 180 | 130 | 1230 | 687 | 707 |
| | Heat rejection to cooling water | 385 | 385 | 363 | 378 | 455 | 413 | 438 |
| | High pressure steam generation | 331 | 331 | 0 | 0 | 322 | 0 | 0 |
| Q4 | Steam Reformer | 164 | 164 | 164 | 154 | 520 | 520 | 513 |
| Q3 | Saturator | 126 | 126 | 126 | 136 | 107 | 107 | 67 |
| Q16 | Second methanol column reboiler | 98 | 98 | 98 | 98 | 98 | 98 | 98 |
| Q14 | First methanol column reboiler | 89 | 89 | 89 | 89 | 90 | 90 | 90 |
| Q4 | Saturator to reformer feed heat | 80 | 80 | 80 | 78 | 114 | 114 | 106 |
| Q8 | Methanol reactor feed preheat | 52 | 52 | 52 | 50 | 79 | 79 | 151 |
| Q1 | Gas to desulfurization preheat | 28 | 28 | 28 | 26 | 33 | 33 | 32 |
| Q12 | Degassing column reboiler | 23 | 23 | 23 | 26 | 20 | 20 | 26 |
| Q2 | Medium pressure steam generation | 22 | 22 | 22 | 2 | 113 | 113 | 170 |
| Q20 | Oxygen preheating | 7 | 7 | 7 | 8 | | | |
| Q7 | Process water preheating | 4 | 4 | 4 | 5 | 41 | 41 | 33 |
| | Methanation reactor preheat | | | | 2 | | | |
| | Drying gas heating | | | | 1 | | | |
| | Total process heat sinks Process Heat sources | 1410 | 1410 | 1056 | 1052 | 1991 | 1627 | 1724 |
| Q5 | Syngas cooling | 324 | 324 | 324 | 361 | 290 | 290 | 286 |
| | Reformer furnace (heat supplied) | 320 | 320 | 22 | 0 | 761 | 415 | 417 |
| Q10 | Methanol reactor effluent | 176 | 176 | 176 | 171 | 239 | 239 | 357 |
| Q9 | Methanol reactor cooling | 133 | 133 | 133 | 136 | 107 | 107 | 67 |
| Q22 | Low pressure steam use | 131 | 131 | 0 | 0 | 166 | 0 | |
| Q17 | Second methanol column condenser | 110 | 110 | 110 | 110 | 111 | 111 | 111 |
| Q6 | Syngas condensing | 93 | 93 | 93 | 92 | 174 | 174 | 172 |
| Q15 | First methanol column condenser | 74 | 74 | 74 | 73 | 74 | 74 | 74 |
| Q11 | Syngas compressor intercoolers | 15 | 15 | 15 | 15 | 47 | 47 | 46 |
| Q13 | Degassing column condenser | 10 | 10 | 10 | 13 | 7 | 7 | 14 |
| Q21 | Desulfurization to sat gas cooling | 9 | 9 | 9 | 9 | | | |
| Q19 | Methanol product cooler 1 | 7 | 7 | 7 | 7 | 7 | 7 | 7 |
| Q18 | Separated water cooling | 4 | 4 | 4 | 4 | 5 | 5 | 5 |
| Q19 | Methanol product cooler 2 | 2 | 2 | 2 | 2 | 2 | 2 | 2 |
| Q6 | Syngas process waste water cooling | 2 | 2 | 2 | 2 | 1 | 1 | 7 |
| | Low temp. electric heat supplied | 0 | 0 | 75 | 11 | | 76 | 59 |
| | Medium temp electric heat supplied | | | | | | 71 | 101 |
| | Off-gas furnace | | | | 20 | | | |
| | Methanated product cooling | | | | 8 | | | |
| | Methanation reaction cooling | | | | 6 | | | |
| | Refrigeration gas coolers | | | | 13 | | | |
| | Total process heat sources | 1410 | 1410 | 1056 | 1052 | 1991 | 1627 | 1724 |

TABLE 2-continued

| CE 1 drawing label | Example (Process) | CE 1 (III) (values in MW) | 1 (IV) (values in MW) | 2 (V) (values in MW) | 3 (VI) (values in MW) | CE 2 (VII) (values in MW) | 4 (VIII) (values in MW) | 5 (IX) (values in MW) |
|---|---|---|---|---|---|---|---|---|
| | Power requirements | | | | | | | |
| W2 | Syngas charge compressor | 30 | 30 | 30 | 30 | 69 | 69 | 68 |
| W4 | Oxygen production | 23 | 23 | 23 | 26 | | | |
| W8 | Gas separation system | | | | 12 | | | |
| W6 | Cooling water circuit | 12 | 10 | 7 | 7 | 14 | 8 | 9 |
| W1 | NG feed booster compressor | 9 | 9 | 9 | 8 | 5 | 5 | 5 |
| W5 | Reformer air fans | 4 | 4 | 0 | 0 | 9 | 0 | 0 |
| W3 | Syngas recycle compressor | 3 | 3 | 3 | 3 | 6 | 6 | 11 |
| W7 | Other pumps, misc. | 2 | 2 | 2 | 2 | 2 | 2 | 2 |
| | Total power requirements | 83 | 81 | 74 | 89 | 105 | 90 | 95 |
| | Steam system | | | | | | | |
| | Energy in the steam | 435 | 331 | 0 | 0 | 554 | 0 | 0 |
| | Work extracted | 81 | 59 | 0 | 0 | 103 | 0 | 0 |
| Q22 | Heat extracted | 131 | 131 | 0 | 0 | 166 | 0 | 0 |
| Q23 | Turbine condensate | 213 | 132 | 0 | 0 | 272 | 0 | 0 |
| | Other losses | 10 | 10 | 0 | 0 | 13 | 0 | 0 |
| | Total steam losses | 223 | 142 | 0 | 0 | 285 | 0 | 0 |
| | Losses | | | | | | | |
| | Process | 385 | 385 | 363 | 378 | 455 | 413 | 438 |
| | Steam system | 223 | 142 | 0 | 0 | 285 | 0 | 0 |
| | Reformer stack | 71 | 71 | 0 | 0 | 177 | 0 | 0 |
| | Boiler/Furnace stack | 26 | 0 | 0 | 5 | 58 | 0 | 0 |
| | Electrical | 0 | 1 | 9 | 5 | 0 | 34 | 35 |
| | Total energy losses | 705 | 599 | 372 | 388 | 975 | 448 | 473 |

TABLE 3

| Example (Process) | units | CE 1 (III) | 1 (IV) | 2 (V) | 3 (VI) | CE 2 (VII) | 4 (VIII) | 5 (IX) |
|---|---|---|---|---|---|---|---|---|
| Carbon efficiency | % | 76.8 | 82.0 | 88.2 | 96.6 | 68.4 | 84.7 | 85.9 |
| $CO_2$ emissions | t/yr | 691,000 | 504,000 | 12,000 | 10,000 | 1,056,000 | 13,000 | 13,000 |
| Net specific energy consumption | GJ/t | 35.8 | 33.9 | 29.9 | 30.2 | 40.1 | 30.8 | 31.2 |

Example 8

Figure 12:
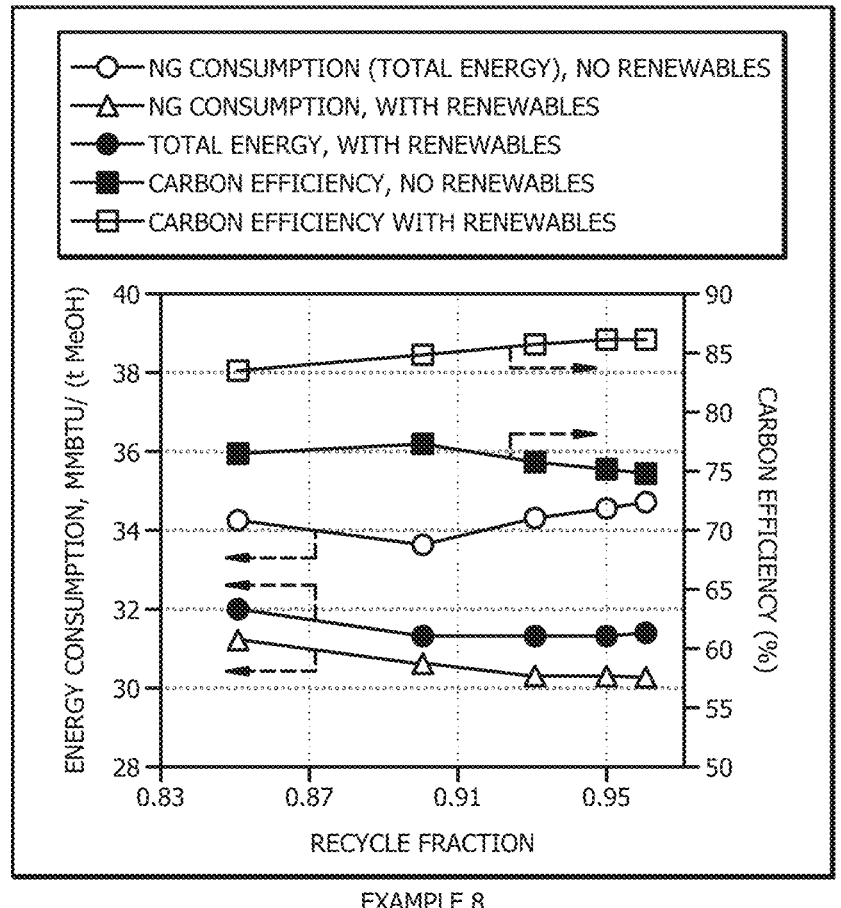
FIG. 12 is a schematic depicting the carbon efficiency, natural gas consumption, and total energy consumption when using renewable energy as a function of the process variable of the recycle fraction of syngas returned to the methanol synthesis reactor in Example 8.

It has been found that for the methanol synthesis process, some process optimization points may be shifted when using renewable energy. As an example, FIG. 12 shows the effect of the recycle fraction (the fraction of the total recycle stream 242 that is returned to the methanol synthesis reactor 230B instead of being purged 205') on carbon efficiency, natural gas consumption, and total energy consumption. As FIG. 12 shows, there is a maximum in carbon efficiency and a minimum in energy consumption at a recycle ratio of approximately 0.9 when using natural gas as the energy source. In contrast, when using renewable electricity energy, the carbon efficiency monotonically increases as the recycle fraction increases. It has been unexpectedly discovered that, when using renewable electricity for the recycle compressor, the optimal point in total energy consumption is shifted to a different point. From FIG. 12, it can be seen that a recycle fraction of 0.95 or greater results in low total energy consumption, high carbon efficiency, and low natural gas consumption when renewable energy is used. This recycle fraction corresponds to a recycle gas/purge gas ratio of 19:1.

Without wishing to be limited by theory, this may be because of the difference in efficiency of the power supply side of the electrically driven compressor system of this disclosure compared to a conventional steam driven compressor system.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Disclosure Part I

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A methanol synthesis plant comprising: a feed pretreating section operable to pretreat a feed stream comprising LPG, naphtha, biogas, methane, ethane, propane, butane, naphtha boiling range components, coal, petcoke, or a combination thereof; a synthesis gas (syngas) generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream; a methanol synthesis section comprising one or more methanol synthesis reactors operable to produce a synthesis product comprising methanol; and/or a methanol purification section operable to remove at least one component from the synthesis product to provide a purified methanol product; wherein the methanol synthesis plant is configured such that, relative to a conventional methanol synthesis plant, more of the net energy required by the methanol synthesis plant, the feed pretreating section, the syngas generation section, the methanol synthesis section, the methanol purification section, or a combination thereof, is provided by a non-carbon based energy source, a renewable energy source, and/or electricity.

B: A methanol synthesis plant comprising: a feed pretreating section operable to pretreat a feed stream comprising LPG, naphtha, biogas, methane, ethane, propane, butane, naphtha boiling range components, coal, petcoke, or a combination thereof; a syngas generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream; a methanol synthesis section comprising one or more methanol synthesis reactors operable to produce a synthesis product comprising methanol; and/or a methanol synthesis section comprising one or more methanol synthesis reactors operable to produce a synthesis product comprising methanol; and/or a methanol purification section operable to remove at least one component from the synthesis product to provide a purified methanol product; wherein the methanol synthesis plant is configured such that a majority of the net energy required by the methanol synthesis plant, the feed pretreating section, the syngas generation section, the methanol synthesis section, the methanol purification section, or a combination thereof, is provided by electricity.

Each of embodiments A and B may have one or more of the following additional elements: Element 1: wherein the non-carbon based energy source comprises electricity. Element 2: wherein the electricity is produced from a renewable energy source. Element 3: wherein the renewable energy source comprises wind, solar, geothermal, hydroelectric, wave, tidal, nuclear or a combination thereof. Element 4: wherein a desired syngas generation temperature within at least one of the one or more reactors can be attained without externally (e.g., in a furnace) combusting a dedicated fuel, a carbon-based fuel, or a fossil fuel. Element 5: wherein the one or more reactors are heated to the desired syngas generation temperature via heating from electricity or renewable electricity and including associated convective, conductive, radiant or other heat transfer means. Element 6: wherein the one or more reactors are heated resistively or inductively. Element 7: wherein: other than the production of steam for use in the one or more reactors, steam is not utilized as a primary energy transfer medium; no steam is utilized for mechanical work; and/or a majority, some, or all of the steam utilized in the one or more reactors, one or more, a majority, or all steam turbines of the plant, or a combination thereof is produced electrically and/or without combusting a fossil fuel. Element 8: wherein the pretreating section, the syngas generation section, the methanol synthesis section, the methanol purification section, or a combination thereof comprises one or more compressors, and wherein at least 10, 20, 30, 40, 50, 60, 70, 80, 90, or 100% or a majority of the one or more compressors are configured for non-gas-driven operation, non-steam driven operation, and/or for operation with electrically-produced steam. Element 9: wherein at least one of the one or more compressors is configured for bifunctional operation (or 'dual drive') via both electric motor-driven and gas-driven or both electric motor-driven and steam driven operation, such that configuration of the plant enables operation of the one or more compressors via renewable electricity or steam produced from renewable electricity, when available, and operation via non-renewably produced steam or combustion, when renewable electricity is not available. Element 10: comprising dual compressors for one or more compression step of the feed pretreating section, the syngas generation section, the methanol synthesis section, the methanol purification section, or a combination thereof, such that the compression step can be effected via a first of the dual compressors that is online when a second of the dual compressors is offline, and vice versa, wherein the first of the dual compressors is electric motor-driven, and the second of the dual compressors is steam-driven or combustion-driven, such that configuration of the plant enables operation of the one or more compressors via renewable electricity or steam produced from renewable electricity, when available, and operation via non-renewably produced steam or combustion, when renewable electricity is not available. Element 11: comprising apparatus for cooling or heating a process stream, the one or more reforming reactors, the one or more methanol synthesis reactors, and/or a separator of the methanol purification section, wherein at least 10, 20, 30, 40, 50, 60, 70, 80, 90, or 100% of a net energy for the heating provided by the heating apparatus, the cooling provided by the cooling apparatus, or both is electrically provided. Element 12: comprising cooling apparatus downstream of each of the one or more reformers; cooling apparatus downstream of a final of the one or more reformers; cooling apparatus downstream of a water-gas shift reactor; cooling apparatus downstream of the syngas generation section and configured to condense water out of a reformer product stream; cooling apparatus downstream from one or more of the one or more methanol synthesis reactors; cooling apparatus within the methanol purification section; or a combination thereof. Element 13: comprising one or more feed preheating apparatus within the feed pretreating section; syngas heating apparatus upstream of the one or more methanol synthesis reactors; heating apparatus within the methanol purification section; or a combination thereof. Element 14: wherein compressed feed (e.g., natural gas), compressed hydrogen, cryogenic liquids, heat, electrical energy, or a combination thereof is stored, such that the stored compressed feed, compressed hydrogen, cryogenic liquids, heat, and/or electrical energy can be utilized when renewable electricity is not available. Element 15: further comprising electricity production apparatus configured to produce electricity from pressure or heat within the methanol synthesis plant. Element 16: wherein the electricity production apparatus comprises an expander, a thermoelectric device, or a combination thereof. Element 17: wherein the syngas generation section comprises a reformer fluidly connected with a hydrocarbon feed stream, wherein the hydrocarbon feed stream comprises natural gas, methane, ethane, propane, butane, naphtha, gasoil, or a combination thereof or a partial oxidation reactor fluidly connected with a partial oxidation feed, wherein the partial oxidation feed stream comprises coal, petcoke, natural gas, methane, ethane, propane, butane, naphtha, gasoil, or a combination thereof; the methanol synthesis section optionally comprises a water-gas shift reactor, with cooling apparatus upstream and downstream of the shift reactor; a water condensing apparatus downstream of the water-gas shift reactor; one or more syngas compressors to compress the syngas; and/or a heating apparatus upstream of the one or more methanol synthesis reactors; and/or the methanol purification section comprises a methanol synthesis reactor product cooling apparatus; a crude methanol recovery apparatus configured to separate the synthesis product comprising methanol into a crude methanol stream and a separated syngas stream; a recycle compressor configured to recycle at least a portion of the separated syngas stream to the one or more methanol synthesis reactors; a purge gas system operable to separate a purge gas from the separated syngas stream; and/or methanol purification apparatus configured to separate light ends, heavy byproducts, water, or a combination thereof from the crude methanol stream to provide a purified methanol product; wherein a majority or substantially all of the energy for a net heat input needed by the syngas generation section; a net heat provided by the heating apparatus; a net heat input or removal needed by the purge gas system; a net heat input required by the methanol purification apparatus; or a combination thereof is provided by electricity; and/or wherein a majority or substantial part of the compressors selected from compressors utilized to pressurize the feed stream, the one or more syngas compressors, and the recycle compressor are electrically-driven and/or are driven by steam not produced by the combustion of a fuel, a carbon-based fuel, and/or a fossil fuel. Element 18: further comprising fractionation apparatus configured to fractionate the purge gas to produce a methane stream. Element 19: wherein the fractionation comprises cryogenic fractionation. Element 20: further comprising a methanation reactor configured to, either prior to or subsequently to the fractionation, convert carbon monoxide and carbon dioxide in the purge gas to methane. Element 21: further comprising a recycle line whereby the methane produced in the methanation reactor is recycled to the syngas generation section. Element 22: configured for combustion of less than or equal to about 50, 40, 30, 20, 10, 5, 4, 3, 2, or 1 weight percent (wt %) of the purge gas. Element 23: wherein hydrogen is co-produced as a byproduct, and the methanol synthesis plant further comprises: a hydrogen separation apparatus, optionally downstream from the methanol synthesis section, configured to separate hydrogen produced in the reformer from a purge gas, thus providing a separated hydrogen, a hydrogen purification apparatus configured to purify the separated hydrogen, thus providing a purified hydrogen; and one or more fuel cells operable to make electricity from the purified hydrogen. Element 24: further comprising storage apparatus configured for storage of the separated hydrogen, the purified hydrogen, or a combination thereof, whereby the separated hydrogen, the purified hydrogen, or the combination thereof can be stored when electricity is readily available, and whereby the stored hydrogen can be utilized to make electricity in the one or more fuel cells when other sources of electricity are not readily available and/or are not available at a desirable price.

Element 25: configured for export of the separated hydrogen to an ammonia synthesis plant and/or further comprising apparatus for the production of ammonia from at least a portion of the separated hydrogen. Element 26: configured for the production of less than or equal to about 2 tons of a combustion flue gas produced via combustion of a fuel, a carbon-based fuel, a fossil fuel, or a combination thereof per ton of methanol produced. Element 27: further comprising one or more air separation units (ASUs), wherein at least 5%, 10%, 20%, 30%, 40%, 50%, 60%, 70%, 80%, 90%, a majority, or all of the energy required for the one or more ASUs is supplied by electricity. Element 28: configured for: introduction of carbon dioxide upstream of the one or more methanol synthesis reactors to consume extra hydrogen, balance the heat in the one or more methanol synthesis reactors (e.g., make it less exothermic so that there is less required heat removal in the methanol synthesis section), and allow for the electric conversion of $CO_2$ to methanol; and/or introduction of $CO_2$ to a water gas shift (WGS) reactor, to provide for endothermic and low-temperature WGS and/or an easy and low-temperature sink for electricity and/or excess low-grade heat from cooling product streams. Element 29: configured for the production of carbon dioxide ($CO_2$) by combustion in the syngas generation section to add heat to the syngas generation section and reduce heat generation in the one or more methanol synthesis reactors. Element 30: configured for production of the carbon dioxide via combustion of a renewable (e.g., a non-fossil) fuel.

Additional Disclosure Part II

The following are non-limiting, specific embodiments in accordance with the present disclosure:

A first embodiment, which is a methanol synthesis plant comprising a feed pretreating section operable to pretreat a feed stream comprising LPG, naphtha, biogas, methane, ethane, propane, butane, naphtha boiling range components, coal, petcoke, or a combination thereof, a synthesis gas (syngas) generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream, a methanol synthesis section comprising one or more methanol synthesis reactors operable to produce a synthesis product comprising methanol; and/or a methanol purification section operable to remove at least one component from the synthesis product to provide a purified methanol product, wherein the methanol synthesis plant is configured such that, relative to a conventional methanol synthesis plant, more of the net energy required by the methanol synthesis plant, the feed pretreating section, the syngas generation section, the methanol synthesis section, the methanol purification section, or a combination thereof, is provided by a non-carbon based energy source, a renewable energy source, and/or electricity.

A second embodiment, which is the methanol synthesis plant of the first embodiment, wherein the non-carbon based energy source comprises electricity.

A third embodiment, which is a methanol synthesis plant comprising a feed pretreating section operable to pretreat a feed stream comprising LPG, naphtha, biogas, methane, ethane, propane, butane, naphtha boiling range components, coal, petcoke, or a combination thereof, a syngas generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream, a methanol synthesis section comprising one or more methanol synthesis reactors operable to produce a synthesis product comprising methanol; and/or a methanol synthesis section comprising one or more methanol synthesis reactors operable to produce a synthesis product comprising methanol; and/or a methanol purification section operable to remove at least one component from the synthesis product to provide a purified methanol product, wherein the methanol synthesis plant is configured such that a majority of the net energy required by the methanol synthesis plant, the feed pretreating section, the syngas generation section, the methanol synthesis section, the methanol purification section, or a combination thereof, is provided by electricity.

A fourth embodiment, which is the methanol synthesis plant of the second or the third embodiment, wherein the electricity is produced from a renewable energy source.

A fifth embodiment, which is the methanol synthesis plant of the fourth embodiment, wherein the renewable energy source comprises wind, solar, geothermal, hydroelectric, wave, tidal, nuclear or a combination thereof.

A sixth embodiment, which is the methanol synthesis plant of the second or the third embodiment, wherein a desired syngas generation temperature within at least one of the one or more reactors can be attained without externally (e.g., in a furnace) combusting a dedicated fuel, a carbon-based fuel, or a fossil fuel.

A seventh embodiment, which is the methanol synthesis plant of the sixth embodiment, wherein the one or more reactors are heated to the desired syngas generation temperature via heating from electricity or renewable electricity and including associated convective, conductive, radiant or other heat transfer means.

An eighth embodiment, which is the methanol synthesis plant of the sixth embodiment, wherein the one or more reactors are heated resistively or inductively.

A ninth embodiment, which is the methanol synthesis plant of the second or the third embodiment, wherein other than the production of steam for use in the one or more reactors, steam is not utilized as a primary energy transfer medium, no steam is utilized for mechanical work; and/or a majority, some, or all of the steam utilized in the one or more reactors, one or more, a majority, or all steam turbines of the plant, or a combination thereof is produced electrically and/or without combusting a fossil fuel.

A tenth embodiment, which is the methanol synthesis plant of the second or the third embodiment, wherein the pretreating section, the syngas generation section, the methanol synthesis section, the methanol purification section, or a combination thereof comprises one or more compressors, and wherein at least 10, 20, 30, 40, 50, 60, 70, 80, 90, or 100% or a majority of the one or more compressors are configured for non-gas-driven operation, non-steam driven operation, and/or for operation with electrically-produced steam.

An eleventh embodiment, which is the methanol synthesis plant of the tenth embodiment, wherein at least one of the one or more compressors is configured for bifunctional operation (or 'dual drive') via both electric motor-driven and gas-driven or both electric motor-driven and steam driven operation, such that configuration of the plant enables operation of the one or more compressors via renewable electricity or steam produced from renewable electricity, when available, and operation via non-renewably produced steam or combustion, when renewable electricity is not available.

A twelfth embodiment, which is the methanol synthesis plant of the tenth embodiment comprising dual compressors for one or more compression step of the feed pretreating section, the syngas generation section, the methanol synthesis section, the methanol purification section, or a combination thereof, such that the compression step can be effected via a first of the dual compressors that is online when a second of the dual compressors is offline, and vice versa, wherein the first of the dual compressors is electric motor-driven, and the second of the dual compressors is steam-driven or combustion-driven, such that configuration of the plant enables operation of the one or more compressors via renewable electricity or steam produced from renewable electricity, when available, and operation via non-renewably produced steam or combustion, when renewable electricity is not available.

A thirteenth embodiment, which is the methanol synthesis plant of the second or the third embodiment comprising apparatus for cooling or heating a process stream, the one or more reforming reactors, the one or more methanol synthesis reactors, and/or a separator of the methanol purification section, wherein at least 10, 20, 30, 40, 50, 60, 70, 80, 90, or 100% of a net energy for the heating provided by the heating apparatus, the cooling provided by the cooling apparatus, or both is electrically provided.

A fourteenth embodiment, which is the methanol synthesis plant of the thirteenth embodiment comprising cooling apparatus downstream of each of the one or more reformers; cooling apparatus downstream of a final of the one or more reformers; cooling apparatus downstream of a water-gas shift reactor; cooling apparatus downstream of the syngas generation section and configured to condense water out of a reformer product stream; cooling apparatus downstream from one or more of the one or more methanol synthesis reactors; cooling apparatus within the methanol purification section; or a combination thereof.

A fifteenth embodiment, which is the methanol synthesis plant of the thirteenth embodiment comprising one or more feed preheating apparatus within the feed pretreating section; syngas heating apparatus upstream of the one or more methanol synthesis reactors; heating apparatus within the methanol purification section; or a combination thereof.

A sixteenth embodiment, which is the methanol synthesis plant of the second or the third embodiment, wherein compressed feed (e.g., natural gas), compressed hydrogen, cryogenic liquids, heat, electrical energy, or a combination thereof is stored, such that the stored compressed feed, compressed hydrogen, cryogenic liquids, heat, and/or electrical energy can be utilized when renewable electricity is not available.

A seventeenth embodiment, which is the methanol synthesis plant of the second or the third embodiment further comprising electricity production apparatus configured to produce electricity from pressure or heat within the methanol synthesis plant.

An eighteenth embodiment, which is the methanol synthesis plant of the seventeenth embodiment, wherein the electricity production apparatus comprises an expander, a thermoelectric device, or a combination thereof.

A nineteenth embodiment, which is the methanol synthesis plant of the second or the third embodiment, wherein the syngas generation section comprises a reformer fluidly connected with a hydrocarbon feed stream, wherein the hydrocarbon feed stream comprises natural gas, methane, ethane, propane, butane, naphtha, gasoil, or a combination thereof or a partial oxidation reactor fluidly connected with a partial oxidation feed, wherein the partial oxidation feed stream comprises coal, petcoke, natural gas, methane, ethane, propane, butane, naphtha, gasoil, or a combination thereof, the methanol synthesis section optionally comprises a water-gas shift reactor, with cooling apparatus upstream and downstream of the shift reactor; a water condensing apparatus downstream of the water-gas shift reactor; one or more syngas compressors to compress the syngas; and/or a heating apparatus upstream of the one or more methanol synthesis reactors; and/or the methanol purification section comprises a methanol synthesis reactor product cooling apparatus; a crude methanol recovery apparatus configured to separate the synthesis product comprising methanol into a crude methanol stream and a separated syngas stream; a recycle compressor configured to recycle at least a portion of the separated syngas stream to the one or more methanol synthesis reactors; a purge gas system operable to separate a purge gas from the separated syngas stream; and/or methanol purification apparatus configured to separate light ends, heavy byproducts, water, or a combination thereof from the crude methanol stream to provide a purified methanol product, wherein a majority or substantially all of the energy for a net heat input needed by the syngas generation section; a net heat provided by the heating apparatus; a net heat input or removal needed by the purge gas system; a net heat input required by the methanol purification apparatus; or a combination thereof is provided by electricity; and/or wherein a majority or substantial part of the compressors selected from compressors utilized to pressurize the feed stream, the one or more syngas compressors, and the recycle compressor are electrically-driven and/or are driven by steam not produced by the combustion of a fuel, a carbon-based fuel, and/or a fossil fuel.

A twentieth embodiment, which is the methanol synthesis plant of the nineteenth embodiment further comprising fractionation apparatus configured to fractionate the purge gas to produce a methane stream.

A twenty-first embodiment, which is the methanol synthesis plant of the twentieth embodiment, wherein the fractionation comprises cryogenic fractionation.

A twenty-second embodiment, which is the methanol synthesis plant of the twentieth embodiment comprising a methanation reactor configured to, either prior to or subsequently to the fractionation, convert carbon monoxide and carbon dioxide in the purge gas to methane.

A twenty-third embodiment, which is the methanol synthesis plant of the twentieth embodiment further comprising a recycle line whereby the methane produced in the methanation reactor is recycled to the syngas generation section.

A twenty-fourth embodiment, which is the methanol synthesis plant of the nineteenth embodiment, configured for combustion of less than or equal to about 50, 40, 30, 20, 10, 5, 4, 3, 2, or 1 weight percent (wt %) of the purge gas.

A twenty-fifth embodiment, which is the methanol synthesis plant of the second or the third embodiment, wherein hydrogen is co-produced as a byproduct, and the methanol synthesis plant further comprises a hydrogen separation apparatus, optionally downstream from the methanol synthesis section, configured to separate hydrogen produced in the reformer from a purge gas, thus providing a separated hydrogen, a hydrogen purification apparatus configured to purify the separated hydrogen, thus providing a purified hydrogen, and one or more fuel cells operable to make electricity from the purified hydrogen.

A twenty-sixth embodiment, which is the methanol synthesis plant of the twenty-fifth embodiment further comprising storage apparatus configured for storage of the separated hydrogen, the purified hydrogen, or a combination thereof, whereby the separated hydrogen, the purified hydrogen, or the combination thereof can be stored when electricity is readily available, and whereby the stored hydrogen can be utilized to make electricity in the one or more fuel cells when other sources of electricity are not readily available and/or are not available at a desirable price.

A twenty-seventh embodiment, which is the methanol synthesis plant of the twenty-fifth embodiment, configured for export of the separated hydrogen to an ammonia synthesis plant and/or further comprising apparatus for the production of ammonia from at least a portion of the separated hydrogen.

A twenty-eighth embodiment, which is the methanol synthesis plant of the first, the second, or the third embodiment, configured for the production of less than or equal to about 2 tons of a combustion flue gas produced via combustion of a fuel, a carbon-based fuel, a fossil fuel, or a combination thereof per ton of methanol produced.

A twenty-ninth embodiment, which is the methanol synthesis plant of the second or the third embodiment further comprising one or more air separation units (ASUs), wherein at least 5%, 10%, 20%, 30%, 40%, 50%, 60%, 70%, 80%, 90%, a majority, or all of the energy required for the one or more ASUs is supplied by electricity.

A thirtieth embodiment, which is the methanol synthesis plant of the second or the third embodiment, configured for introduction of carbon dioxide upstream of the one or more methanol synthesis reactors to consume extra hydrogen, balance the heat in the one or more methanol synthesis reactors (e.g., make it less exothermic so that there is less required heat removal in the methanol synthesis section), and allow for the electric conversion of $CO_2$ to methanol; and/or introduction of $CO_2$ to a water gas shift (WGS) reactor, to provide for endothermic and low-temperature WGS and/or an easy and low-temperature sink for electricity and/or excess low-grade heat from cooling product streams.

A thirty-first embodiment, which is the methanol synthesis plant of the second or the third embodiment, configured for the production of carbon dioxide ($CO_2$) by combustion in the syngas generation section to add heat to the syngas generation section and reduce heat generation in the one or more methanol synthesis reactors.

A thirty-second embodiment, which is the methanol synthesis plant of the thirty-first embodiment, configured for production of the carbon dioxide via combustion of a renewable (e.g., a non-fossil) fuel.

Additional Disclosure Part III

The following are non-limiting, specific embodiments in accordance with the present disclosure:

Embodiments disclosed herein include:

A: A method of producing methanol in a methanol synthesis plant, the method comprising: (a) subjecting a feed comprising methane, ethane, propane, butane, LPG, naphtha, biogas, or a combination thereof to reforming to produce a reformer product comprising carbon monoxide and hydrogen, wherein a reforming temperature is maintained by a net heat input Q1; (b) cooling the reformer product to produce a cooled reformer product by effecting a net heat removal Q2; (c) shifting the reformer product to produce a shifted reformer product; (d) cooling the shifted product by effecting a net heat removal Q3; (e) cooling and condensing water from the reformer product by effecting a net heat removal Q4 to provide a purified reformer product; (f) compressing the purified reformer product; (g) heating the compressed, purified reformer product by a net heat input Q5 to provide a methanol synthesis feed; (h) producing a product comprising methanol from the methanol synthesis feed; (i) cooling the product comprising methanol by a net heat removal Q6 to remove a crude methanol stream and provide a recycle gas stream comprising carbon monoxide and hydrogen; (j) compressing the recycle gas stream via a recycle compressor; (k) purging via a purge gas system, wherein purging may be effected by a net heat input or removal Q7; (l) purifying the methanol in the crude methanol product by removing light ends, heavy byproducts, water, or a combination thereof from the crude methanol stream, wherein removing the light ends, the heavy byproducts, the water, or the combination thereof requires a net heat input or removal Q8; or (m) a combination thereof, wherein, relative to a conventional method of producing methanol, more of the energy required for a net energy input or removal for a given step (a), (b), (c), (d), (e), (f), (g), (h), (i), (j), (k), (l), or a combination thereof (m), throughout the entire methanol synthesis plant, the compressing, or a combination thereof is provided by a non-carbon based energy source, a renewable energy source, and/or electricity.

B: A method of producing methanol in a methanol synthesis plant, the method comprising: (a) subjecting a feed comprising methane, ethane, propane, butane, LPG, naphtha, biogas, or a combination thereof to reforming to produce a reformer product comprising carbon monoxide and hydrogen, wherein a reforming temperature is maintained by a net heat input Q1; (b) cooling the reformer product to produce a cooled reformer product by effecting a net heat removal Q2; (c) shifting the reformer product to produce a shifted reformer product; (d) cooling the shifted product by effecting a net heat removal Q3; (e) cooling and condensing water from the reformer product by effecting a net heat removal Q4 to provide a purified reformer product; (f) compressing the purified reformer product; (g) heating the compressed, purified reformer product by a net heat input Q5 to provide a methanol synthesis feed; (h) producing a product comprising methanol from the methanol synthesis feed; (i) cooling the product comprising methanol by a net heat removal Q6 to remove a crude methanol stream and provide a recycle gas stream comprising carbon monoxide and hydrogen; (j) compressing the recycle gas stream via a recycle compressor; (k) purging via a purge gas system, wherein purging is effected by a net heat input or removal Q7; (l) purifying the methanol in the crude methanol product by removing light ends, heavy byproducts, water, or a combination thereof from the crude methanol stream, wherein removing the light ends, the heavy byproducts, the water, or the combination thereof requires a net heat input or removal Q8; or (m) a combination thereof, wherein a majority of the energy required for a net energy input or removal for a given step (a), (b), (c), (d), (e), (f), (g), (h), (i), (j), (k), (l), or a combination thereof (m), throughout the entire methanol synthesis plant, the compressing, or a combination thereof is provided by a non-carbon based energy source, a renewable energy source, and/or electricity.

C: A method of producing methanol, the method comprising: (a) reforming a reformer feed comprising methane, natural gas, ethane, propane, butane, naphtha, coal, or a combination thereof to produce a reformer product comprising synthesis gas; (b) optionally shifting the reformer product to produce a shifted product comprising carbon monoxide, carbon dioxide and hydrogen; (c) removing water from the reformer product or the shifted product to provide a dry syngas; (d) optionally compressing the dry syngas to provide a compressed, dry syngas; (e) heating the optionally compressed, dry syngas to provide a methanol synthesis feed; (f)

synthesizing methanol from the methanol synthesis feed to provide a methanol synthesis product; and/or (g) purifying the methanol synthesis product to produce a purified methanol product, wherein a majority or greater than or equal to about 40, 50, 60, 70, 80, or 90% of the net energy needed in (a), (b), (c), (d), (e), (f), (g) or a combination thereof is provided by a non-carbon based energy source, a renewable energy source, electricity, or a combination thereof.

Each of embodiments A, B, and C may have one or more of the following additional elements: Element 1: wherein the non-carbon based energy source comprises electricity. Element 2: wherein the electricity is produced from a renewable energy source. Element 3: wherein the renewable energy source comprises wind, solar, geothermal, hydroelectric, nuclear, tide, wave, or a combination thereof. Element 4: wherein maintaining the reforming temperature is effected without combusting a fuel, a fossil fuel, a carbon-based fuel, or a combination thereof externally to the feed. Element 5: wherein the non-carbon based energy source comprises or the electricity is produced via an intermittent energy source (IES), and further comprising maintaining the reforming temperature without combusting a fuel, a fossil fuel, a carbon-based fuel, or a combination thereof externally to the feed when the IES is available, and maintaining the reforming temperature via a stored supply of energy from the IES or by combusting a fuel or a carbon-based fuel when the IES is not available. Element 6: wherein the reforming is carried out in one or more reformers that are maintained at the reforming temperature via heating from electricity or renewable electricity and including associated convective, radiant or other heat transfer means. Element 7: wherein the heating from electricity or renewable electricity is resistive or inductive heating. Element 8: wherein: other than the production of steam for use in a steam methane reformer and/or a pre-reformer, steam is not utilized as a primary energy transfer medium. Element 9: wherein: a majority, some, or all of the external energy input for generating steam utilized in a steam methane reformer, a pre-reformer, one or more, a majority, or all steam turbines of the plant, or a combination thereof is electricity. Element 10: wherein heat removal in one or more or all steps (a)-(l) does not comprise the production of steam for use in a steam turbine. Element 11: wherein compressing the dry syngas or the purified reformer product, compressing the recycle gas stream, compressing the feed stream for introduction into one or more reformers, or a combination thereof comprises compressing with a compressor driven by an electric motor, an electrically-driven turbine, or a turbine driven by steam produced electrically in at least one, most, or all compressors utilized. Element 12: wherein a majority or greater than or equal to about 40, 50, 60, 70, 80, or 90% of the net energy needed for heat removal, heat input, compression, or a combination thereof in (a), (b), (c), (d), (e), (f), (g) or a combination thereof is provided by a non-carbon based energy source, a renewable energy source, electricity, or a combination thereof. Element 13: wherein (a) reforming is effected without externally burning a fuel, a fossil fuel, and/or a carbon-based fuel. Element 14: wherein utilizing a non-carbon based energy source, a renewable energy source, electricity, or a combination thereof to provide a majority or greater than or equal to about 40, 50, 60, 70, 80, or 90% of the net energy needed in (a), (b), (c), (d), (e), (f), (g) or the combination thereof results in a reduction of at least 5, 10, 20, 30, 40, 50, 60, 70, 80, 90, 95 or 98% in greenhouse gas emissions relative to a conventional method of producing methanol. Element 15: wherein the heat obtained from cooling the reformer product (e.g., via heat removal $Q2$, $Q3$, and/or $Q4$) is used to preheat the feed (e.g., used to provide a first portion of the heat input $Q1$). Element 16: wherein a second portion of the heat needed for heat input $Q1$ is provided by electrical heating, superheated steam, internal oxidation obtained by adding a small amount of oxygen or air, or a combination thereof. Element 17: wherein steam is used as a reactant or for dilution in (a), and the steam used as a reactant or diluent is generated using electricity. Element 18: wherein electric heating is used to impose a temperature profile on a reformer of (a), a water-gas shift reactor of (c), a methanol synthesis reactor of (h), or a combination thereof Element 19: wherein mechanical heating is used to heat the feed to a reformer of (a), a water-gas shift reactor of (c), a methanol synthesis reactor of (h), or a combination thereof. Element 20: wherein the weight ratio of the recycle gas stream in (i) to the purge gas stream in (k) is at least 19:1. Element 21: wherein hydrogen is co-produced as a byproduct. Element 22: further comprising burning at least a portion of the co-produced hydrogen to provide heat, high-temperature steam for use as a reactant in steam reforming, or both, without producing $CO_2$. Element 23: wherein an amount of electricity consumed is greater than or equal to 20 MW. Element 24: wherein an amount of $CO_2$ produced per ton of methanol is less than 0.3 tons $CO_2$ per ton of methanol. Element 25: wherein a net specific energy consumption is less than 34 GJ/ton methanol. Element 26: wherein a carbon efficiency is greater than or equal to 82%.

Additional Disclosure Part IV

The following are non-limiting, specific embodiments in accordance with the present disclosure:

A first embodiment, which is a method of producing methanol in a methanol synthesis plant, the method comprising (a) subjecting a feed comprising methane, ethane, propane, butane, LPG, naphtha, biogas, or a combination thereof to reforming to produce a reformer product comprising carbon monoxide and hydrogen, wherein a reforming temperature is maintained by a net heat input $Q1$, (b) cooling the reformer product to produce a cooled reformer product by effecting a net heat removal $Q2$, (c) shifting the reformer product to produce a shifted reformer product, (d) cooling the shifted product by effecting a net heat removal $Q3$, (e) cooling and condensing water from the reformer product by effecting a net heat removal $Q4$ to provide a purified reformer product, (f) compressing the purified reformer product, (g) heating the compressed, purified reformer product by a net heat input $Q5$ to provide a methanol synthesis feed, (h) producing a product comprising methanol from the methanol synthesis feed, (i) cooling the product comprising methanol by a net heat removal $Q6$ to remove a crude methanol stream and provide a recycle gas stream comprising carbon monoxide and hydrogen, (j) compressing the recycle gas stream via a recycle compressor, (k) purging via a purge gas system, wherein purging may be effected by a net heat input or removal $Q7$, (l) purifying the methanol in the crude methanol product by removing light ends, heavy byproducts, water, or a combination thereof from the crude methanol stream, wherein removing the light ends, the heavy byproducts, the water, or the combination thereof requires a net heat input or removal $Q8$, or (m) a combination thereof, wherein, relative to a conventional method of producing methanol, more of the energy required for a net energy input or removal for a given step (a), (b), (c), (d), (e), (f), (g), (h), (i), (j), (k), (l), or a combination thereof (m), throughout the entire methanol synthesis plant, the compressing, or a combination thereof is provided by a non-carbon based energy source, a renewable energy source, and/or electricity.

A second embodiment, which is the method of the first embodiment, wherein the non-carbon based energy source comprises electricity.

A third embodiment, which is a method of producing methanol in a methanol synthesis plant, the method comprising (a) subjecting a feed comprising methane, ethane, propane, butane, LPG, naphtha, biogas, or a combination thereof to reforming to produce a reformer product comprising carbon monoxide and hydrogen, wherein a reforming temperature is maintained by a net heat input Q1, (b) cooling the reformer product to produce a cooled reformer product by effecting a net heat removal Q2, (c) shifting the reformer product to produce a shifted reformer product, (d) cooling the shifted product by effecting a net heat removal Q3, (e) cooling and condensing water from the reformer product by effecting a net heat removal Q4 to provide a purified reformer product, (f) compressing the purified reformer product, (g) heating the compressed, purified reformer product by a net heat input Q5 to provide a methanol synthesis feed, (h) producing a product comprising methanol from the methanol synthesis feed, (i) cooling the product comprising methanol by a net heat removal Q6 to remove a crude methanol stream and provide a recycle gas stream comprising carbon monoxide and hydrogen, (j) compressing the recycle gas stream via a recycle compressor, (k) purging via a purge gas system, wherein purging is effected by a net heat input or removal Q7, (l) purifying the methanol in the crude methanol product by removing light ends, heavy byproducts, water, or a combination thereof from the crude methanol stream, wherein removing the light ends, the heavy byproducts, the water, or the combination thereof requires a net heat input or removal Q8, or (m) a combination thereof, wherein a majority of the energy required for a net energy input or removal for a given step (a), (b), (c), (d), (e), (f), (g), (h), (i), (j), (k), (l), or a combination thereof (m), throughout the entire methanol synthesis plant, the compressing, or a combination thereof is provided by a non-carbon based energy source, a renewable energy source, and/or electricity.

A fourth embodiment, which is the method of the second or the third embodiment, wherein the electricity is produced from a renewable energy source.

A fifth embodiment, which is the method of the fourth embodiment, wherein the renewable energy source comprises wind, solar, geothermal, hydroelectric, nuclear, tide, wave, or a combination thereof.

A sixth embodiment, which is the method of the first, the second, or the third embodiment, wherein maintaining the reforming temperature is effected without combusting a fuel, a fossil fuel, a carbon-based fuel, or a combination thereof externally to the feed.

A seventh embodiment, which is the method of the sixth embodiment, wherein the non-carbon based energy source comprises or the electricity is produced via an intermittent energy source (IES), and further comprising maintaining the reforming temperature without combusting a fuel, a fossil fuel, a carbon-based fuel, or a combination thereof externally to the feed when the IES is available, and maintaining the reforming temperature via a stored supply of energy from the IES or by combusting a fuel or a carbon-based fuel when the IES is not available.

An eighth embodiment, which is the method of the second or the third embodiment, wherein the reforming is carried out in one or more reformers that are maintained at the reforming temperature via heating from electricity or renewable electricity and including associated convective, radiant or other heat transfer means.

A ninth embodiment, which is the method of the eighth embodiment, wherein the heating from electricity or renewable electricity is resistive or inductive heating.

A tenth embodiment, which is the method of the second or the third embodiment, wherein other than the production of steam for use in a steam methane reformer and/or a pre-reformer, steam is not utilized as a primary energy transfer medium.

An eleventh embodiment, which is the method of the tenth embodiment, wherein a majority, some, or all of the external energy input for generating steam utilized in a steam methane reformer, a pre-reformer, one or more, a majority, or all steam turbines of the plant, or a combination thereof is electricity.

A twelfth embodiment, which is the method of the second or the third embodiment, wherein heat removal in one or more or all steps (a)-(l) does not comprise the production of steam for use in a steam turbine.

A thirteenth embodiment, which is the method of the second or the third embodiment, wherein compressing the dry syngas or the purified reformer product, compressing the recycle gas stream, compressing the feed stream for introduction into one or more reformers, or a combination thereof comprises compressing with a compressor driven by an electric motor, an electrically-driven turbine, or a turbine driven by steam produced electrically in at least one, most, or all compressors utilized.

A fourteenth embodiment, which is the method of the second or the third embodiment, wherein the heat obtained from cooling the reformer product (e.g., via heat removal Q2, Q3, and/or Q4) is used to preheat the feed (e.g., used to provide a first portion of the heat input Q1).

A fifteenth embodiment, which is the method of the fourteenth embodiment, wherein a second portion of the heat needed for heat input Q1 is provided by electrical heating, superheated steam, internal oxidation obtained by adding a small amount of oxygen or air, or a combination thereof.

A sixteenth embodiment, which is the method of the second or the third embodiment, wherein steam is used as a reactant or for dilution in (a), and the steam used as a reactant or diluent is generated using electricity.

A seventeenth embodiment, which is the method of the second or the third embodiment, wherein electric heating is used to impose a temperature profile on a reformer of (a), a water-gas shift reactor of (c), a methanol synthesis reactor of (h), or a combination thereof An eighteenth embodiment, which is the method of the second or the third embodiment, wherein mechanical heating is used to heat the feed to a reformer of (a), a water-gas shift reactor of (c), a methanol synthesis reactor of (h), or a combination thereof.

A nineteenth embodiment, which is the method of the second or the third embodiment, wherein the weight ratio of the recycle gas stream in (i) to the purge gas stream in (k) is at least 19:1.

A twentieth embodiment, which is the method of the second or the third embodiment, wherein hydrogen is co-produced as a byproduct.

A twenty-first embodiment, which is the method of the twentieth embodiment further comprising burning at least a portion of the co-produced hydrogen to provide heat, high-temperature steam for use as a reactant in steam reforming, or both, without producing $CO_2$.

A twenty-second embodiment, which is the method of the second or the third embodiment, wherein an amount of electricity consumed is greater than or equal to 20 MW.

A twenty-third embodiment, which is the method of the first, the second, or the third embodiment, wherein an amount of $CO_2$ produced per ton of methanol is less than 0.3 tons $CO_2$ per ton of methanol.

A twenty-fourth embodiment, which is the method of the first, the second, or the third embodiment, wherein a net specific energy consumption is less than 34 GJ/ton methanol.

A twenty-fifth embodiment, which is the method of the first, the second, or the third embodiment, wherein a carbon efficiency is greater than or equal to 82%.

A twenty-sixth embodiment, which is a method of producing methanol, the method comprising (a) reforming a reformer feed comprising methane, natural gas, ethane, propane, butane, naphtha, coal, or a combination thereof to produce a reformer product comprising synthesis gas, (b) shifting the reformer product to produce a shifted product comprising carbon monoxide, carbon dioxide and hydrogen, (c) removing water from the reformer product or the shifted product to provide a dry syngas, (d) compressing the dry syngas to provide a compressed, dry syngas, (e) heating the compressed, dry syngas to provide a methanol synthesis feed, (f) synthesizing methanol from the methanol synthesis feed to provide a methanol synthesis product, and/or (g) purifying the methanol synthesis product to produce a purified methanol product, wherein a majority or greater than or equal to about 40, 50, 60, 70, 80, or 90% of the net energy needed in (a), (b), (c), (d), (e), (f), (g) or a combination thereof is provided by a non-carbon based energy source, a renewable energy source, electricity, or a combination thereof.

A twenty-seventh embodiment, which is the method of the twenty-sixth embodiment, wherein a majority or greater than or equal to about 40, 50, 60, 70, 80, or 90% of the net energy needed for heat removal, heat input, compression, or a combination thereof in (a), (b), (c), (d), (e), (f), (g) or a combination thereof is provided by a non-carbon based energy source, a renewable energy source, electricity, or a combination thereof.

A twenty-eighth embodiment, which is the method of the twenty-sixth embodiment, wherein (a) reforming is effected without externally burning a fuel, a fossil fuel, and/or a carbon-based fuel.

A twenty-ninth embodiment, which is the method of the twenty-sixth embodiment, wherein utilizing a non-carbon based energy source, a renewable energy source, electricity, or a combination thereof to provide a majority or greater than or equal to about 40, 50, 60, 70, 80, or 90% of the net energy needed in (a), (b), (c), (d), (e), (f), (g) or the combination thereof results in a reduction of at least 5, 10, 20, 30, 40, 50, 60, 70, 80, 90, 95 or 98% in greenhouse gas emissions relative to a conventional method of producing methanol.

A thirtieth embodiment, which is a methanol synthesis method or apparatus as described herein.

Additional Disclosure Part V

The following are non-limiting, specific embodiments in accordance with the present disclosure:

A first embodiment, which is a methanol synthesis plant comprising a feed pretreating section operable to pretreat a feed stream comprising LPG, naphtha, biogas, methane, ethane, propane, butane, naphtha boiling range components, coal, petcoke, or a combination thereof, a synthesis gas (syngas) generation section comprising one or more reactors selected from pre-reformers, steam reformers, dry reformers, partial oxidation reactors, autothermal reformers, gasifiers, or a combination thereof and operable to produce a syngas synthesis product stream comprising synthesis gas from the feed stream, a methanol synthesis section comprising one or more methanol synthesis reactors operable to produce a synthesis product comprising methanol, and a methanol purification section operable to remove at least one component from the synthesis product to provide a purified methanol product; wherein methanol synthesis plant consumes greater than or equal to 20 MW of electricity, wherein an amount of $CO_2$ produced per ton of methanol is less than 0.3 tons $CO_2$ per ton of methanol, and wherein a net specific energy consumption is less than 34 GJ/ton methanol.

A second embodiment, which is the methanol synthesis plant according to the first embodiment, wherein a carbon efficiency is greater than or equal to 82%.

A third embodiment, which is the methanol synthesis plant according to the first or the second embodiment, wherein a predetermined syngas generation temperature within at least one of the one or more reactors can be attained without externally combusting a dedicated fuel, a non-renewable carbon-based fuel, or a fossil fuel.

A fourth embodiment, which is the methanol synthesis plant according to any of the first through the third embodiments, wherein the methanol synthesis plant does not include a flue gas heat recovery section.

A fifth embodiment, which is the methanol synthesis plant according to any of the first through the fourth embodiments, wherein the one or more reactors are heated to a predetermined syngas generation temperature via heating from electricity and associated convective, conductive, radiant, or inductive heat transfer means.

A sixth embodiment, which is the methanol synthesis plant according to any of the first through the fifth embodiments, wherein other than the production of steam for use in the one or more reactors, steam is not utilized as a primary energy transfer medium, or no steam is utilized for mechanical work.

A seventh embodiment, which is the methanol synthesis plant according to any of the first through the sixth embodiments, further comprising cooling apparatus downstream of each of the one or more reformers; cooling apparatus downstream of a final of the one or more reformers; cooling apparatus downstream of a water-gas shift reactor; cooling apparatus downstream of the syngas generation section and configured to condense water out of a reformer product stream; cooling apparatus downstream from one or more of the one or more methanol synthesis reactors; cooling apparatus within the methanol purification section; or a combination thereof, wherein at least 50% of a net energy for the cooling apparatus is electrically provided.

An eighth embodiment, which is the methanol synthesis plant according to any of the first through the seventh embodiments, wherein compressed feed, compressed hydrogen, cryogenic liquids, heat, electrical energy, or a combination thereof is stored, such that the stored compressed feed, compressed hydrogen, cryogenic liquids, heat, and/or electrical energy can be utilized when renewable electricity is not available.

A ninth embodiment, which is the methanol synthesis plant according to any of the first through the eighth embodiments, further comprising a fractionation apparatus configured to fractionate a purge gas to produce a methane stream, and a methanation reactor configured to, either prior to or subsequently to the fractionation, convert carbon monoxide and carbon dioxide in the purge gas to methane.

A tenth embodiment, which is the methanol synthesis plant according to the ninth embodiment, configured for combustion of less than or equal to about 50 weight percent (wt %) of the purge gas.

An eleventh embodiment, which is the methanol synthesis plant according to any of the first through the tenth embodiments, wherein hydrogen is co-produced as a byproduct, and the methanol synthesis plant further comprises a hydrogen separation apparatus, optionally downstream from the methanol synthesis section, configured to separate hydrogen produced in the reformer from a purge gas, thus providing a separated hydrogen, a hydrogen purification apparatus configured to purify the separated hydrogen, thus providing a purified hydrogen, and one or more fuel cells operable to make electricity from the purified hydrogen.

A twelfth embodiment, which is the methanol synthesis plant according to any of the first through the eleventh embodiments, wherein the methanol synthesis plant is configured for the production of less than or equal to about two tons of a combustion flue gas produced via combustion of a fuel per ton of methanol produced.

A thirteenth embodiment, which is the methanol synthesis plant according to any of the first through the twelfth embodiments, configured for introduction of carbon dioxide upstream of the one or more methanol synthesis reactors to consume extra hydrogen, balance the heat in the one or more methanol synthesis reactors, and allow for the electric conversion of $CO_2$ to methanol, or introduction of $CO_2$ to a water gas shift (WGS) reactor.

A fourteenth embodiment, which is the methanol synthesis plant according to any of the first through the thirteenth embodiments, configured for the production of carbon dioxide ($CO_2$) by combustion in the syngas generation section to add heat to the syngas generation section and reduce heat generation in the one or more methanol synthesis reactors.

A fifteenth embodiment, which is a method of producing methanol in a methanol synthesis plant, the method comprising (a) subjecting a feed comprising methane, ethane, propane, butane, LPG, naphtha, biogas, or a combination thereof to reforming to produce a reformer product comprising carbon monoxide and hydrogen, wherein a reforming temperature is maintained by a net heat input $Q1$, (b) cooling the reformer product to produce a cooled reformer product by effecting a net heat removal $Q2$, (c) shifting the reformer product to produce a shifted reformer product, (d) cooling the shifted product by effecting a net heat removal $Q3$, (e) cooling and condensing water from the reformer product by effecting a net heat removal $Q4$ to provide a purified reformer product, (f) compressing the purified reformer product, (g) heating the compressed, purified reformer product by a net heat input $Q5$ to provide a methanol synthesis feed, (h) producing a product comprising methanol from the methanol synthesis feed, (i) cooling the product comprising methanol by a net heat removal $Q6$ to remove a crude methanol stream and provide a recycle gas stream comprising carbon monoxide and hydrogen, (j) compressing the recycle gas stream via a recycle compressor, (k) purging via a purge gas system, wherein purging may be effected by a net heat input or removal $Q7$, and (l) purifying the methanol in the crude methanol product by removing light ends, heavy byproducts, water, or a combination thereof from the crude methanol stream, wherein removing the light ends, the heavy byproducts, the water, or the combination thereof requires a net heat input or removal $Q8$, wherein the method consumes greater than or equal to 20

MW of electricity per day, wherein an amount of $CO_2$ produced per ton of methanol is less than 0.3 tons $CO_2$ per ton of methanol, and wherein a net specific energy consumption is less than 34 GJ/ton methanol.

A sixteenth embodiment, which is the method according to the fifteenth embodiment, wherein a carbon efficiency is greater than or equal to 82%.

A seventeenth embodiment, which is the method according to the fifteenth or the sixteenth embodiment, wherein the heat obtained from cooling the reformer product via heat removal $Q2$, $Q3$, and $Q4$ is used to preheat the feed by providing a first portion of the heat input $Q1$.

An eighteenth embodiment, which is the method according to any of the fifteenth through the seventeenth embodiments, wherein a second portion of the heat needed for heat input $Q1$ is provided by electrical heating, superheated steam, internal oxidation obtained by adding a small amount of oxygen or air, or a combination thereof.

A nineteenth embodiment, which is the method according to any of the fifteenth through the eighteenth embodiments, wherein steam is only used as a reactant or for dilution in (a), and the steam used as a reactant or diluent is generated using electric heating.

A twentieth embodiment, which is the method according to any of the fifteenth through the nineteenth embodiments, wherein mechanical heating is used to heat the feed to a reformer of (a), a water-gas shift reactor of (c), a methanol synthesis reactor of (h), or a combination thereof.

A twenty-first embodiment, which is the method according to any of the fifteenth through the twentieth embodiments, wherein the weight ratio of the recycle gas stream in (i) to the purge gas stream in (k) is at least 19:1.

A twenty-second embodiment, which is the method of according to any of the fifteenth through the twenty-first embodiments, wherein hydrogen is co-produced as a byproduct, and further comprising burning at least a portion of the co-produced hydrogen to provide heat, high-temperature steam for use as a reactant in steam reforming, or both, without producing $CO_2$.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A methanol synthesis system comprising:
   a feed conduit positioned to supply a feed stream comprising LPG, naphtha, biogas, methane, ethane, propane, butane, naphtha boiling range components, coal, petcoke or a combination thereof;

a feed pretreating section in flow communication with the feed conduit and arranged to apply thermal energy from at least one of an electrically-powered heater or electrically-produced steam to the feed stream to provide a pre-heated feed stream;

a syngas synthesis section arranged to receive the preheated feed stream and convert it to a syngas product;

a methanol synthesis section arranged to receive the syngas product and produce a crude methanol product; and a crude methanol recovery section arranged to receive the crude methanol product and separate methanol from the crude methanol product.

2. The methanol synthesis system according to claim 1, wherein the syngas synthesis section comprises an oxidative reforming reactor in flow communication with an electrically-powered air separation unit and a reforming reactor heated by heat exchange with an effluent of the oxidative reforming reactor.

3. The methanol synthesis system according to claim 1, wherein the syngas synthesis section comprises an electrically-heated reforming reactor and optionally an autothermal reforming reactor in flow communication with an electrically-powered air separation unit.

4. The methanol synthesis system according to claim 1, further comprising a syngas cooling apparatus powered by electricity and arranged to receive the syngas product and remove thermal energy from the syngas product prior to being fed to the methanol synthesis apparatus.

5. The methanol synthesis system according to claim 4, further comprising an electricity-driven compressor arranged to receive the syngas product from the syngas cooling apparatus and compress the syngas product prior to it being fed to the methanol synthesis apparatus.

6. The methanol system according to claim 1, further comprising a cooling apparatus powered by electricity and arranged to receive the crude methanol product from the methanol synthesis section and remove thermal energy from the crude methanol product.

7. The methanol synthesis system according to claim 1, wherein the crude methanol recovery section comprises an electrically-powered separation apparatus arranged to receive the crude methanol product and form a water/methanol product and a syngas vapor.

8. The methanol synthesis system according to claim 7, further comprising a hydrogen separation apparatus arranged to receive the syngas vapor and recover hydrogen from the syngas vapor.

9. The methanol synthesis system according to claim 7, further comprising a cryogenic separation apparatus arranged to receive the syngas vapor and recover methane, nitrogen, argon or a combination thereof from the syngas vapor.

10. The methanol synthesis system of claim 7, further comprising an electrically-powered compression apparatus arranged to receive the syngas vapor, compress the syngas vapor and recycle the compressed syngas vapor to the methanol synthesis section.

11. A method of producing methanol in the methanol synthesis system according to claim 1, the method comprising:

a) heating a feedstock in the feed pretreating section by applying a net heat input Q1 to the feedstock to form a preheated feedstock;

b) removing one or more impurities from the preheated feedstock to form a pretreated feedstock;

c) converting the pretreated feedstock to a syngas product in the syngas synthesis section by applying a net heat input Q2 to the pretreated feedstock;

d) cooling the syngas product by applying a net heat removal Q3 to the syngas product to form a cooled syngas product;

e) feeding the cooled syngas product to a methanol synthesis reactor comprising the methanol synthesis section to form a methanol synthesis product;

f) cooling the methanol synthesis product by applying a net heat removal Q4 to the methanol synthesis product to form a crude methanol product and a recycle gas stream; and g) recovering methanol from the crude methanol product in the crude methanol recovery section by applying at least one of a net heat input Q5 or a net heat removal Q6 to remove light ends, heavy byproducts, water or a combination thereof from the crude methanol product, wherein energy consumed to provide the net heat inputs Q1, Q2 and Q5 and the net heat removals Q3, Q4 and Q6 are provided from electricity and wherein the feedstock comprises LPG, naphtha, biogas, methane, ethane, propane, butane, naphtha boiling range components, coal, petcoke, or a combination thereof.

12. The method according to claim 11, wherein the electricity is provided by a non-carbon based energy source.

13. The method according to claim 11, further comprising feeding at least a portion of the recycle gas stream to a purge gas system to purge the portion of the recycle gas stream from the methanol synthesis system wherein energy consumed by the purge gas system is provided by electricity.

14. The method according to claim 11, further comprising feeding at least a portion of the recycle gas stream to an electrically-powered compressor to compress the recycle gas stream and recycling the compressed recycle gas stream to the methanol synthesis reactor.

15. The method according to claim 11, further comprising recycling a portion of the recycle gas stream to the feedstock or the pretreated feedstock.

16. The method according to claim 11, further comprising feeding the recycle gas stream to a hydrogen separation apparatus and optionally a hydrogen purification apparatus to separate hydrogen from the recycle purge gas stream.

17. The method according to claim 11, further comprising heating water by applying a net heat input Q7 to the water to form steam and mixing the steam with the feedstock wherein energy consumed to provide the net energy input Q7 is provided from electricity.

18. A method to produce methanol in the methanol synthesis system of claim 1 from a feedstock, the method comprising:

applying in the feed pretreating section a net heat input Q1 to the feedstock to preheat the feedstock;

subjecting the feedstock in the syngas synthesis section to reforming to produce a reformer product comprising carbon monoxide and hydrogen;

subjecting the reformer product in the methanol synthesis section to methanol synthesis to form a crude methanol product;

subjecting the crude methanol product in the crude methanol recover section to crude methanol recovery to form methanol and a recycle gas stream; and recovering hydrogen from the recycle gas stream wherein at least a portion of the hydrogen recovered from the crude methanol product is burned either to provide the net heat input Q1, used as a reactant in reforming, or both, without producing $CO_2$.

19. The method according to claim 18, further comprising purging the recycle gas stream via a purge gas system.

20. The method according to claim 18, further comprising feeding the recycle gas stream to a cryogenic fractionation apparatus to separate methane, nitrogen, argon or a combination thereof from the recycle gas stream.

\* \* \* \* \*